(12) United States Patent
Dill

(10) Patent No.: US 10,539,561 B1
(45) Date of Patent: Jan. 21, 2020

(54) ENZYME-AMPLIFIED REDOX MICROARRAY DETECTION PROCESS

(75) Inventor: Kilian Dill, Monroe, WA (US)

(73) Assignee: CustomArray, Inc., Bothwell, WA (US)

( * ) Notice: Subject to any disclaimer, the term of this patent is extended or adjusted under 35 U.S.C. 154(b) by 109 days.

(21) Appl. No.: 09/944,727

(22) Filed: Aug. 30, 2001

(51) Int. Cl.
*G01N 33/53* (2006.01)
*G01N 33/543* (2006.01)
*C12Q 1/6825* (2018.01)

(52) U.S. Cl.
CPC ... *G01N 33/5438* (2013.01); *G01N 33/54353* (2013.01); *C12Q 1/6825* (2013.01); *G01N 33/53* (2013.01)

(58) Field of Classification Search
USPC ............... 422/82.01–82.04; 435/6, 7.71
See application file for complete search history.

(56) References Cited

U.S. PATENT DOCUMENTS

| | | | |
|---|---|---|---|
| 3,720,591 A | 3/1973 | Skarlos | |
| 3,950,357 A | 4/1976 | Kahan | |
| 4,165,320 A | 8/1979 | Ondetti | |
| 4,563,263 A | 1/1986 | Oyama | |
| 4,840,893 A * | 6/1989 | Hill et al. | .............. 435/6.16 |
| 5,143,854 A | 9/1992 | Pirrung | |
| 5,268,266 A * | 12/1993 | Fritsch | ........... C12Q 1/6813 435/6.11 |
| 5,445,934 A | 8/1995 | Fodor | |
| 5,510,270 A | 4/1996 | Fodor | |
| 5,540,828 A | 7/1996 | Yacynych | |
| 5,653,939 A | 8/1997 | Hollis | |
| 5,667,667 A | 9/1997 | Southern | |
| 5,695,940 A | 12/1997 | Drmanac | |
| 5,723,344 A * | 3/1998 | Mabilat | ............ G01N 33/54366 422/566 |
| 5,766,550 A | 6/1998 | Kaplan | |

(Continued)

FOREIGN PATENT DOCUMENTS

| | | |
|---|---|---|
| EP | 1420252 | 5/2004 |
| JP | 2005166601 | 6/2006 |

(Continued)

OTHER PUBLICATIONS

Ashfari et al., "Application of Complementary DNA Microarray Technology to Carcinogen Identification, Toxicology, and Drug Safety Evaluation", *Cancer Res.* 59:4759, (1999).

(Continued)

*Primary Examiner* — Melanie Brown
*Assistant Examiner* — Richard Moerschell
(74) *Attorney, Agent, or Firm* — Sci-Law Strategies, PC

(57) ABSTRACT

There is disclosed a process and an array for assaying for binding of target molecules to capture molecules on micro array devices, wherein the microarray devices contain electrodes. Specifically, there is disclosed a binding (including nucleotide hybridization) process to detect binding on a microarray wherein the microarray contains electronically addressable electrode devices. There is further disclosed an enzymatically catalyzed oxidation/reduction reaction to take place within a "virtual flask" region of a micro array wherein the reaction is detected by current changes detected on the addressable electrode.

14 Claims, 52 Drawing Sheets

Specification includes a Sequence Listing.

HRP Reaction Scheme

(56) References Cited

U.S. PATENT DOCUMENTS

| | | | |
|---|---|---|---|
| 5,824,473 A * | 10/1998 | Meade | B82Y 30/00 435/287.2 |
| 5,874,047 A * | 2/1999 | Schoning | C12Q 1/001 422/204 |
| 5,912,339 A | 6/1999 | Miller | |
| 5,928,905 A | 7/1999 | Stemmer | |
| 5,929,208 A | 7/1999 | Heller | |
| 5,953,681 A | 9/1999 | Cantatore | |
| 6,013,440 A | 1/2000 | Lipshutz | |
| 6,017,696 A | 1/2000 | Heller | |
| 6,051,380 A * | 4/2000 | Sosnowski | B01J 19/0046 257/E21.43 |
| 6,066,448 A | 5/2000 | Wohlstader | |
| 6,093,302 A * | 7/2000 | Montgomery | B01J 19/0046 205/122 |
| 6,280,595 B1 * | 8/2001 | Montgomery | B01J 19/0046 205/122 |
| 6,303,082 B1 * | 10/2001 | John | G01N 27/40 422/50 |
| 6,320,041 B1 | 11/2001 | Hogrefe | |
| 6,391,558 B1 * | 5/2002 | Henkens | C12Q 1/6825 422/50 |
| 6,444,111 B1 | 9/2002 | Montgomery | |
| 6,456,942 B1 | 9/2002 | Anderson | |
| 6,475,699 B2 | 11/2002 | Uetani | |
| 6,518,024 B2 * | 2/2003 | Choong | G01N 33/5438 435/6.12 |
| 6,576,426 B2 | 6/2003 | Southern | |
| 6,586,211 B1 | 7/2003 | Stahler | |
| 6,743,564 B2 | 6/2004 | Hatakeyama | |
| 6,780,582 B1 | 8/2004 | Wagner | |
| 6,824,669 B1 * | 11/2004 | Li | G01N 33/5438 204/403.01 |
| 6,921,636 B1 | 7/2005 | Brennan | |
| 6,960,298 B2 | 11/2005 | Krotz | |
| 7,008,769 B2 | 3/2006 | Henderson | |
| 7,541,314 B2 | 6/2009 | Suciu | |
| 7,557,069 B2 | 7/2009 | Strathmann | |
| 8,855,955 B2 | 10/2014 | Peyvan | |
| 9,267,213 B1 | 2/2016 | Maurer | |
| 9,339,782 B1 | 5/2016 | Gindilis | |
| 9,394,167 B2 | 7/2016 | Maurer | |
| 9,983,204 B2 | 5/2018 | Maurer | |
| 10,006,131 B1 | 6/2018 | Maurer | |
| 10,261,075 B2 | 4/2019 | Maurer | |
| 10,286,377 B1 | 5/2019 | Gindilis | |
| 2001/0053529 A1 * | 12/2001 | Gindilis | C12Q 1/001 435/7.1 |
| 2002/0090738 A1 | 7/2002 | Cozzette | |
| 2002/0172963 A1 | 11/2002 | Kelley | |
| 2003/0022150 A1 * | 1/2003 | Sampson | C12Q 1/6825 506/7 |
| 2003/0050437 A1 | 3/2003 | Montgomery | |
| 2003/0111356 A1 | 6/2003 | Strathmann | |
| 2003/0113713 A1 | 6/2003 | Glezer | |
| 2003/0134989 A1 | 7/2003 | Aldrich | |
| 2003/0152919 A1 * | 8/2003 | Roelens | C12Q 1/34 435/6.16 |
| 2003/0186226 A1 | 10/2003 | Brennan | |
| 2003/0190632 A1 | 10/2003 | Sosnowski | |
| 2003/0194709 A1 | 10/2003 | Yang | |
| 2004/0073017 A1 | 4/2004 | Skrzypcznski | |
| 2004/0238369 A1 | 12/2004 | Southern | |
| 2005/0043894 A1 | 2/2005 | Fernandez | |
| 2005/0212902 A1 | 9/2005 | Cook | |
| 2005/0239112 A1 | 10/2005 | Padmanabhan | |
| 2005/0272088 A1 | 12/2005 | Cook | |
| 2006/0035218 A1 | 2/2006 | Oleinikov | |
| 2006/0102471 A1 | 5/2006 | Adermann | |
| 2006/0105355 A1 | 5/2006 | Maurer | |
| 2006/0160100 A1 | 7/2006 | Gao | |
| 2006/0231411 A1 | 10/2006 | Maurer | |
| 2007/0034513 A1 | 2/2007 | Maurer | |
| 2007/0065877 A1 | 3/2007 | Maurer | |
| 2007/0072169 A1 | 3/2007 | Peyvan | |
| 2007/0231794 A1 | 10/2007 | Dill | |
| 2007/0292855 A1 | 12/2007 | Dubin | |
| 2008/0035494 A1 | 2/2008 | Gomez | |
| 2008/0039342 A1 | 2/2008 | Tian | |
| 2008/0125327 A1 | 5/2008 | Kumar | |
| 2009/0280998 A1 | 11/2009 | Maurer | |
| 2011/0281766 A1 | 11/2011 | Cooper | |
| 2016/0354751 A1 | 12/2016 | Maurer | |

FOREIGN PATENT DOCUMENTS

| | | |
|---|---|---|
| WO | WO9603417 | 2/1996 |
| WO | WO0051721 | 9/2000 |
| WO | WO0123082 | 4/2001 |
| WO | WO0231463 | 4/2002 |
| WO | WO0231481 | 4/2002 |
| WO | WO02090963 | 11/2002 |
| WO | WO02103061 | 12/2002 |
| WO | WO03020415 | 3/2003 |
| WO | WO04024886 | 3/2004 |
| WO | WO2004024886 | 3/2004 |
| WO | WO2006055810 | 5/2006 |

OTHER PUBLICATIONS

Hacia et al., "Applications of DNA chips for genomic analysis", *Mol. Psychiatry* 3:483, (1998).
Hacia, "Resequencing and mutational analysis using oligonucleotide microarrays", Nature Genetics 21 Suppl: 42, (1999).
Johnson, "Gene chips: Array of hope for understanding gene regulation" *Curr. Biol.* R171, vol. 8(5), (1998).
Kurian et al. "DNA Chip Technology", *J. Pathol.* 187:267 (1999).
Wilgenbus and Lichter, "DNA chip technology ante portas", *J. Mol. Med.* 77:761, (1999).
Patolsky, et al. "Highly Sensitive Amplified Electronic Detection of DNA . . . " Chem. Eur. J., 2003, 1137-1145, vol. 9, No. 5 Wiley-VCH Weinheim.
Wang, Joseph "Survey and Summary from DNA Biosensors . . . " Nucleic Acids Research 2000, 3011-3016, vol. 28, No. 16 Oxford University Press.
Ghindilis, et al., "Immunosensors: Electrochemical Sensing and Other . . . " Biosensors & Bioelectronics 1998, 113-131 vol. 13, No. 1 Elsevier Sciences S.A.
Dill, et al., "Immunoassays and Sequence-Specific DNA Detection on a Microchip . . . " J. Biochem. Biophys. Methods 2004, 59 181-187, Elsevier B.V.
Patolsky, et al., "Enzyme-Linked Amplified Electrochemical Sensing . . . " Langmuir 1999, vol. 15, No. 1,1 3703-3706, American Chemical Society.
Wang, et al., "Dual Enzyme Electrochemical Coding for Detecting DNA Hybridization" Analyst 2002 vol. 127, 1279-1282, The Royal Society of Chemistry.
Rossier, et al., "Enzyme Linked Immunosorbent Assay on a Microchip . . . " Lab on a Chip 2001, vol. 1, 153-157, The Royal Society of Chemistry.
Office Action, Application No. 05849631.6 PCT/US2005/041906 dated May 2, 2012, 3 pages.
Extended European Search Report, Application No. 06739757.0 PCT/US2006/011150 dated Jan. 20, 2011, 9 pages.
Article 94(3) European Communication, Application No. 05849631.6 PCT/US2005/041906, dated Nov. 25, 2015, 5 pages.
Article 116(1) European Communication, Application No. 06750351.6 PCT/US2006/014288, dated Nov. 24, 2015, 9 pages.
Office Action, Application No. 06750351.6 PCT/US2006/014288 dated Feb. 21, 2013, 4 pages.
European Search Report, Application No. EP06750351 PCT/US2006/014288 dated Dec. 2, 2010, 9 pages.
Afshari et al., "Application of Complementary DNA Microarray Technology to Carcinogen Identification . . . ", Cancer Res., 1999, pp. 4759-4760, vol. 59.
Bard et al., "Azo, Azoxy and Diazo Compounds," Encyclo. of Electrochemistry of the Elements, 1979, pp. 179-209, vol. XIII-4, NY, NY.

(56) References Cited

OTHER PUBLICATIONS

Beier et al., "Versatile Derivatisation of Solid Support Media for Convalent Bonding . . . " Nucleic Acids Research, 1999, pp. 1970-1977, vol. 27, No. 9.
Cahill and Nordhoff, "Protein Arrays & Their Role in Protemics" Adv. Biochem. Engin/Biotechnol., 2003, pp. 177-187, vol. 83.
Campbell et al., "Enzyme-Amplified Amperometric Sandwich Test for RNA and DNA" Anal. Chem., 2002, 158-162, 74(1) American Chemical Society.
Dill et al., "Antigen Detection Using Microelectrode Array Microchips" Analytica Chimica Acta, 2001, pp. 69-78, vol. 444.
Dill et al., "Immunoassays and Sequence-Specific DNA Detection on a Microchip . . . " J. Biochem. Biophys. Methods, 2004, 59 pp. 181-187, Elsevier B.V.
Drummond et al., "Electrochemical DNA Sensors" Nature Biotechnology Oct. 2003, 1192-1199, vol. 21, No. 10 Nature Publishing Group.
Egeland et al., "An Electrochemical Redox Couple Activitated by Microelectrodes for Confined Chemical Patterning of Surfaces" Analytical Chemistry (2002) vol. 74, pp. 1590-1596.
Fledler et al., "Diffusional Electrotitration: Generation of pH Gradients . . . " Analytical Chemistry, Mar. 1, 1995, pp. 820-828, vol. 67, No. 5.
Fodor et al., "Light-Directed, Spatially Addressable Parallel Chemical Synthesis" Science, Feb. 15, 1991, 767-773, vol. 251.
Gao et al., "In Situ Synthesis of Oligonucleotide Microarrays" Biopolymers Mar. 2004, pp. 579-596, vol. 73.
Ghindilis et al., "Immunosensors: Electrochemical Sensing and Other . . . " Biosensors & Bioelectronics 1998, pp. 113-131, vol. 13, No. 1, Elsevier Sciences S.A.
Greene et al., "Protective Groups in Organic Synthesis" Third Edition, Wiley-Interscience, 1999.
Guo, et al., "Direct Fluorescence Analysis of Genetic Polymorphisms by Hybridization with Oligonucleotide . . . " Nucl. Acids Res., 1994, pp. 5456-5465, vol. 22, No. 24.
Hacia "Resequencing and mutational analysis using oligonucleotide microarrays" Nature Genetics 21 Supp.: 42, (1999).
Hacia et al., "Applications of DNA Chips for Genomic Analysis" Mol. Psychiatry, Nov. 1998, pp. 483-492, vol. 3, No. 6.
Hammerich et al., "Organic Electrochemistry, an Introduction & Guide" ed. by Lund and Baizer, 3rd Edition, 1991 pp. 615-657 Marcel Dekker, Inc., NY.
Johnston, "Gene Chips: Array of Hope for Understanding Gene Regulation" Curr. Biology, Feb. 26, 1998, R171-R174, vol. 8.
Krotz et al., "Large-Scale Synthesis of Antisense Oligonucleotides Without Chlorinated Solvents" Organic Process Res & Dev, 2000, pp. 190-193, vol. 4.
Kurian et al., "DNA Chip Technology" J. Pathology, 1999, pp. 267-271, vol. 187.
Lane et al., "Electrochemistry of Chemisorbed Molecules . . . " J. Physical Chemistry, 1973, pp. 1411-1421, vol. 77, No. 11 ($1^{st}$ Page Only).
Leproust et al., "Characterization of Oligodeoxyribonucleotide Synthesis on Glass Plates" Nucl. Acids Res., 2001, pp. 2171-2180, vol. 29, No. 10 (Abstract Only).
Lipkowski, et al., "Molecular Adsorption at Metal Electrodes" Electrochimica Acta, 1994, pp. 1045-1056, vol. 39, No. 8/9.
Maskos and Southern, "Oligodeoxyribonucleotide Synthesis on Glass Plates", Nucl. Acids Res., 1992, pp. 1679-1684, vol. 20.
Moller et al.. "Anodic oxidation of cyclohexene: Dependence of the product distribution on the reaction variables" Electrochimica Acta, vol. 42, No. 13, Jan. 1, 1997, pp. 1971-1978.
Ono et al., "Nucleosides and Nucleotides. 121. Synthesis of Oligonucleotides . . . " Bioconjugate Chem. 1993, pp. 499-508, vol. 4.
Patolsky et al. "Highly Sensitive Amplified Electronic Detection of DNA . . . " Chem. Eur. J., 2003, pp. 1137-1145, vol. 9, No. 5 Wiley-VCH Weinheim.
Patolsky et al., "Enzyme-Linked Amplified Electrochemical Sensing . . . " Langmuir 1999, vol. 15, No. 1,1 pp. 3703-3706, Am. Chemical Society.

Paul et al., "Acid Binding and Detritylation During Oligonucleotide Synthesis" Nucleic Acids Research, 1996, 3048-3052, vol. 24, No. 15.
Pellois et al.,"Peptide Synthesis Based on t-Boc Chemistry & Solution Photogenerated Acids" J. Comb. Chem. 2000, pp. 355-360, vol. 2, No. 4.
Pillai, "Photoremovable Protecting Groups in Organic Chemistry" Synthesis 1980, pp. 1-26, vol. 39.
Ronlan, A. and Parker, V. D., "Anodic oxidation of phenolic compounds. Part II. Products and mechanisms of the anodic oxidation of hindered phenols" J. Chem. Soc. (C), 1971, pp. 3214-3218.
Rossier et al., "Enzyme Linked lmmunsorbent Assay on a Microchip . . . " Lab on a Chip 2001, vol. 1, pp. 153-157, The Royal Society of Chemistry.
Septak, M. "Kinetic Studies on Depurination and Detritylation of CPG-bound Intermediates . . . " Nucleic Acids Research, 1996, pp. 3053-3058, vol. 24, No. 15.
Shchepinov et al., "Steric Factors Influencing Hybridisation of Nucleic Acids to Oligonucleotide Arrays" Nucl., Acids Res., 1997, pp. 115-1161, vol. 25, No. 6.
Shchepinov, M.S., "Oligonucleotide Dendrimers: From Poly-Labeled DNAc617 Probes to Stable Nano-Structures" Glen Report, Dec. 1999, vol. 12, No. 1.
Soriaga et al., "Determination of Orientation of Adsorbed Molecules . . . ", J. Am. Chem. Soc., 1982, pp. 3937-3945, vol. 104 ($1^{st}$ Page Only).
Stickney et al., "A Survey of Factors Influencing the Stablity of . . . " J. Electroanaly. Chem., 1981, pp. 73-88, vol. 125 (Abstract Only).
Wang, G. et al., "Synthesis of Oligonucleotides Containing . . . " Tetrahedron Letters, 1993, 6721-6724, vol. 34, No. 42, Great Britain.
Wang et al., "Dual Enzyme Electrochemical Coding for Detecting DNA Hybridization" Analyst 2002, 1279-1282, The Royal Society of Chemistry.
Wang, Joseph "Survey and Summary from DNA Biosensors . . . " Nucleic Acids Research 2000, pp. 3011-3016, vol. 28, No. 16 Oxford University Press.
Wilgenbus and Lichter, "DNA Chip Technology Ante Portas" J. Mol. Med., Nov. 1999, pp. 761-768, vol. 77.
Wu and Chen, J. Mater. Chem., 1997, 7(8), pp. 1409-1413.
Xie et al., Amperometric Detection of Nucleic Acid at Femtomolar Levels with a Nucleic Acid/Electrochemical Activator Bilayer on Gold Electrodes, 2004, vol. 76, pp. 1611-1617.
ISR, Application No. 05849631.6 PCT/US2005/041906, May 24, 2007, 4 pages.
Extended European Search Report, Application No. 05849631.6 PCT/US2005/041906, dated Sep. 23, 2010, 9 pages.
Rule 71(3) EPC European Communication, Application No. 05849631.6 PCT/US2005/041906, dated Jul. 23, 2018, 11 pages.
Communication from the examining division, Application No. 06739757.0 PCT/US2006/011150, dated Dec. 11, 2015, 29 pages.
Bakker E (2004) Electrochemical sensors. Anal Chem 76: 3285-3298.
Batchelor-McAuley, C.; Wildgoose, G. G.; Compton, R. G. The physicochemical aspects of DNA sensing using electrochemical methods. Biosens. Bioelectron. 2009, 24, 3183-3190.
Caillat, P.; David, D.; Belleville, M.; Clerc, F.; Massit, C.; Revol-Cavalier, F.; Peltie, P.; Livache, T.; Bidan, G.; Roget, A.; Crapez, E. Biochips on CMOS: An active matrix address array for DNA analysis. Sens. Actuat. B: Chem. 1999, 61, 154-162.
Chen, C.; Nagy, G.; Walker, A. V.; Maurer, K.; McShea, A.; Moeller, K. D. Building addressable libraries: The use of a mass spectrometry cleavable linker for monitoring reactions on a microelectrode array. J. Am. Chem. Soc. 2006, 128, 16020-16021.
Cosnier S (1999) Biomolecule immobilization on electrode surfaces by entrapment or attachment to electrochemically polymerized films. A review. Biosensors & Bioelectronics 14: 443-456.
Cuzin, M. DNA chips: A new tool for genetic analysis and diagnostics. Transfus. Clin. Biol. 2001, 8, 291-296.
Daniels, J. S.; Pourmand, N. Label-free impedance biosensors: opportunities and challenges. Electroanalysis 2007, 19, 1239-1257.

(56) References Cited

OTHER PUBLICATIONS

De Giglio, E.; Sabbatini, L.; Zambonin, P. G. Development and analytical characterization of cysteine-grafted polypyrrole films electrosynthesized on Pt- and Ti-substrates as precursors of bioactive interfaces. J. Biomater. Sci. Polym. Ed. 1999, 10, 845-858.

Diaz-Gonzales M, Gonzalez-Garcia M B, Costa-Garcia A (2005) Recent advances in electrochemical enzyme immunoassays. Electroanalysis 17: 1901-1918.

Dill K, Montgomery D D, Ghindilis A L, Schwarzkopf K R, Ragsdale S R, et al. (2004) Immunoassays based on electrochemical detection using microelectrode arrays. Biosensors & Bioelectronics 20: 736-742.

Galandoava, J.; Labuda, J. Polymer interfaces used in electrochemical DNA-based biosensors. Chem. Pap. 2009, 63, 1-14.

Gambhir, A.; Gerard, M.; Jain, S. K.; Malhotra, B. D. Characterization of DNA immobilized on electrochemically prepared conducting polypyrrole-polyvinyl sulfonate films. Appl. Biochem. Biotechnol. 2001, 96, 303-309.

Ghindilis, A. L.; Smith, M. W.; Schwarzkopf, K. R.; Roth, K. M.; Peyvan, K.; Munro, S. B.; Lodes, M. J.; Stover, A. G.; Bernards, K.; Dill, K.; McShea, A. CombiMatrix oligonucleotide arrays: genotyping and gene expression assays employing electrochemical detection. Biosens. Bioelectron. 2007, 22, 1853-1860.

Labib M, Hedstrom M, Amin M, Mattiasson B (2009) A capacitive biosensor for detection of staphylococcal enterotoxin B. Anal Bioanal Chem 393: 1539-1544.

Livache, T.; Maillart, E.; Lassalle, N.; Mailley, P.; Corso, B.; Guedon, P.; Roget, A.; Levy, Y. Polypyrrole based DNA hybridization assays: study of label free detection processes versus fluorescence on microchips. J. Pharm. Biomed. Anal 2003, 32, 687-696.

Livache, T.; Fouque, B.; Roget, A.; Marchand, J.; Bidan, G.; Teoule, R.; Mathis, G. Polypyrrole DNA chip on a silicon device: example of hepatitis C virus genotyping. Anal. Biochem. 1998, 255, 188-194.

Livache, T.; Roget, A.; Dejean, E.; Barthet, C.; Bidan, G.; Teoule, R. Preparation of a DNA matrix via an electrochemically directed copolymerization of pyrrole and oligonucleotides bearing a pyrrole group. Nucleic. Acid. Res. 1994, 22, 2915-2921.

Minehan, D. S.; Marx, K. A.; Tripathy, S. K. Kinetics of DNA binding to electrically conducting polypyrrole films. Macromolecules 1994, 27, 777-783.

Minehan, D. S.; Marx, K. A.; Tripathy, S. K. DNA binding to electropolymerized polypyrrole: The dependence on film characteristics. J. Macromol. Sci. Part A: Pure Appl. Chem. 2001, 38, 1245-1258.

Palmisano F, Zambonin P G, Centoze D (2000) Amperometric biosensors based on electrosynthesised polymeric films. Fresenius Journal of Analytical Chemistry 366: 586-601.

Park, J. Y.; Park, S. M. DNA Hybridization sensors based on electrochemical impedance spectroscopy as a detection tool. Sensors 2009, 9, 9513-9532.

Peng, H.; Zhang, L.; Soeller, C.; Travas-Sejdic, J. Conducting polymers for electrochemical DNA sensing. Biomaterials 2009, 30, 2132-2148.

Rahman M A, Kumar P, Park D-S, Shim Y-B (2008) Electrochemical sensors based on organic conjugated polymers. Sensors 8: 118-141.

Ramanaviciene A, Ramanavicius A (2002) Application of polypyrrole for the creation of immunosensors. Critical Reviews in Analytical Chemistry 32: 245-252.

Ramanavicius A, Ramanaviciene A, Malinauskas A (2006) Electrochemical sensors based on conducting polymer-pyrrole. Electrochimica Acta 51: 6027-6037.

Ramanavicius, A.; Kurilcik, N.; Jursenas, S.; Finkelsteinas, A.; Ramanaviciene, A. Conducting polymer based fluorescence quenching as a new approach to increase the selectivity of immunosensors. Biosen. Bioelectron. 2007, 23, 499-505.

Roth, K. M.; Peyvan, K.; Schwarzkopf, K. R.; Ghindilis, A. Electrochemical detection of short dna oligomer hybridization using the combimatrix electrasense microarray reader. Electroanalysis 2006, 18, 1982-1988.

Sadik O A, Ngundi M, Wanekaya A (2003) Chemical biological sensors based on advances in conducting electroactive polymers. Microchimica Acta 143: 187-194.

Sadki S, Schottland P, Brodie N, Sabouraud G (2000) The mechanisms of pyrrole electropolymerization. Chemical Society Review 29: 283-293.

Song, X.; Wang, H. L.; Shi, J.; Park, J. W.; Swanson, B. I. Conjugated polymers as efficient fluorescence quenchers and their applications for bioassays. Chem. Mater. 2002, 14, 2342-2347.

Stuart, M.; Maurer, K.; Moeller, K. D. Moving known libraries to an addressable array: A site-selective hetero-Michael reaction. Bioconjug. Chem. 2008, 19, 1514-1517.

Tesfu, E.; Roth, K.; Maurer, K.; Moeller, K. D. Building addressable libraries: Site selective coumarin synthesis and the "real-time" signaling of antibody-coumarin binding. Org. Lett. 2006, 8, 709-712.

Trojanowicz M (2003) Application of conducting polymers in chemical analysis. Microchimica Acta 143: 75-91.

Vestergaard Md, Kerman K, Tamiya E (2007) An overview of label-free electrochemical protein sensors. Sensors 7: 3442-3458.

Vidal J-C, Garcia-Ruiz E, Castillo J-R (2003) Recent Advances in electropolymerized conducting polymers in amperometric biosensors. Microchimica Acta 143.

Zhang S, Wright G, Yang Y (2000) Materials and techniques for electrochemical biosensor design and construction. Biosensors & Bioelectronics 15: 273-282.

Zhou, Y.; Yu, B.; Guiseppi-Elie, A.; Sergeyev, V.; Levon, K. Potentiometric monitoring DNA hybridization. Biosens. Bioelectron. 2009, 24, 3275-3280.

Article 94(3) European Communication, Application No. 05849631.6 PCT/US2005/041906, dated Jan. 30, 2018, 4 pages.

Response to Article 94(3) European Communication, Application No. 05849631.6 PCT/US2005/041906, dated May 22, 2018, 3 pages.

Amended Claims filed in response to Article 94(3) European Communication, Application No. 05849631.6 , PCT/US2005/041906, dated May 22, 2018, 4 pages.

Amendment filed in response to Rule 115(1) EPC Communication, Application No. 06739757.0 PCT/US2006/011150, dated Dec. 18, 2018, 6 pages.

Auxiliary Request II Claims filed in response to Rule 115(1) EPC Communication, Application No. 06739757.0 PCT/US2006/011150, dated Dec. 18, 2018, 1 page.

Communication from the examining division, Application No. 06739757.0 PCT/US2006/011150, dated Jan. 11, 2019, 2 pages.

\* cited by examiner

HRP Reaction Scheme

Laccase System

Glucose Oxidase Reaction Scheme

PMS = 5-methyl-phenazinium methyl sulfate

SEQUENCE LISTING

```
<160> NUMBER OF SEQ ID NOS: 8

<210> SEQ ID NO 1
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 1
tacgcctcca gctcc                                                      15

<210> SEQ ID NO 2
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 2
aggctacgaa gactt                                                      15

<210> SEQ ID NO 3
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 3
ggagctggtg gcgta                                                      15

<210> SEQ ID NO 4
<211> LENGTH: 18
```

```
<212> TYPE: DNA
<213> ORGANISM: Artificial Sequence
<220> FEATURE:
<223> OTHER INFORMATION: Synthetic polynucleotide

<400> SEQUENCE: 4
aagtcttcgt cgtagcct                                              18

<210> SEQ ID NO 5
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 5

Tyr Gly Gly Phe
1

<210> SEQ ID NO 6
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 6

Gly Gly Phe Leu
1

<210> SEQ ID NO 7
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 7

Tyr Gly Gly Phe Leu
1               5

<210> SEQ ID NO 8
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 8

Gly Phe Leu
1
```

ENZYME-AMPLIFIED REDOX MICROARRAY DETECTION PROCESS

REFERENCE TO A "SEQUENCE LISTING," A TABLE, OR A COMPUTER PROGRAM LISTING APPENDIX SUBMITTED AS AN ASCII TEXT FILE

The Sequence Listing written in file CUST-01405U0-3_ST25.TXT, created Aug. 7, 2018, 1,664 bytes, machine format IBM-PC, MS-Windows operating system, is hereby incorporated by reference.

TECHNICAL FIELD OF THE INVENTION

The present invention provides a process and an array for assaying for binding of target molecules to capture molecules on micro array devices, wherein the microarray devices contain electrodes. Specifically, the present invention provides a binding (including nucleotide hybridization) process to detect binding on a micro array wherein the micro array contains electronically addressable electrode devices. The inventive detection process further provides for an enzymatically catalyzed oxidation/reduction reaction to take place within a "virtual flask" region of a micro array wherein the reaction is detected by current changes detected on the addressable electrode.

BACKGROUND OF THE INVENTION

In the world of micro arrays or biochips, biological molecules (e.g., oligonucleotides, polypeptides, oligopeptides and the like) are placed onto surfaces at defined locations for potential binding with target samples of nucleotides or receptors or other molecules. Microarrays are miniaturized arrays of biomolecules available or being developed on a variety of platforms. Much of the initial focus for these micro arrays have been in genomics with an emphasis of single nucleotide polymorphisms (SNPs) and genomic DNA detection/validation, functional genomics and proteomics (Wilgenbus and Lichter, 1. *Mol. Med.* 77:761, 1999; Ashfari et al., *Cancer Res.* 59:4759, 1999; Kurian et al., *J. Pathol.* 187:267, 1999; Hacia, *Nature Genetics* 21 suppl.:42, 1999; Hacia et al., *Mol. Psychiatry* 3:483, 1998; and Johnson, *Curr. Biol.* 26: RI71, 1998).

There are, in general, three categories of micro arrays (also called "biochips" and "DNA Arrays" and "Gene Chips" but this descriptive name has been attempted to be a trademark) having oligonucleotide content. Most often, the oligonucleotide micro arrays have a solid surface, usually silicon-based and most often a glass microscopic slide. Oligonucleotide micro arrays are often made by different techniques, including (1) "spotting" by depositing single nucleotides for in situ synthesis or completed oligonucleotides by physical means (ink jet printing and the like), (2) photolithographic techniques for in situ oligonucleotide synthesis (see, for example, Fodor U.S. patent '934 and the additional patents that claim priority from this priority document, (3) electrochemical in situ synthesis based upon pH based removal of blocking chemical functional groups (see, for example, Montgomery U.S. Pat. No. 6,093,302 the disclosure of which is incorporated by reference herein and Southern U.S. Pat. No. 5,667,667), and (4) electric field attraction/repulsion of fully-formed oligonucleotides (see, for example, Hollis et al., U.S. Pat. No. 35 5,653,939 and its duplicate Heller U.S. Pat. No. 5,929,208). Only the first three basic techniques can form oligonucleotides in situ that are, building each oligonucleotide, nucleotide-by-nucleotide, on the micro array surface without placing or attracting fully formed oligonucleotides.

With regard to placing fully-formed oligonucleotides at specific locations, various microspotting techniques using computer-controlled plotters or even ink-jet printers have been developed to spot oligonucleotides at defined locations. One technique loads glass fibers having multiple capillaries drilled through then with different oligonucleotides loaded into each capillary tube. Microarray chips, often simply glass microscope slides, are then stamped out much like a rubber stamp on each sheet of paper of glass slide. It is also possible to use "spotting" techniques\ to build oligonucleotides in situ. Essentially, this involves "spotting" relevant single nucleotides at the exact location or region on a slide (preferably a glass slide) where a particular sequence of oligonucleotide is to be built. Therefore, irrespective of whether or not fully-formed oligonucleotides or single nucleotides are added for in situ synthesis, spotting techniques involve the precise placement of materials at specific sites or regions using automated techniques.

Another technique involves a photolithography process involving photomasks to build oligonucleotides in situ, base-by-base, by providing a series of precise photomasks coordinated with single nucleotide bases having light-cleavable blocking groups. This technique is described in Fodor et al. U.S. Pat. No. 5,445,934 and it's various progeny patents. Essentially, this technique provides for "solid-phase chemistry, photolabile protecting groups, and photolithography . . . to achieve light-directed spatially-addressable parallel chemical synthesis." Binary masks are used in the preferred embodiment.

The electrochemistry platform (Montgomery U.S. Pat. No. 6,093,302, the disclosure of which is incorporated by reference herein) provides a micro array based upon a semiconductor chip platform having a plurality of micro electrodes. This chip design uses Complimentary Metal Oxide Semiconductor (CMOS) technology to create high-density arrays of microelectrodes with parallel addressing for selecting and controlling individual micro electrodes within the array. The electrodes turned on with current flow generate electrochemical reagents (particularly acidic protons) to alter the pH in a small defined "virtual flask" region or volume adjacent to the electrode. The micro array is coated with a porous matrix for a reaction layer material. Thickness and porosity of the material is carefully controlled and biomolecules are synthesized within volumes of the porous matrix whose pH has been altered through controlled diffusion of protons generated electrochemically and whose diffusion is limited by diffusion coefficients and the buffering capacities of solutions.

The micro array systems have detection processes generally using some form of photon based detection. That is, most detection processes use fluorescent probes (alternatively visible dyes or luminescent probes) attached to "target" DNA sequences to detect binding or hybridization to an oligonucleotide capture probe attached on a micro array. Depending upon the intensity of the signal, such micro arrays having probes to show hybridization have to be read through laser confocal microscope-based system for micro arrays configured in a monolayer (such as those micro arrays made through high density spotting or photolithography techniques) or by a video-type camera (such as a CCD camera) for those micro arrays having a three-dimensional matrix for each spot in high density formats. In each instance, there is often stray light or other noise signals that cause false readings to be made. Moreover, it occasionally becomes difficult to distinguish between shades of gray or barely perceptible signals as true positives or false positives. Therefore, there is a need in the art for improvements to the detection/reading process for analyzing microarrays. The present invention was made to address this need and to provide a detection system that can generate a more objective "yes" or "no" answer for each site in high density micro array detection.

SUMMARY OF THE INVENTION

The present invention provides a process for reading micro array devices having addressable electrodes to determine binding between a capture probe and a target molecule, comprising:

(a) providing an array having a plurality of electrodes and a plurality of capture molecules at sites corresponding to the electrodes;

(b) non-specifically attaching an oxidation/reduction enzyme moiety to one or a plurality of target molecules in a sample for analysis to create a prepped target sample;

(c) administering the prepped target sample to the array and allowing for binding of target molecules to capture molecules;

(d) adding a substrate to the array that will create a local voltage signal when catalyzed by the oxidation/reduction enzyme through local generation of electrochemical reagents; and (e) measuring for the presence or absence of a voltage or current signal generated locally by electrochemical reagents at each electrode having a capture molecule attached thereto.

Preferably, the array having a plurality of electrodes and capture molecules corresponding to the electrodes is generated by a technique selected from the group consisting of in situ synthesis with electrochemical techniques, spotting the capture molecules, ink-jet printing the capture molecules, and in situ synthesis through photolithography techniques. Most preferably, the array having a plurality of electrodes and capture molecules corresponding to the electrodes is formed by in situ synthesis with electrochemical techniques. Preferably, the oxidation/reduction enzyme is selected from the group consisting of laccase, horseradish peroxidase, β-galactosidase, glucose oxidase, alkaline phosphatase, dehydrogenases, and combinations thereof. Preferably, the oxidation/reduction enzyme is attached to the target molecule(s) through an antibody and anti-idiotype antibody combination or through a biotin and streptavidin (or avidin) binding combination. Preferably, the array having a plurality of electrodes further comprises a porous reaction layer covering the electrodes, wherein the porous reaction layer has a thickness of from about 0.1 microns to about 10 microns and whereby the porous reaction layer functions to block diffusion of oxidation/reduction activity products such that there is little lateral signal being picked up at an adjacent electrode. Most preferably, the porous reaction layer is made from a polymeric material selected from the group consisting of polyvinyl alcohol, polyvinyl acetate, dextran, epoxy-based polymers, tricellulose acetate, polyurethane, agarose, controlled porosity glass with a PTFE resin, and combinations thereof. Preferably, the capture molecule is a molecule from the class of molecules selected from the group consisting of oligonucleotides, polypeptides, antibodies, glycosylated polypeptides, polysaccharides, and mixed molecules having monomers from a plurality of the foregoing molecules. Similarly, the target molecule is one likely to bind to at least one of a plurality of capture molecules. Most preferably, a target molecule is from a class of molecules selected from the group consisting of DNA, RNA, single-stranded DNA, ribosomal RNA, mitochondrial DNA, cellular receptors (i.e., glycosylated or non-glycosylated membrane-bound proteins), polypeptides, glycosylated polypeptides, antibodies, cellular antigenic determinants, organic molecules, metal ions, salt anions and cations, and combinations thereof.

The present invention further provides a mircoarray device for detecting binding of a target molecule to a capture probe, comprising:

(a) an array having a plurality of electrodes and a plurality of capture molecules at sites corresponding to the electrodes;

(b) an oxidation/reduction enzymatic moiety bound to one or a plurality of target molecules in a sample for analysis, wherein the oxidation/reduction enzymatic moiety bound to the target molecules is incubated with the capture molecules on the array such that binding between capture molecules and target molecules that bind, will occur;

(c) a substrate molecule that will create a local voltage signal when catalyzed by the oxidation/reduction enzyme through local generation of electrochemical reagents; and (e) a voltage signal measuring device electrically connected to each electrode on the array.

Preferably, the array having a plurality of electrodes and capture molecules corresponding to the electrodes is generated by a technique selected from the group consisting of in situ synthesis with electrochemical techniques, spotting the capture molecules, ink-jet printing the capture molecules, and in situ synthesis through photolithography techniques. Most preferably, the array having a plurality of electrodes and capture molecules corresponding to the electrodes is formed by in situ synthesis with electrochemical techniques. Preferably, the oxidation/reduction enzyme is selected from the group consisting of laccase, horseradish peroxidase, β-galactosidase, glucose oxidase, alkaline phosphatase, dehydrogenases, and combinations thereof. Preferably, the oxidation/reduction enzyme is attached to the target molecule(s) through an antibody and antiidiotype antibody combination or through a biotin and streptavidin (or avidin) binding combination. Preferably, the array having a plurality of electrodes further comprises a porous reaction layer covering the electrodes, wherein the porous reaction layer has a thickness of from about 0.1 microns to about 10 microns and whereby the porous reaction layer functions to block diffusion of oxidation/reduction activity products such that there is little lateral signal being picked up at an adjacent electrode. Most preferably, the porous reaction layer is made from a polymeric material selected from the group consisting of polyvinyl alcohol, polyvinyl acetate, polyvinyl alcohol, tricellulose acetate, polyurethane, agarose, controlled porosity glass with a PTFE resin, dextran, epoxy-based polymers, and combinations thereof. Preferably, the capture molecule is a molecule from the class of molecules selected from the group consisting of oligonucleotides, polypeptides, antibodies, glycosylated polypeptides, polysaccharides, and mixed molecules having monomers from a plurality of the foregoing molecules. Similarly, the target molecule is one likely to bind to at least one of a plurality of capture molecules. Most preferably, a target molecule is from a class of molecules selected from the group consisting of DNA, RNA, single-stranded DNA, ribosomal RNA, mitochondrial DNA, cellular receptors (i.e., glycosylated or nonglycosylated membrane-bound proteins), polypeptides, glycosylated polypeptides, antibodies, cellular antigenic determinants, organic molecules, metal ions, salt anions and cations, and combinations thereof.

BRIEF DESCRIPTION OF THE DRAWINGS

FIG. 13 reverses the sign of current flow for better visualization.

FIG. 33*b* shows the electrode array after all of the electrodes in the array were exposed to the same voltage and deprotection occurred at each electrode in the array. A voltage of 2.8 volts was applied for 10 minutes. This photomicrograph was taken using a 4× objective and using a 1 second integration time.

FIG. 49a represents a top view showing a selected electrode having a "getter" structure 2 forming a substantial ring around the selected electrode. FIG. 49b represents a cross section of the same showing a selected electrode having a "getter" structure 2 forming a substantial ring around the selected electrode 1.

FIG. 50a represents a top view showing a selected electrode having a "getter" structure 2 forming a substantial ring around the selected electrode 1 and beneath the top surface of the selected electrode. FIG. 49b represents a cross section of the same showing a selected electrode having a "getter" structure 2 forming a substantial ring around the selected electrode 1. The "getter" structure is placed beneath the external surface of the insulating dielectric 3 in this configuration.

DETAILED DESCRIPTION OF THE INVENTION

Figure 1:
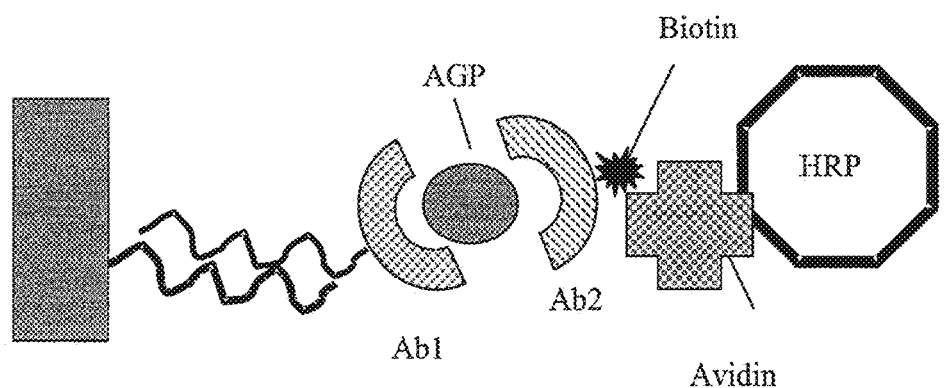
FIG. 1 shows the chemical reaction scheme when using horseradish peroxidase (HRP) as the oxidation/reduction enzyme. Specifically, the targeted molecule is AGP (α-1 acid glycoprotein) that has been complexed with HRP by adding a biotin-labeled antibody specific for an epitope of AGP. The target molecule is complexed with HRP by adding an avidin-labeled HRP enzyme. The microarray site used for detecting AGP as the target molecule has another antibody binding to a different epitope on AGP as the capture molecule. Moreover, the first antibody (labeled "Ab 1") is self assembled to an oligonucleotide microarray through a tag array capture probe.

There is disclosed a process for reading micro array devices having addressable electrodes to determine binding between a capture probe and a target molecule, comprising:

(a) providing an array having a plurality of electrodes and a plurality of capture molecules at sites corresponding to the electrodes;

(b) non-specifically attaching an oxidation/reduction enzymatic moiety to one or a plurality of target molecules in a sample for analysis to create a prepped target sample;

(c) administering the prepped target sample to the array and allowing for binding of target molecules to capture molecules;

(d) adding a substrate to the array that will create a local voltage signal when catalyzed by the oxidation/reduction enzyme through local generation of electrochemical reagents; and (e) measuring for the presence or absence of a voltage signal generated locally by electrochemical reagents at each electrode having a capture molecule attached thereto.

Electrode-Based Microarrays

Electrode-based micro arrays can be made with various oligomers attached to predefined regions, wherein each predefined region is defined by the presence of an addressable electrode. An addressable electrode is one where it can be electronically accessed to create a current or voltage. Electrode-based micro arrays further and often comprise a porous matrix layer that holds the capture molecules and provides a three dimensional virtual flask (cylindrical in the case of a circular electrode). In a preferred embodiment, the porous matrix layer is a membrane, wherein the membrane material is selected from the group consisting of polyvinyl alcohol, polyvinyl acetate, polyvinyl alcohol, tricellulose acetate, polyurethane, agarose, controlled porosity glass with a PTFE resin, and combinations thereof. In each case, the micro array, contains a plurality (or in rare cases only one) of capture molecules. In the most common form of micro array, the capture molecules are oligonucleotides than can bind to complementary sequence regions (or nearly complementary sequence regions depending upon the hybridization conditions) of DNA or mRNA from the target samples. The challenge next becomes how one can detect this binding event or hybridization event. In terms of marketed products, that are generally made by spotting or ink-jet printing oligonucleotides onto planar, non-porous surfaces such as glass slides, there are sample labeling kits commercially available that cause the sample nucleic acid to become labeled with a fluorescent dye. Often it is a fluorescent dye sold under the trademarks of Texas Red®, or Cy® Dyes Cy3 and Cy5. The microarray is "read" through a common fluorometer arrangement with either microscopic magnification or imaging stitching and looking for fluorescence at the known locations where the capture molecule was spotted or synthesized. This common technique of fluorescent detection of micro arrays using a standard fluorometer configuration with a micro array is the detection method universally used. However, there are optics issues, difficulty in labeling with fluorescent dyes, occasional high background problems and most importantly, extremely high costs associated with fluorescent microscopic equipment. Therefore, there is a need to detect molecular binding on micro arrays using lower cost equipment. The present inventive method uses electrochemical reagents generated locally within a porous reaction layer or membrane to only locally provide current or voltage to a nearby electrode, whose current or voltage signal can be detected at the nearby electrode and not "cross-talk" onto neighboring electrodes.

Immunoassays

Figure 2:
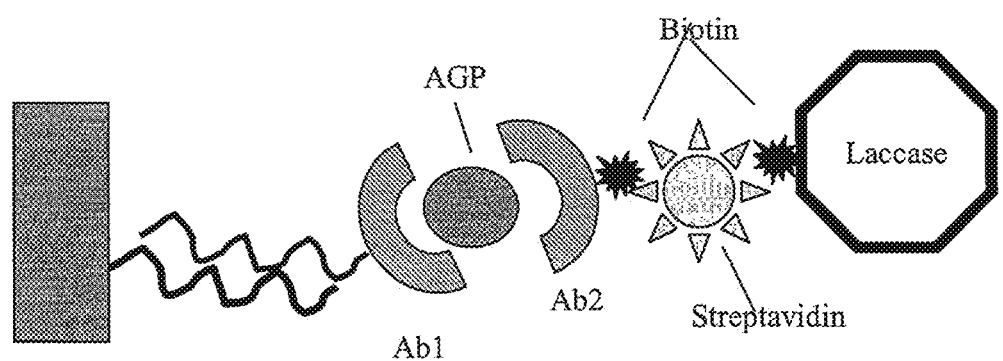
FIG. 2 shows a similar configuration for detecting AGP as a known site on a microarray, except this complex uses the multimeric nature of streptavidin to capture both biotin-labeled second antibody bound to a second epitope on AGP and biotin-labeled different oxidation/reduction enzyme laccase.

Immunoassays are based generally upon antibody binding to another molecule, generally a protein sugar or glycoprotein. The problems of immunoassays are generally detection of this binding event. The sandwich based immunoassays are based upon the fact that one antibody has already been attached to the surface of the chip (the capture antibody; most often a monoclonal). The analyte is then bound to the antibody and a second antibody (usually polyclonal) is added for use as a reporter group. The second reporter antibody will generally contain a fluorophore or have an enzyme covalently attached. Alternatively, the reporter antibody may contain a biotin molecule. To this biotin molecule, a streptavidin-enzyme conjugate can be an attached. Therefore, the inventive process can be constructed with immunoassays, even sandwich-type immunoassays by providing for the oxidation/reduction enzyme to be attached to a complex formed when binding to a capture molecule (i.e., first antibody) occurs. The latter assay formats allows a host of generic assay format to be designed without performing the grueling task of providing (synthesizing) analyte-based individual antibody-enzyme conjugates. Examples of immunoassays in a sandwich configuration are shown in FIGS. 1 and 2.

Oxidation/Reduction Enzyme Systems

Four different oxidation/reduction enzyme systems are exemplified herein. Each has different potential settings, each function in a unique pH range, they may require redox mediators and lastly, the substrate conditions vary. Reactions schemes are provided for each system.

Figure 5:
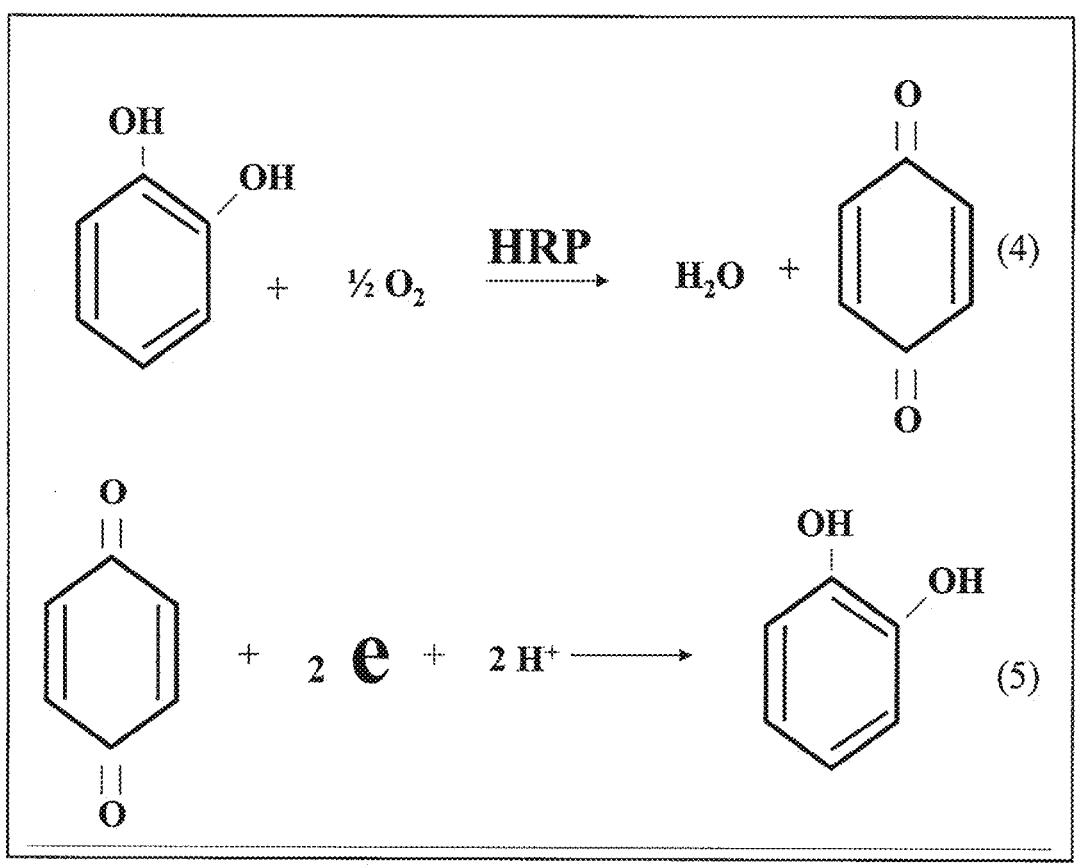
FIG. 5 shows a reaction scheme with HRP (horse radish peroxidase) as the oxidation/reduction enzyme and catechol as the substrate.

The HRP (horse radish peroxidase) reaction scheme with catechol as the substrate is shown in FIG. 5.

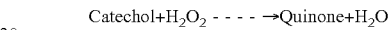

Catechol+$H_2O_2$ - - - - →Quinone+$H_2O$

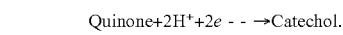

Quinone+$2H^+$+$2e$ - - →Catechol.

In a first assay, the product (quinone) was detected amperometrically. The first assay was performed at −0.3 V versus Pt wire in 0.05 M Na-citrate-phosphate buffer pH 5.0 containing 0.2M $Na_2SO_4$. Catechol and Hydrogen peroxide in 1 mM concentration were used as an enzymatic substrate. A proper checkerboard pattern from the micro array showed that binding occurred at the proper locations without the presence of noise or cross-talk bleeding over to neighboring electrode locations.

A second assay was performed at −0.3 V vs. Pt wire in 0.05 M Na-citrate-phosphate buffer pH 5.0 containing 0.2 M $Na_2SO_4$. Catechol in 1 mM concentration was used as an enzymatic substrate. This reaction scheme also produced the expected binding results and followed the reaction scheme as follows:

Catechol+$O_2$ - - - - →Quinone+$H_2O$

The product (quinone) was detected amperometrically:

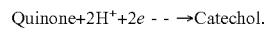

Figure 3:
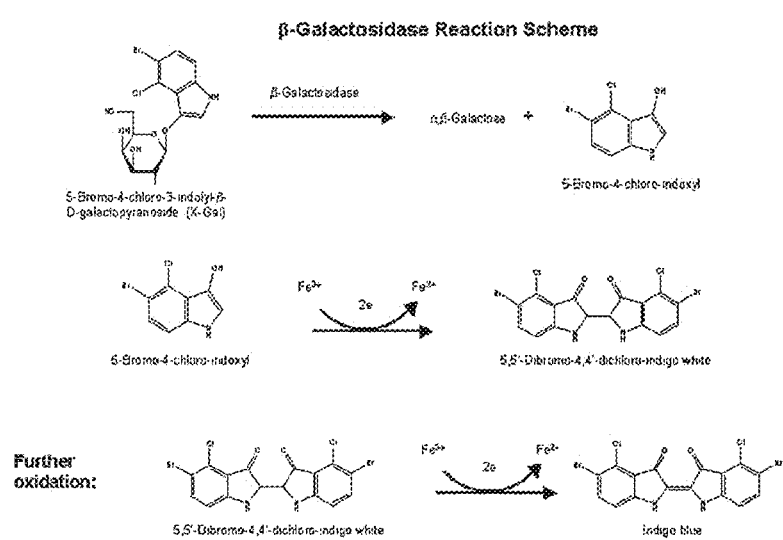
FIG. 3 shows the chemistry of the oxidation/reduction reaction when β-galactosidase is the oxidation/reduction enzyme and X-Gal (5-bromo-4-chloro-3-indoyl-β-D-galactopyranoside) is the substrate. The reaction forms indigo blue and generates electrochemical reactants. Preferably, the reaction is carried out at about pH 7.0 in 0.01 M phosphate buffer (PBS) with 1 mM $Fe^{2+}/Fe^{3+}$. The X-Gal should be present in saturation amounts.

Quinone+$2H^+$+$2e$ - - →Catechol.

β-Galactosidase reaction cleaves penultimate β-galactose residues from oligo saccharides or from glycosyl derivatives. The reaction scheme is shown in FIG. 3. The substrate used was X-Gal, which is an indolyl derivative of β-galactopyranoside. Biotinylated β-galactosidase was purchased for studies. The reactions were carried out at pH 7.0 in PBS buffer, 0.01 M. A given quantity of X-Gal was dissolved in DMF (very soluble) so that when it was added to the aqueous buffer, a substrate concentration of about 0.1 mM was achieved (saturation). The X-Gal/DMF solution was added while vigorously vortexing the aqueous phase because of the limited solubility of the X-Gal water. If the DMF/X-Gal solution is added without vigorous vortexing, the X-Ga would precipitate from solution. The instability of this solution requires that a fresh solution needs to be prepared daily.

Alternatively, an organic substrate (such as catechol) can be used. The turnover rate for this enzyme is lower than that for other redox enzymes, but the enzyme is very stable at neutral pH.

The X-Gal in itself does not interact well with glass or metal electrodes. Thus, an electron mediator is needed to shuttle electrons to the electrode surface. One such mediator is a ferri/ferrocyanide (50/50) solution. For example, a ferri/ferro cyanide solution can be used at about a 10 mM concentration when using an amperometric reaction and higher or lower concentrations for potentiometric reactions or increasing proportionately with the concentration of the added substrate. The voltage settings used in these experiments were 0 Volts (platinum electrode) and 0.5 V for the chip.

Figure 4:
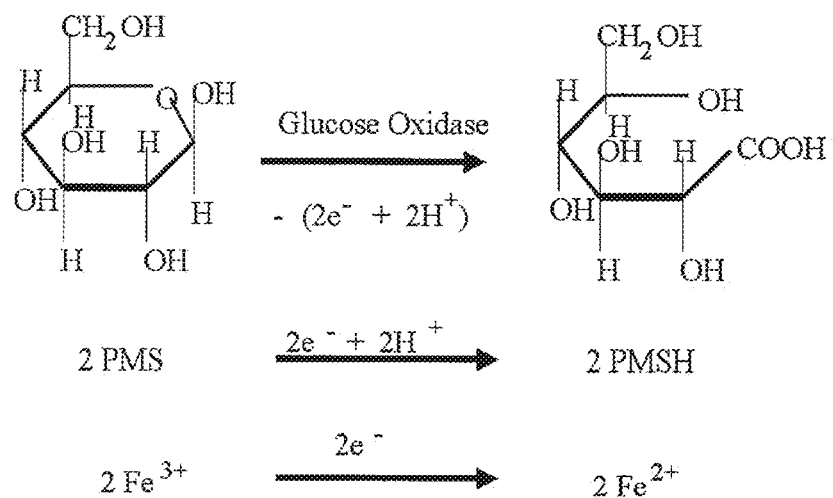
FIG. 4 shows the chemical reaction scheme when using glucose oxidase as the enzyme for oxidation reduction. Electrochemical reagents are generated with PMS (5-methyl-*phenazinium* methyl sulfate) as the substrate.

The Glucose Oxidase reaction scheme is shown on FIG. 4. Preferably, the reaction takes place at about pH 7.5 in a buffer, such as 0.1 M PBS buffer. The substrate was glucose and it is extremely soluble in water. The enzyme was regenerated with PMS (5-methyl-*phenazinium* methyl sulfate), which in turn utilizes the ferro/ferri cyanide shuttle for detection. The potential in this case had the platinum electrode set to 0 V and the chip electrode set to 0.5 V.

β-Galactosidase Results

Figure 6:
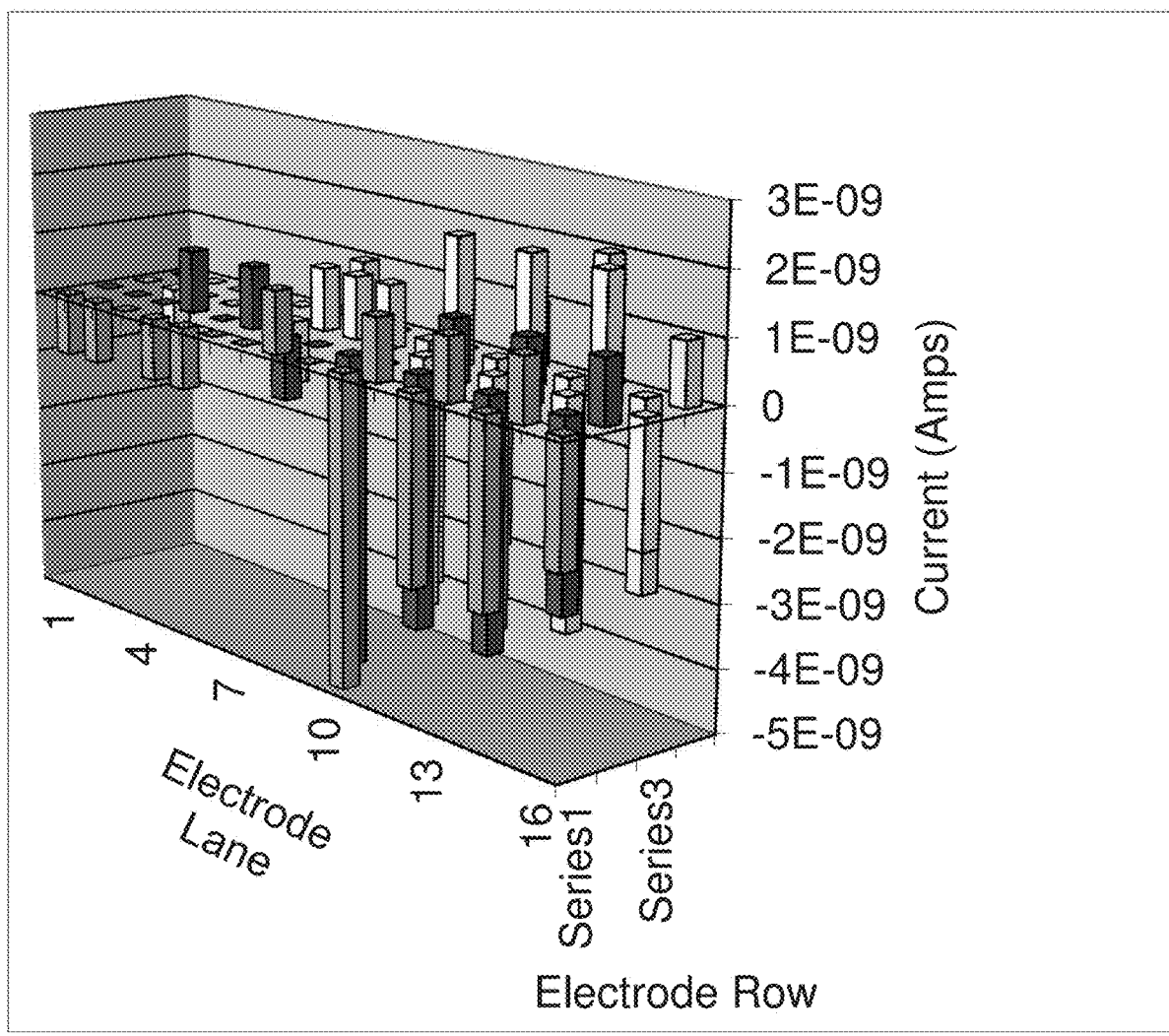
FIG. 6 shows a 3D plot of the amperometric measurement of β-galactosidase in an immunoassay detection system. Microarray chips were electrochemically modified with a biotin-containing reagent. In one section of the chip represented by lanes 1-8, no biotin tag was placed. In lanes 9-16, biotinylated-galactosidase was bound using a biotin-streptavidin-biotin complex. Redox reagents and substrates were added according to the reaction scheme in FIG. 3. These data show an amperometric response difference in the two parts of the chip, that is, lanes 1-8 versus lanes 9-16 containing β-galactosidase.
Figure 7:
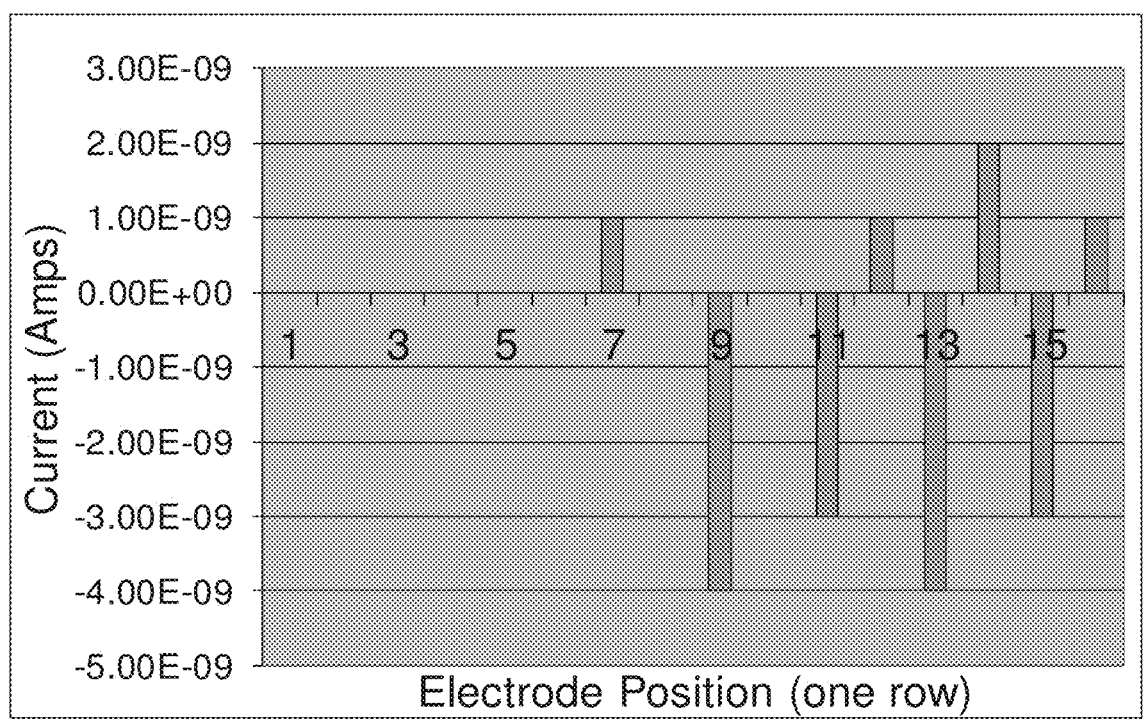
FIG. 7 shows a chip profile plot taken from a slice or row of the 3D plot from FIG. 6, wherein electrodes 9, 11, 13 and 15 contain β-galactosidase (bound in the region above the electrodes) and register a negative electrochemical signal. Therefore there is a positive result through the inventive electrochemical detection process at spots 9, 11, 13 and 15.

Results for beta-galactosidase immunoassay detection system are shown in FIG. 6. Microarray chips were electrochemically modified with a biotin-containing reagent. In one section of the chip represented by lanes 1-8, no biotin tag was placed. In lanes 9-16, biotinylated β-galactosidase was bound using a biotin-streptavidin-biotin complex. Redox reagents and substrates were added according to the reaction scheme in FIG. 3. These data show an amperometric response difference in the two parts of the chip, that is, lanes 1-8 versus lanes 9-16 containing β-galactosidase. FIG. 6 shows a 3D plot of the amperometric reaction with betagalactosidase. The negative values on this plot indicate that β-galactosidase is bound. The neighboring electrodes are used as counter electrodes in the synthesis process and do not contain any affinity tags. Similarly, FIG. 7 shows this chip profile as a slice (row) of the 3D plot shown in FIG. 6. Electrodes 9, 11, 13, and 15 contain beta-galactosidase.

Figure 8:
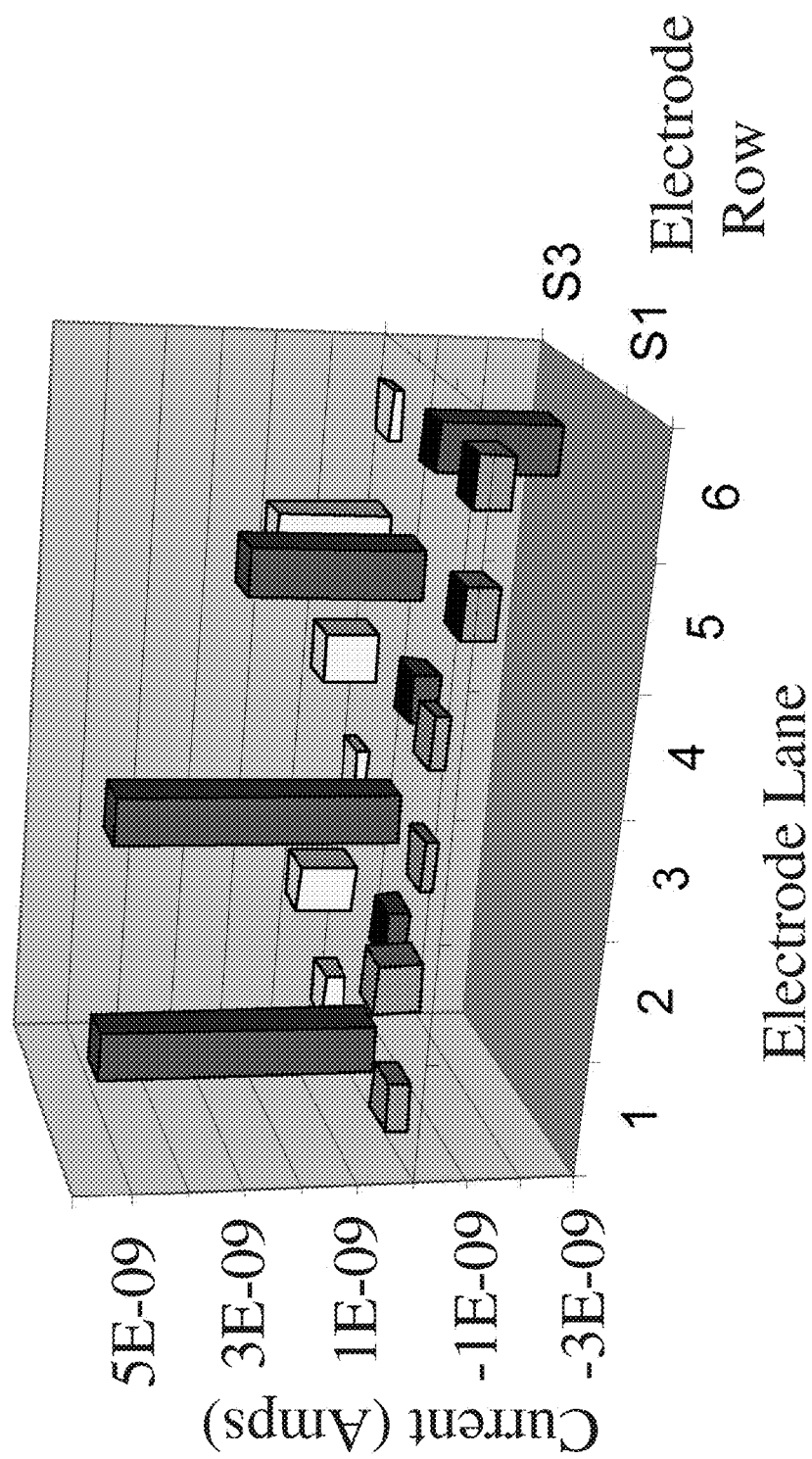
FIG. 8 shows binding and detection of a fluorescein-labeled β-galactosidase using an amperometric technique showing redox detection results. The fluorescein acted as a low molecular weight antigen attached to the larger enzyme. The oxidation/reduction enzyme capture was made possible by placement of an affinity-tagged anti-fluorescein antibody on alternating electrodes in row S2. These data show that those known locations associated with electrodes having fluorescein-labeled β-galactosidase showed enhanced signals. Moreover, these data were verified using epi-fluorescent microscopy to confirm the electrochemical results.

In yet another reaction and immunochemical detection, a capture and detection of fluorescein-containing beta-galactosidase was performed. An anti-fluorescein antibody containing an affinity tag was captured in row two of a biochip made by an in situ synthesis electrochemical process (Combimatrix Corporation, Mukilteo, Wash.). The fluorescein acted as a low molecular weight antigen attached to the larger enzyme. The redox detection results are shown in FIG. 8. The electrode sites containing the F-β-galactosidase showed an enhanced value. The binding of F-β-galactosidase to the membrane above the respective electrodes was corroborated and confirmed using the epi-fluorescent microscope. These data exactly track the results obtained with the inventive process of detecting current flow at the electrode. In FIG. 8, capture was made possible by the placement of an affinity tagged anti-F antibody on alternate electrodes in row S2.

Glucose-Oxidase Electrochemical Detection

Figure 9:
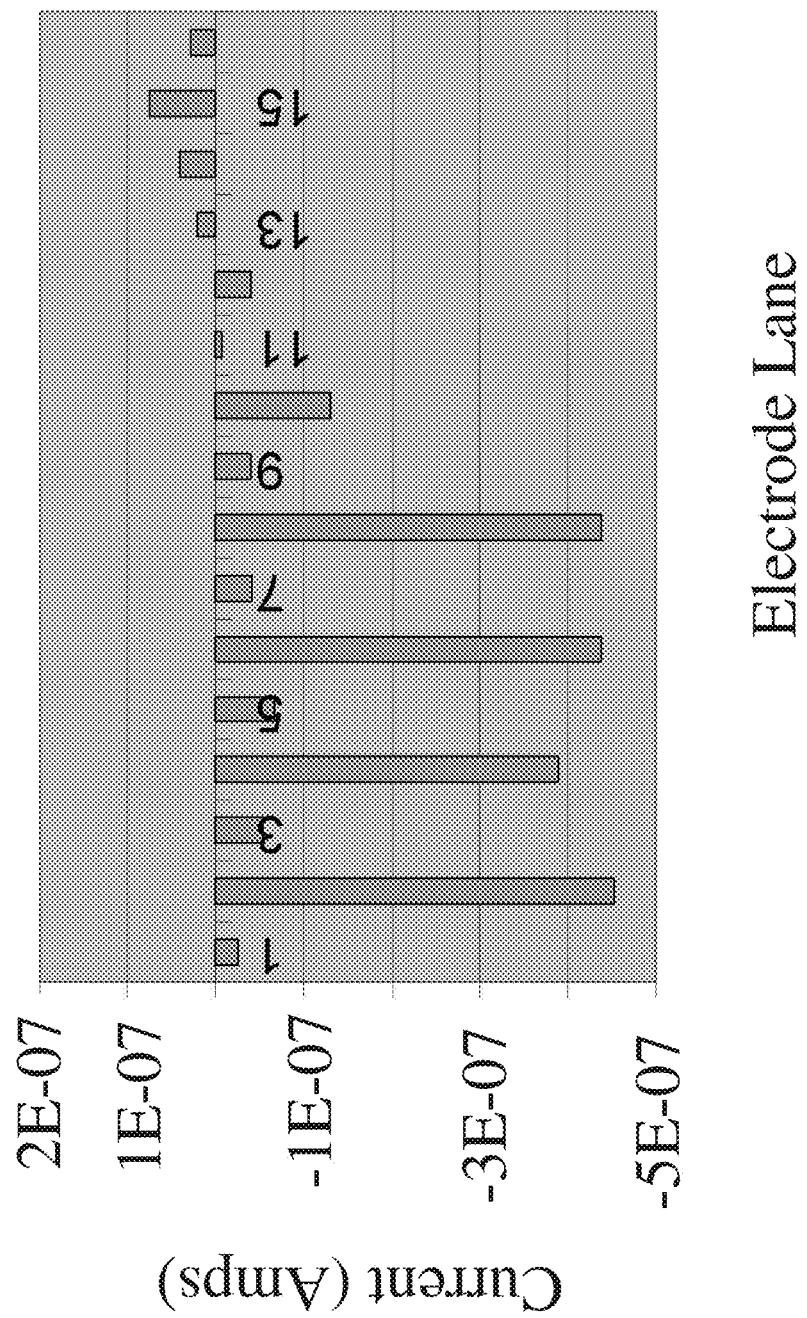
FIG. 9 shows a slice of a 3D plot created for the capture and detection of glucose oxidase as the oxidation/reduction enzyme. The glucose oxidase specific affinity tags are located in lanes 1-8. The glucose oxidase systems had higher background signals than other oxidation/reduction enzymes.

The glucose oxidase enzymatic reaction has some advantages and drawbacks relative to beta-galactosidase enzymatic reaction. The advantages are that all components of this reaction are extremely soluble in aqueous buffer. However, an electron mediator is required, such as PMS. PMS tends to "air oxidize" over time and must be made up freshly or stored under appropriate inert conditions or it will give a higher background signal. In an example of an assay performed with glucose oxidase, biotin was attached to glucose oxidase. The enzyme was then captured on the upper portion of the chip containing streptavidin (FIG. 9). As with β-galactosidase above, the chip contained biotin. Electrodes 1-8 contained a first affinity tag (e.g., biotin) and electrodes 9-16 contained a second affinity tag (e.g., streptavidin). The biotin complex allows the capture and detection of the enzyme system. FIG. 9 shows a slice of a 3D plot created for the capture and detection of glucose oxidase. The glucose oxidase specific affinity tags are located in lanes 1-8.

Horse Radish Peroxidase Detection

HRP is a redox enzyme that catalyses the reduction of peroxide. The enzyme is small (~36 kD) and the enzyme turnover is large. However, peroxide may damage certain polymeric porous matrices or membranes.

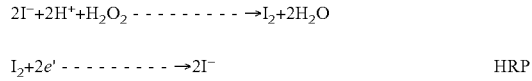

$$2I^- + 2H^+ + H_2O_2 \longrightarrow I_2 + 2H_2O$$

$$I_2 + 2e^- \longrightarrow 2I^- \qquad \text{HRP}$$

Figure 10:
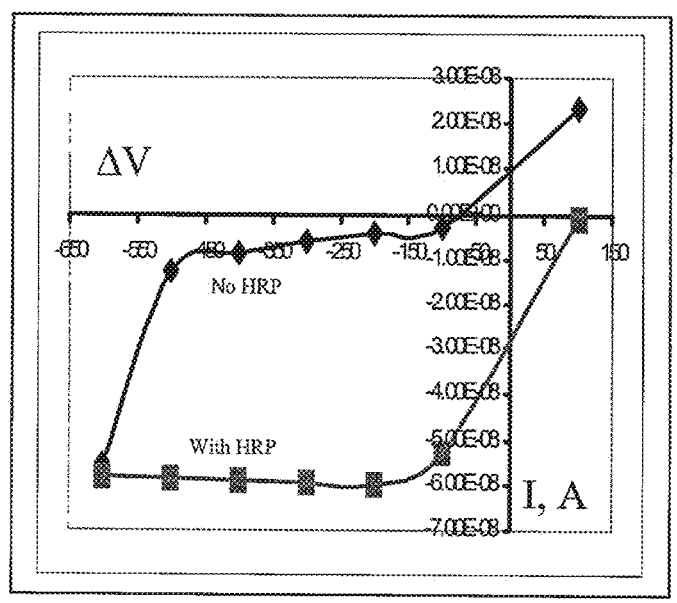
FIG. 10 shows a plot of a voltage versus current display for HRP (horse radish peroxidase) as a redox curve monitored by a single 100 micron diameter electrode on a bare (i.e., no in situ synthesis of biomolecules) microarray chip. The cyclic voltmogram-like results indicate at a negative potential and the amperometric difference (with and without enzyme) was substantial.
Figure 11:
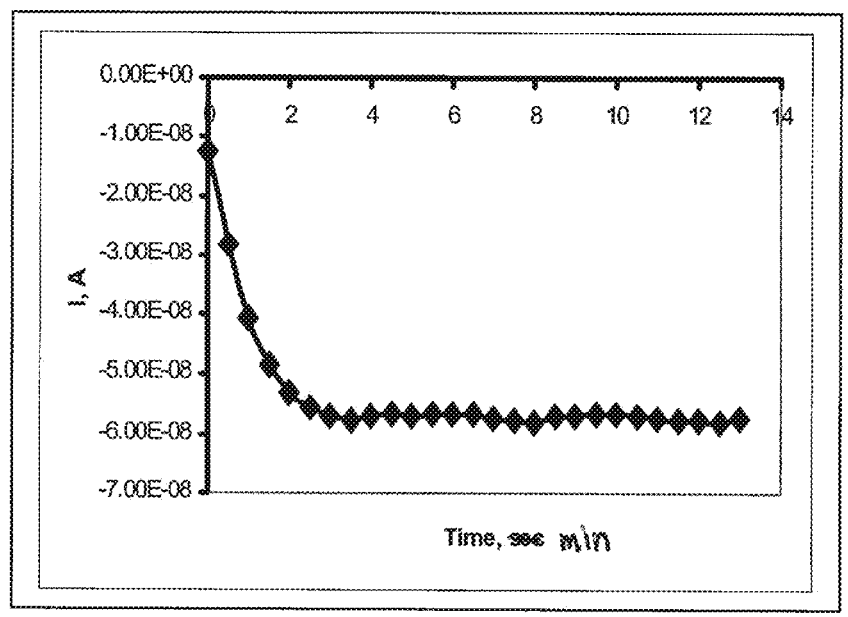
FIG. 11 shows the data from FIG. 10 in an amperometric experiment performed over a time course in a plot of current versus time for the peroxidase reaction. It should be noted that the current flow levels off after a period of a few minutes.

The redox curve for the peroxidase reaction was monitored by a single 100 micron diameter electrode on a bare (i.e., no porous membrane or capture molecules synthesized thereon) electrode-containing micro array device and is shown in FIG. 10. The cyclic voltamogram like results indicate at a negative potential, the amperometric difference with and without HRP enzyme was substantial. Taking these data, an amperometric experiment was performed over a period of time (FIG. 11). It should be noted that the current flow leveled off after a period of time. Thus, the best time to begin these studies after about 2 minutes (FIG. 11).

Figure 12:
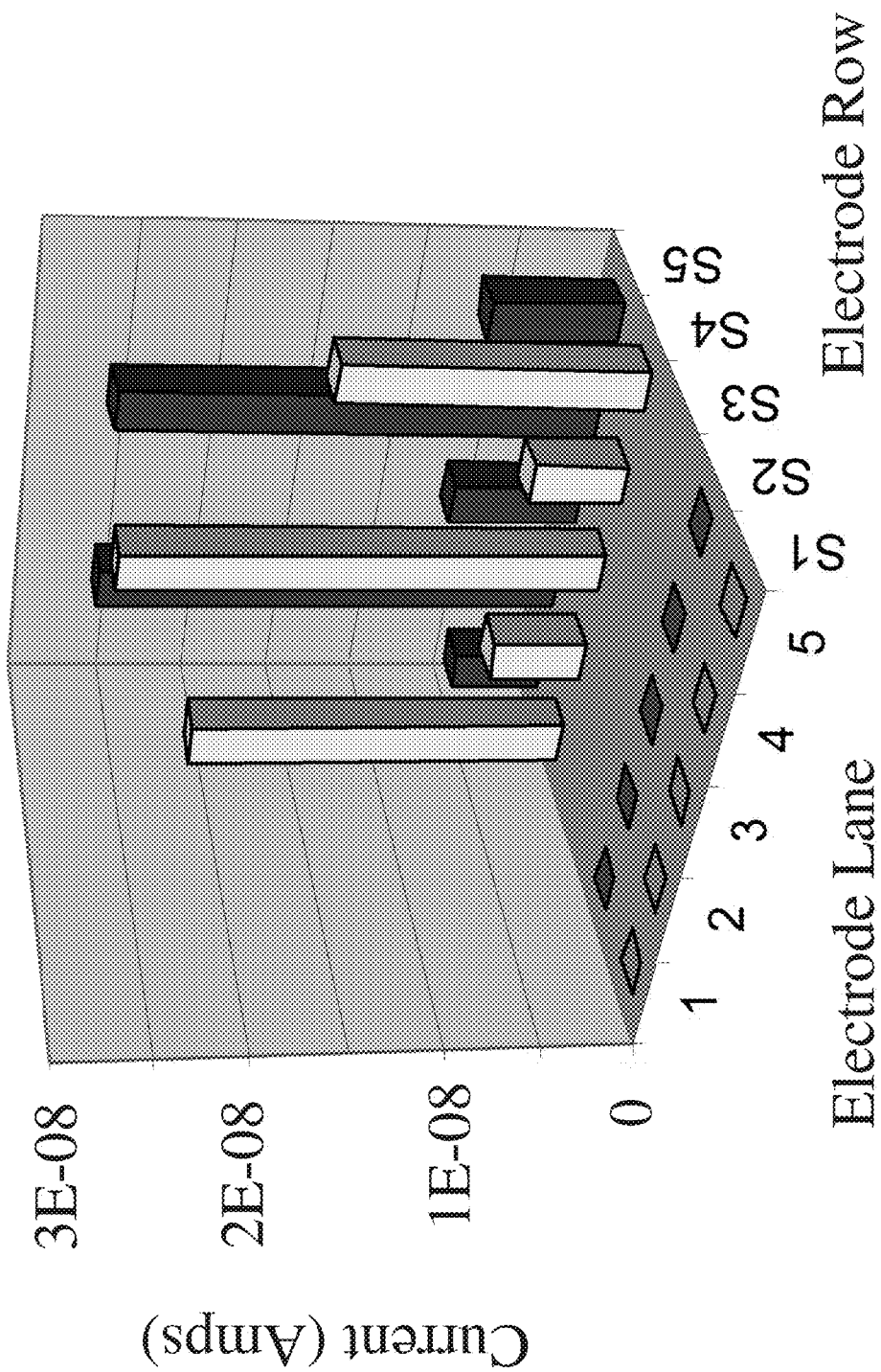
FIG. 12 shows an amperometric 3D plot for rabbit IgG bound to electrodes in S4 (1, 3 and 5) and in S5 (2 and 4) through oligonucleotide tagging. Rabbit IgG was detected by a complex of goat anti-rabbit polyclonal antibody conjugated with HRP oxidation/reduction enzyme. These data are consistent with other data showing that many enzymes function for electrochemical detection.
Figure 13:
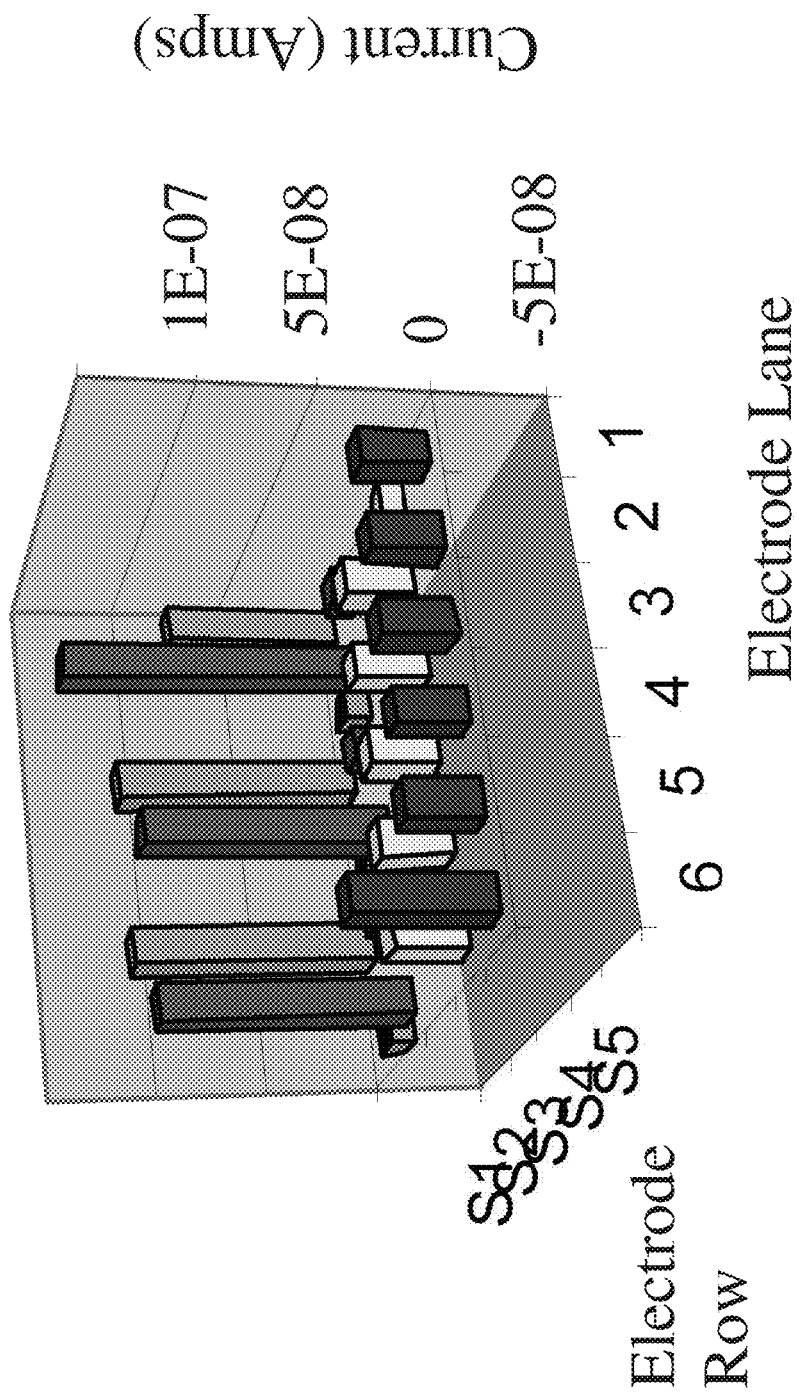
FIG. 13 shows a similar plot of goat IgG bound to electrodes S 1 (1, 3 and 5) and S2 (2, 4 and 6) through oligonucleotide tagging. Detection of goat IgG was made by a complex of mouse anti-goat monoclonal antibody conjugated with HRP.

For the peroxidase system, we have undertaken some initial experiments involving immunoassays. Rabbit IgG or goat IgG were affinity tagged and bound to the upper section and lower section of the membrane, respectively. Detection was made possible using HRP-tagged goat anti-rabbit Ab or HRP-tagged mouse monoclonal anti-goat antibodies. The results of these experiments are shown in FIGS. 12 and 13. Specifically, FIG. 12 shows amperometric detection of rabbit IgG bound to selected electrodes on a microarray biochip containing electrodes and a polyvinyl alcohol porous matrix (Combimatrix Corporation, Mukilteo, Wash.). HRP-tagged goat anti-Rb was used for the electrochemical detection. Samples are in S4 (1, 3, 5) and S5 (2, 4). The sign of the current flow has been changed for presentation of these data. Further, FIG. 13 shows detection of goat IgG bound to selected electrodes on a micro array biochip containing electrodes and a polyvinyl alcohol porous matrix (Combimatrix Corporation, Mukilteo, Wash.). HRP-tagged mouse monoclonal anti-goat antibody was used for the electrochemical detection. Samples are in S1 (1, 3, 5) and S2 (2, 4, 6). The sign of the current flow has been changed for presentation of these data. These data are in excellent agreement as to what would be expected based upon earlier work using fluorescent tagged antibodies and standard fluorescence detection.

Oligonucleotide Capture

Figure 14:
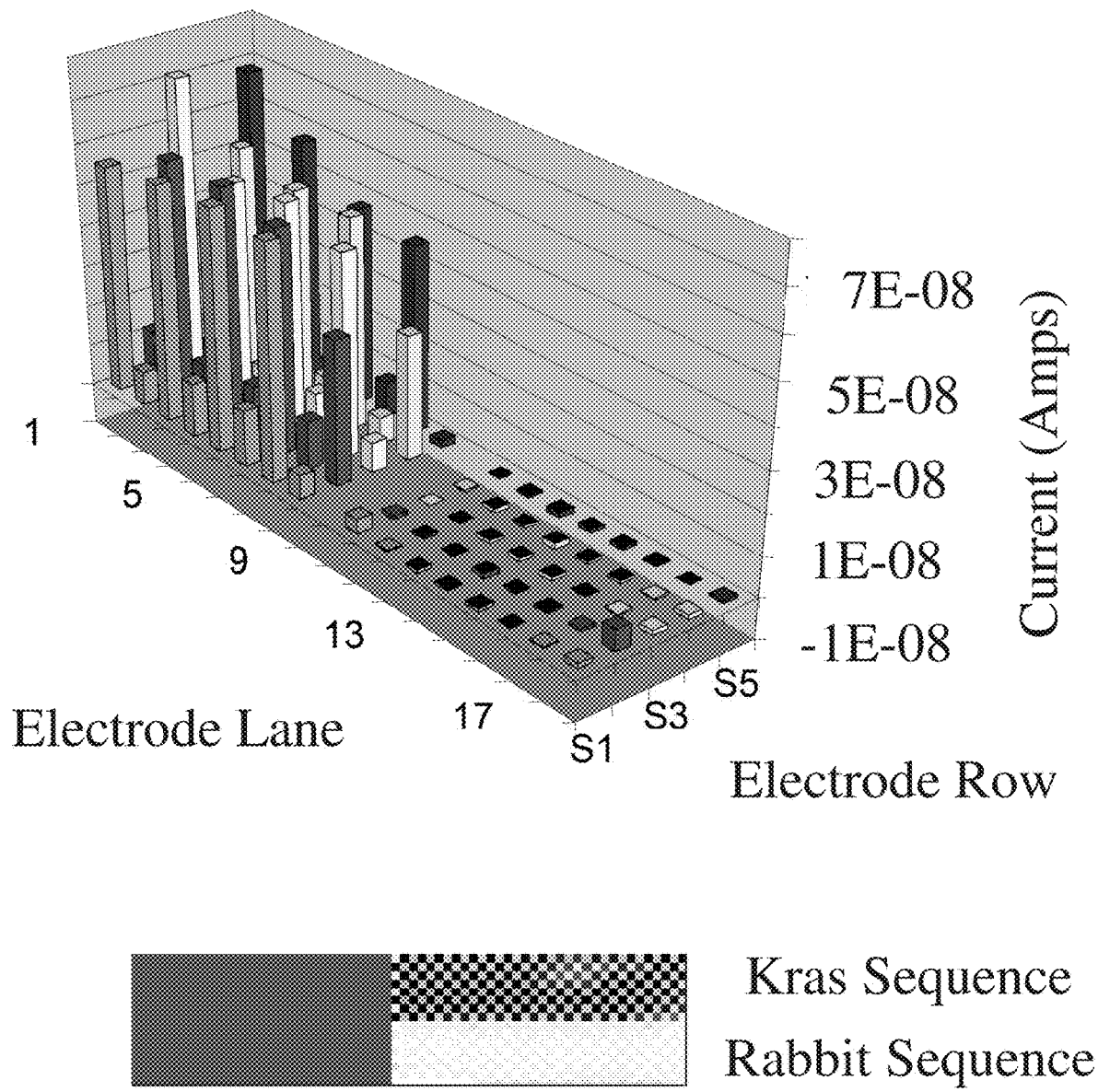
FIG. 14 shows a 3D plot for oligonucleotide hybridization electrochemical detection. Specifically, rabbit and Kras oligonucleotide sequences were in situ synthesized on an electrode containing microarray device. The chip was set up in an alternating electrode-counter electrode format having a checkerboard pattern of sites having a Kras (or rabbit) oligonucleotide capture probe sequence surrounded diagonally by counter electrodes without oligonucleotides synthesized thereon. Target Kras sample (Operon) was treated to form single-stranded DNA (Operon) and biotinylated with Kras complement (Operon) according to manufacturers instructions. Streptavidin conjugated with HRP (Sigma) was added to the biotinylated Kras sequence complement to form a target complex or complementary Kras affinity-bound to HRP. The target Kras sample complexed with HRP was added to the chip and each electrode was measured for current (amps). These data are shown in FIG. 14 in the top panel in a 3D plat and in the bottom panel showing a positive signal in a checkerboard for Kras oligonucleotide capture probes and the bottom panel showing no signal for rabbit sequence captures probes.
Figure 15A:
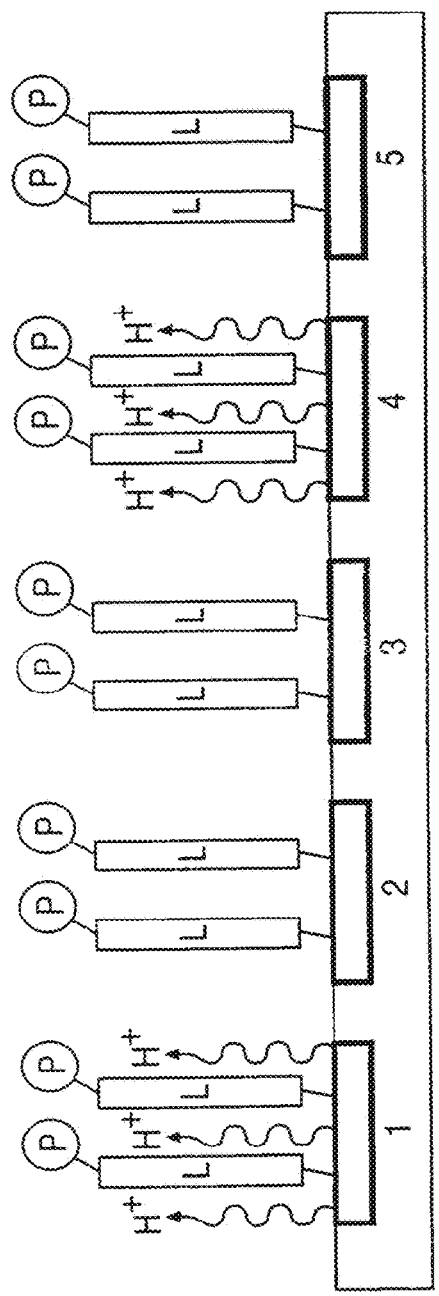
FIGS. 15a and 15b illustrate selective deprotection by electrochemically generated reagents (protons) generated at electrodes 1 and 4 to expose reactive functionalities ($NH_2$) on linker molecules (L) proximate electrodes 1 and 4. The substrate is shown in cross section and contains 5 electrodes.
Figure 15B:
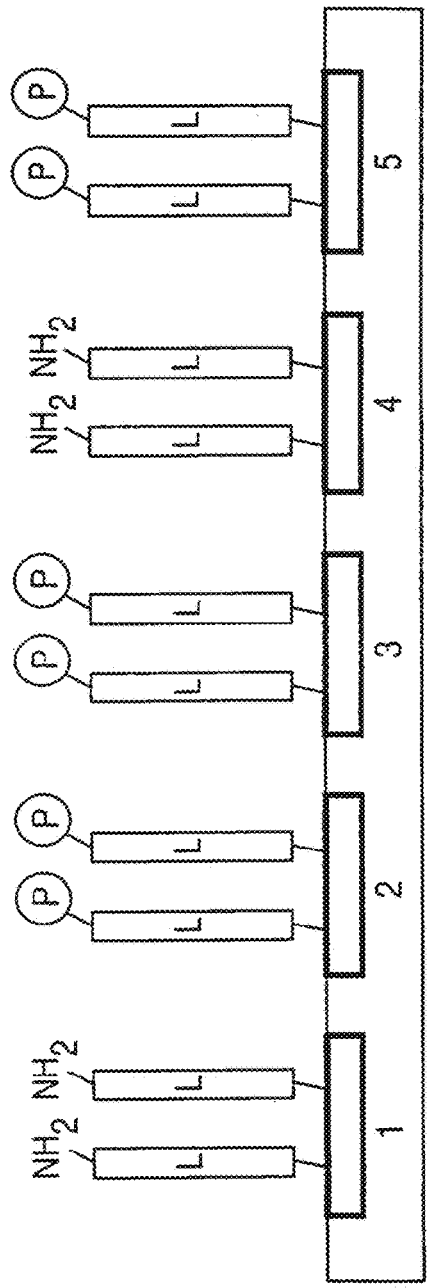
Figure 16A:
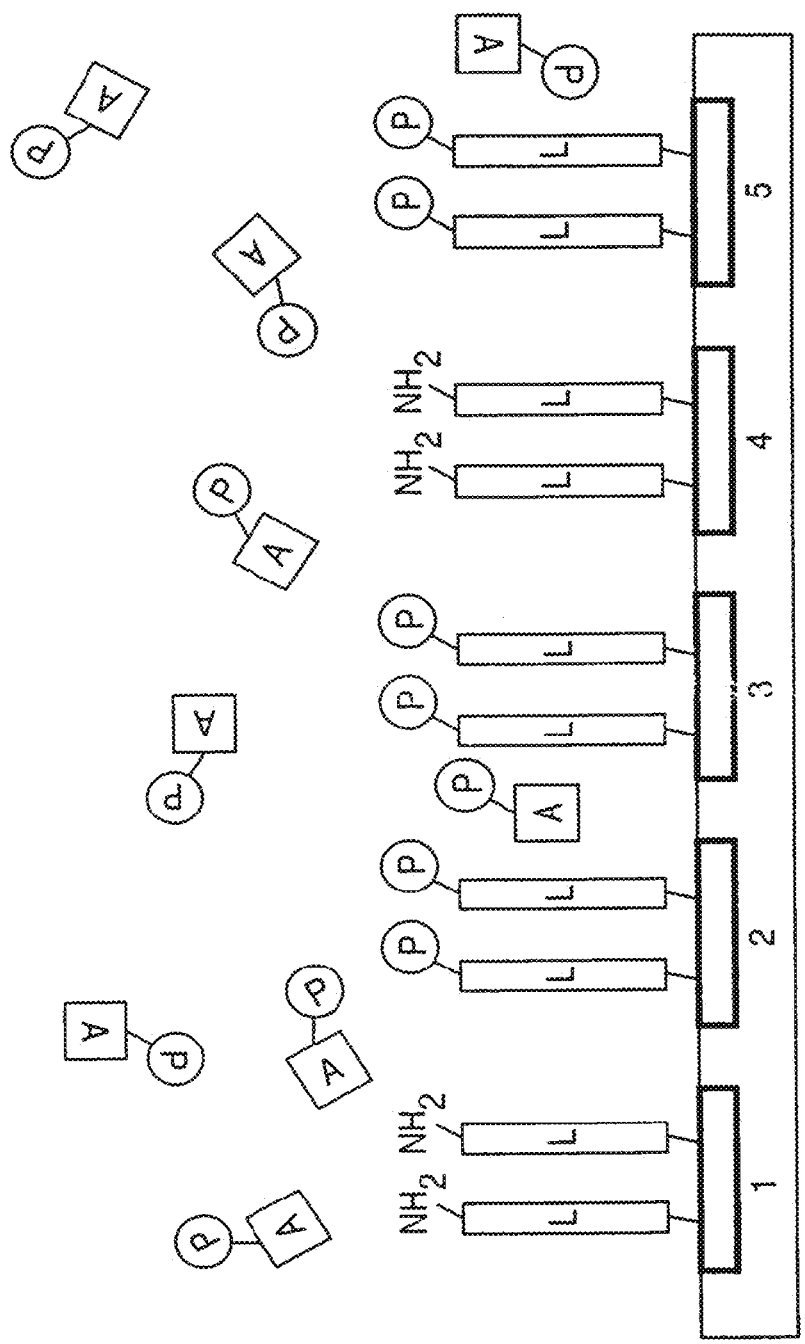
FIGS. 16a and 16b illustrate the bonding of monomers (A) bearing protected chemical functional groups (P) with the deprotected linker molecules (bearing reactive functionalities) proximate electrodes 1 and 4.
Figure 16B:
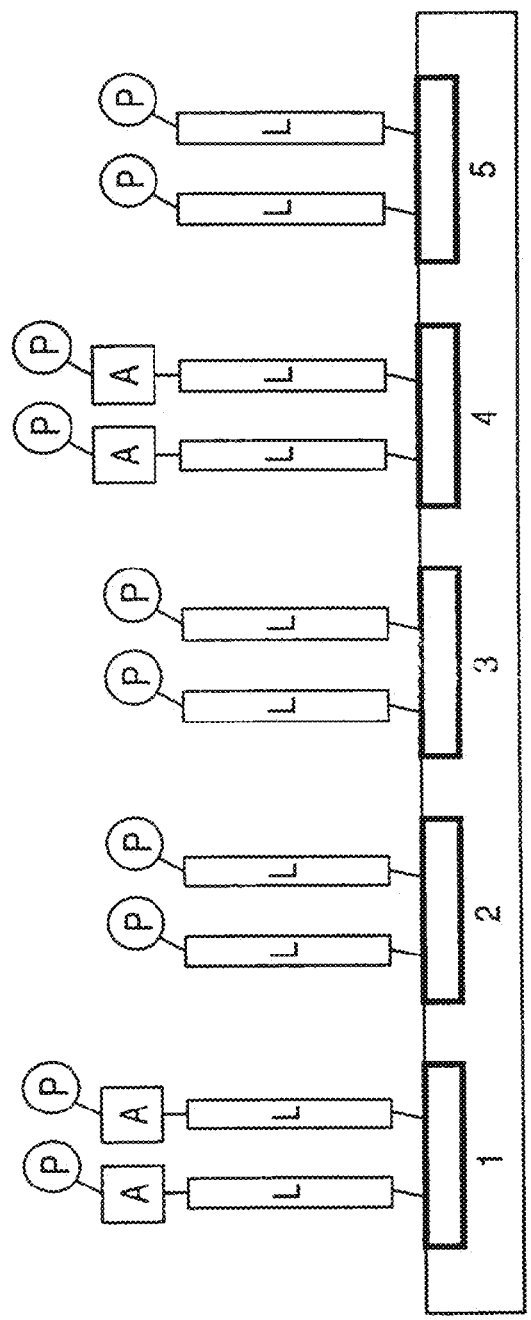
Figure 17A:
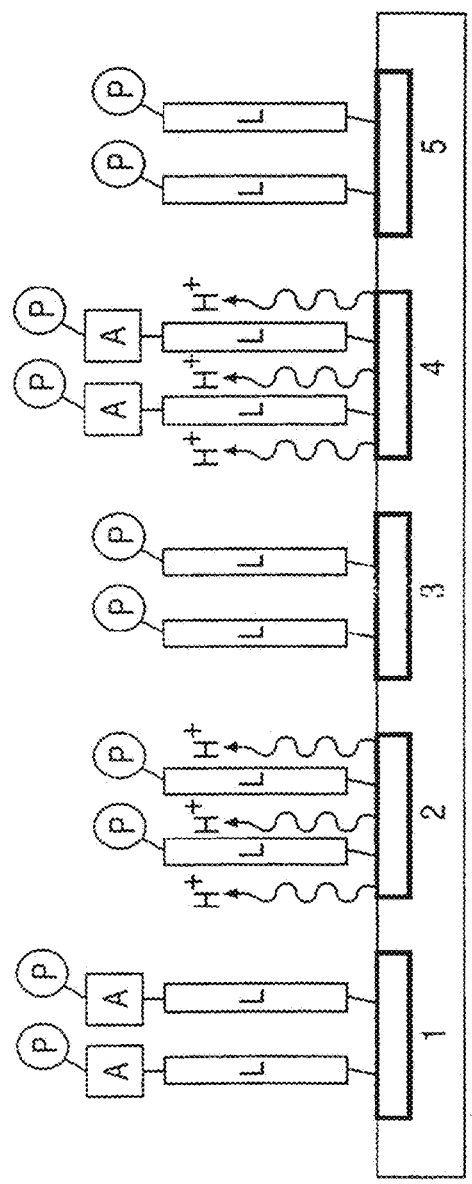
FIGS. 17a and 17b illustrate selective deprotection by protons generated at electrodes 2 and 4 of a second set of reactive functionalities on the molecule and monomer proximate electrodes 2 and 4, respectively.
Figure 17B:
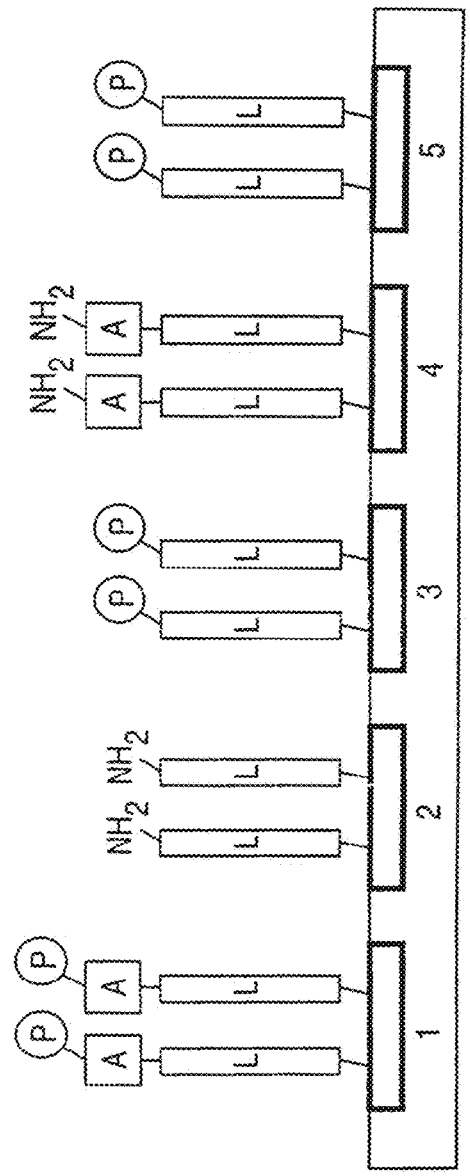
Figure 18A:
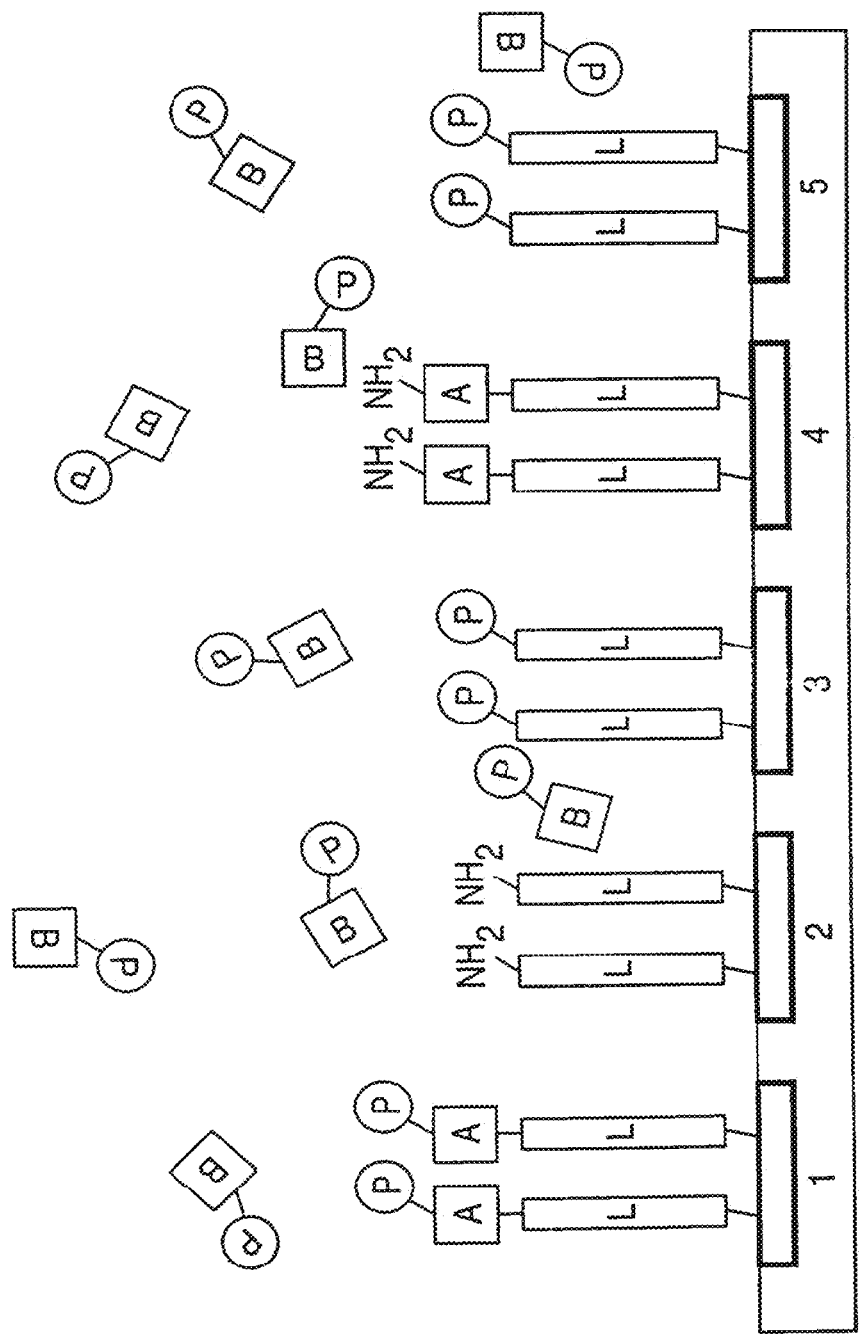
FIGS. 18a and 18b illustrate the bonding of monomers (B) bearing protected chemical functional groups (P) with the deprotected molecule and monomer proximate electrodes 2 and 4, respectively.
Figure 18B:
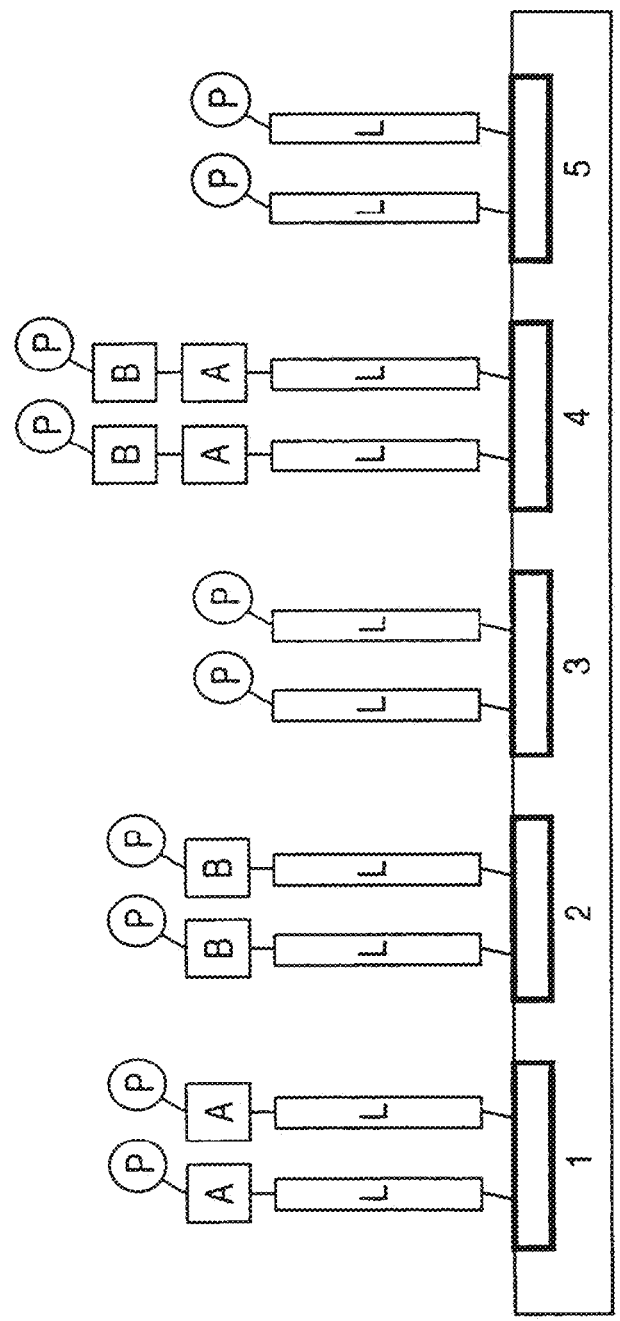
Figure 19:
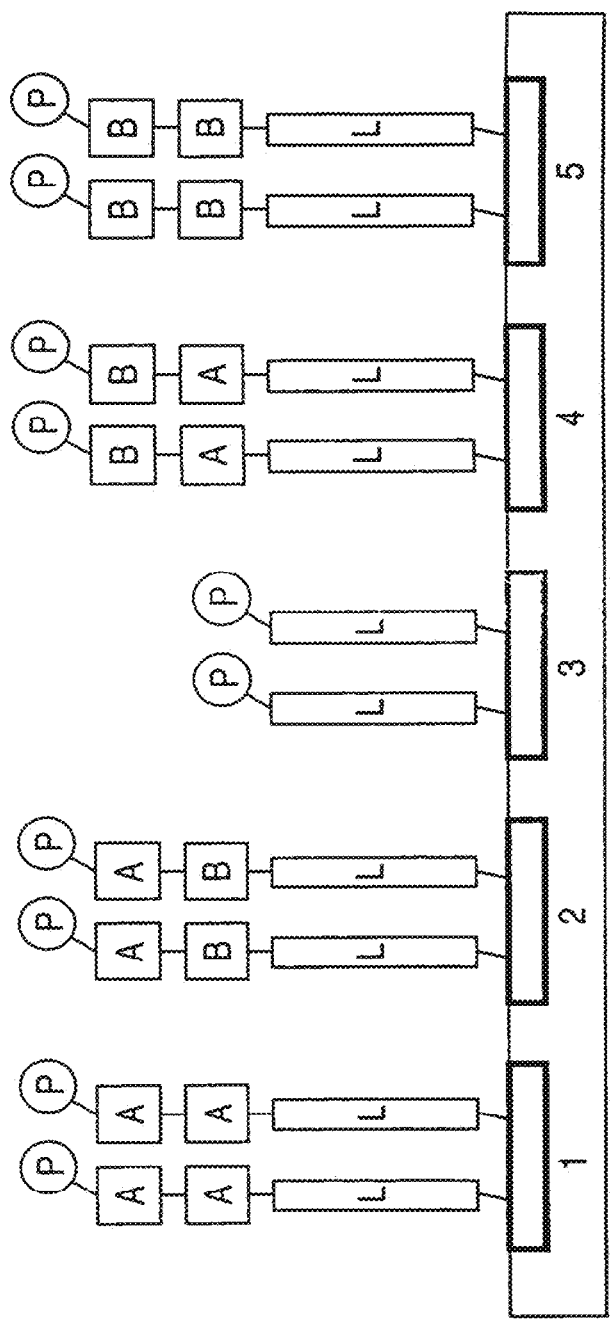
FIG. 19 illustrates a 5 electrode substrate bearing all possible combinations of monomers (A) and (B). The linker molecule proximate electrode 1 has a protected dimer, e.g., a dipeptide, containing two (A) monomers bonded thereto. The linker molecule proximate electrode 2 has a protected dimer containing a (B) monomer bonded to the linker molecule (L) and a protected (A) monomer bonded to said (B) monomer. The linker molecule proximate electrode 3, which represents a control electrode, demonstrates a linker molecule where no synthesis occurs because no potential is applied to the proximate electrode. The linker molecule proximate electrode 4 has a protected dimer containing an (A) monomer bonded to a linker molecule (L) and a protected (B) monomer bonded to said (A) monomer. The linker molecule proximate electrode 5 has a protected dimer containing two (B) monomers bonded to a linker molecule (L).

FIG. 14 shows a 3D plot for oligonucleotide hybridization electrochemical detection. Specifically, rabbit and Kras oligonucleotide sequences were in situ synthesized on an electrode containing microarray device. The Kras sequence used was TACGCCTCCA GCTCC [SEQ ID NO:1]. The rabbit sequence used was AGGCTACGAA GACTT [SEQ ID NO:2]. Therefore, the 25 oligonucleotide capture molecules synthesized by in situ electrochemistry techniques has a sequence of GGAGCTGGTG GCGTA [SEQ ID NO:3] for Kras known locations and a sequence of AAGTCTTCGT CGTAGCCT [SEQ ID NO:4] for rabbit known locations.

The chip was set up in an alternating electrode-counter electrode format having a checkerboard pattern of sites having a Kras (or rabbit) oligonucleotide capture probe sequence surrounded diagonally by counter electrodes without oligonucleotides synthesized thereon. Target Kras sample (Operon) was treated to form single-stranded DNA and biotinylated with Kras complement (Operon) according to manufacturers instructions. Streptavidin conjugated HRP was added to the biotinylated Kras sequence complement to form a target complex or complementary Kras affinity-bound to HRP. The target Kras sample complexed with HRP was added to the chip and each electrode was measured for current (amps). These data are shown in FIG. 14 in the top panel in a 3D plat and in the bottom panel showing a positive signal in a checker board for Kras oligonucleotide capture probes and the bottom panel showing no signal for rabbit sequence capture probes.

Multiple Analyte Detection

The ability of micro array devices to have synthesized many different capture molecules at different known locations allows for multiple analyte detection on a single chip. In each case the sample or samples to be investigated is labeled with an oxidation/reduction enzyme through standard conjugation means. Multiple samples can be pooled so that all of the targets to be investigated can be found from a single pooled sample. In one experiment samples of AGP, ricin and rabbit mRNA samples were pooled and investigated on a single chip using laccase as the oxidation/reduction enzyme. Only those known locations having the appropriate capture molecules detected target even though the group of targets were either protein or nucleic acids. Based upon multiple micro array investigations, the limits of detection were found to be 5 pg/ml for AGP and 300 pg/ml for ricin that translates to 2.5 fM in a volume of 0.5 ml. Moreover, the dynamic detection range spanned four logs.

The foregoing objects have been accomplished in accordance with this invention by providing a method for electrochemical placement of a material at a specific location on a substrate, which comprises the steps of:

providing a substrate having at its surface at least one electrode that is proximate to at least one molecule that is reactive with an electrochemically generated reagent, applying a potential to the electrode sufficient to generate electrochemical reagents capable of reacting to the at least one molecule proximate to the electrode, and producing a chemical reaction thereby.

The present invention also includes a method for the electrochemical placement of a material at a specific location on a substrate comprising the steps of:

providing a substrate having at its surface at least one electrode that is proximate to at least one molecule bearing at least one protected chemical functional group, applying a potential to the electrode sufficient to generate electrochemical reagents capable of deprotecting at least one of the protected chemical functional groups of the molecule, and bonding the deprotected chemical functional group with a monomer or a pre-formed molecule.

The present invention also includes a method for electrochemical synthesis of an array of separately formed polymers on a substrate, which comprises the steps of:

placing a buffering or scavenging solution in contact with an array of electrodes that is proximate to a substrate surface, said surface being proximate to one or more molecules bearing at least one protected chemical functional group attached thereto, selectively deprotecting at least one protected chemical functional group on at least one of the molecules;

bonding a first monomer having at least one protected chemical functional group to one or more deprotected chemical functional groups of the molecule;

selectively deprotecting a chemical functional group on the bonded molecule or another of the molecules bearing at least one protected chemical functional group;

bonding a second monomer having at least one protected chemical functional group to a deprotected chemical functional group of the bonded molecule or the other deprotected molecule; and repeating the selective deprotection of a chemical functional group on a bonded protected monomer or a bonded protected molecule and the subsequent bonding of an additional monomer to the deprotected chemical functional group until at least two separate polymers of desired length are formed on the substrate surface.

Another embodiment of the present invention also includes a method for electrochemical synthesis of an array of separately formed oligonucleotides on a substrate, which comprises the steps of:

placing a buffering or scavenging solution in contact with an array of electrodes that is proximate to a substrate surface, said surface being proximate to one or more molecules bearing at least one protected chemical functional group attached thereto, selectively deprotecting at least one protected chemical functional group on at least one of the molecules;

bonding a first nucleotide having at least one protected chemical functional group to one or more deprotected chemical functional groups of the molecule;

selectively deprotecting a chemical functional group on the bonded molecule or another of the molecules bearing at least one protected chemical functional group;

bonding a second nucleotide having at least one protected chemical functional group to a deprotected chemical functional group of the bonded molecule or the other deprotected molecule; and repeating the selective deprotection of a chemical functional group on a bonded protected nucleotide or a bonded protected molecule and the subsequent bonding of an additional nucleotide to the deprotected chemical functional group until at least two separate oligonucleotides of desired length are formed on the substrate surface.

A further embodiment of the present invention includes placing a "getter" structure such as a second electrode proximate to the array of electrodes or proximate to each of the electrodes individually. Such a "getter" structure may reduce chemical crosstalk between adjacent electrodes and/or prolong the life of semiconductor circuitry. Various semiconductor circuitry may be placed in a manner to control electrodes individually or corporately according to any one of the methods that are well known in the art. A "getter" structure in accordance with the present invention may be placed in an appropriate location either exposed to the external environment or internal to a semiconducting device.

By using the electrochemical techniques discussed herein, it is possible to place monomers, both those that can be used for polymer synthesis and those that can be decorated, and pre-formed molecules at small and precisely known locations on a substrate. It is therefore possible to synthesize polymers of a known chemical sequence at selected locations on a substrate. For example, in accordance with the presently disclosed invention, one can place nucleotides at selected locations on a substrate to synthesize desired sequences of nucleotides in the form of, for example, oligonucleotides.

It is to be understood that both the foregoing general description and the following detailed description are exemplary and explanatory only and are intended to provide further explanation of the present invention, as claimed.

The present invention provides methods for the preparation and use of a substrate having one or a plurality of chemical species in selected regions. The present invention is described herein primarily with regard to the preparation of molecules containing sequences of amino acids, but could be readily applied to the preparation of other polymers, as well as to the preparation of sequences of nucleic acids. Such polymers include, for example, both linear and cyclic polymers of nucleic acids, polysaccharides, phospholipids, and peptides having either alpha-, beta-, or omega- amino acids, polyurethanes, polyesters, polycarbonates, polyureas, polyamides, polyethyleneimines, polyarylene sulfides, polysiloxanes, polyimides, polyacetates, or other polymers which will be apparent upon review of this disclosure. In a preferred embodiment, the invention herein is used in the synthesis of peptides. In another preferred embodiment, the present invention is used for the synthesis of oligonucleotides and/or DNA.

The present invention is directed to placing molecules, selected generally from monomers, linker molecules and pre-formed molecules, including, in particular, nucleic acids, at a specific location on a substrate. The present invention is more particularly directed to the synthesis of polymers at a specific location on a substrate, and in particular polypeptides, by means of a solid phase polymerization technique, which generally involves the electrochemical removal of a protecting group from a molecule provided on a substrate that is proximate at least one electrode. The present invention is also particularly directed to the synthesis of oligonucleotides and/or DNA at selected locations on a substrate, by means of the disclosed solid phase polymerization technique.

Electrochemical reagents capable of electrochemically removing protecting groups from chemical functional groups on the molecule are generated at selected electrodes by applying a sufficient electrical potential to the selected electrodes. Removal of a protecting group, or "deprotection," in accordance with the invention, occurs at selected molecules when a chemical reagent generated by the electrode acts to deprotect or remove, for example, an acid or base labile protecting group from the selected molecules.

In one embodiment of the present invention, a terminal end of a monomer nucleotide, or linker molecule (i.e., a molecule which "links," for example, a monomer or nucleotide to a substrate) is provided with at least one reactive functional group, which is protected with a protecting group removable by an electrochemically generated reagent. The protecting group(s) is exposed to reagents electrochemically generated at the electrode and removed from the monomer, nucleotide or linker molecule in a first selected region to expose a reactive functional group. The substrate is then contacted with a first monomer or pre-formed molecule, which bonds with the exposed functional group(s). This first monomer or pre-formed molecule may also bear at least one protected chemical functional group removable by an electrochemically generated reagent.

The monomers or pre-formed molecules can then be deprotected in the same manner to yield a second set of reactive chemical functional groups. A second monomer or pre-formed molecule, which may also bear at least one protecting group removable by an electrochemically generated reagent, is subsequently brought into contact with the substrate to bond with the second set of exposed functional groups. Any unreacted functional groups can optionally be capped at any point during the synthesis process. The deprotection and bonding steps can be repeated sequentially at this site on the substrate until polymers or oligonucleotides of a desired sequence and length are obtained.

In another embodiment of the present invention, the substrate having one or more molecules bearing at least one protected chemical functional group bonded thereto is proximate an array of electrodes, which array is in contact with a buffering or scavenging solution. Following application of an electric potential to selected electrodes in the array sufficient to generate electrochemical reagents capable of deprotecting the protected chemical functional groups, molecules proximate the selected electrodes are deprotected to expose reactive functional groups, thereby preparing them for bonding. A monomer solution or a solution of pre-formed molecules, such as proteins, nucleic acids, polysaccharides, and porphyrins, is then contacted with the substrate surface and the monomers or pre-formed molecules bond with the deprotected chemical functional groups.

Another sufficient potential is subsequently applied to select electrodes in the array to deprotect at least one chemical functional group on the bonded molecule or another of the molecules bearing at least one protected chemical functional group. A second monomer or pre-formed molecule having at least one protected chemical functional group is subsequently bonded to a deprotected chemical functional group of the bonded molecule or the other deprotected molecule. The selective deprotection and bonding steps can be repeated sequentially until polymers or oligonucleotides of a desired sequence and length are obtained. The selective deprotection step is repeated by applying another potential sufficient to effect deprotection of a chemical functional group on a bonded protected monomer or a bonded protected molecule. The subsequent bonding of an additional monomer or pre-formed molecule to the deprotected chemical functional group(s) until at least two separate polymers or oligonucleotides of desired length are formed on the substrate. FIGS. 15-19 generically illustrate the above-discussed embodiments.

Preferred embodiments of the present invention use a buffering or scavenging solution in contact with each electrode, which is buffered towards the electrochemically generated reagents, in particular, towards protons and/or hydroxyl ions, and that actively prevents chemical cross-talk caused by diffusion of the electrochemically generated ions from one electrode to another electrode in an array. For example, when an electrode exposed to an aqueous or partially aqueous media is biased to a sufficiently positive (or negative) potential, protons (or hydroxyl ions) are produced as products of water hydrolysis. Protons, for example, are useful for removing electrochemical protecting groups from several molecules useful in combinatorial synthesis, for example, peptides, nucleic acids, and polysaccharides.

In order to produce separate and pure polymers, it is desirable to keep these protons (or hydroxyl ions) confined to the area immediately proximate the selected electrode(s) in order to minimize, and, if possible to eliminate, chemical cross-talk between nearby electrodes in an array. The spatial extent of excursion of electrochemically generated reagents can be actively controlled by the use of a buffering or scavenging solution that reacts with the reagents that move away from the selected electrodes, thus preventing these reagents from reacting at a nearby electrode.

Another technique for confining these electrochemically generated reagents to the area immediately proximate the selected electrode(s) is to place a "getter" structure in proximity to the selected electrode(s) and substantially exposed to the external environment. Such a "getter" structure may be used in conjunction with or in place of a scavenging solution. A "getter" structure may be designed of any suitable material and formed into any suitable shape or size as skilled artisans will readily appreciate. The most important criteria for such a "getter" structure is that it function to scavenge electrochemically generated reagents that may diffuse away from the selected electrode(s). The "getter" structure may function passively by reacting chemically with the electrochemically generated reagents. Alternatively, the "getter" structure may function actively to scavenge the electrochemically generated reagents. This may be performed by applying sufficient potential to the "getter" structure to cause electrochemical scavenging. Another function of the "getter" structure may be to prevent the diffusion of ions toward or into circuitry such as transistors that may be operably linked to the selected electrode(s). In accordance with this function, the "getter" structure may be placed substantially at the interface between an insulating dielectric and a metallization layer operably linked to the selected electrode(s).

Figure 48B:
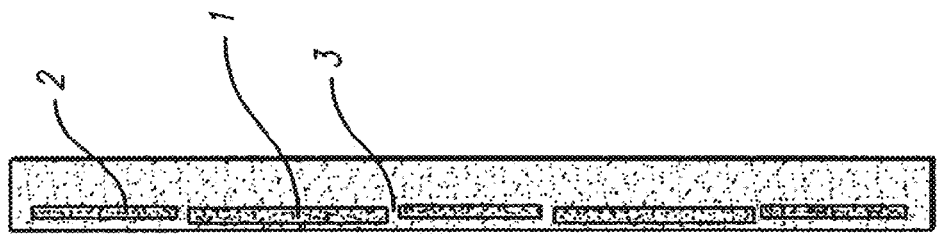
FIG. 48b depicts a cross-section of a selected electrode having a "getter" structure 2 placed substantially at the interface between an insulating dielectric layer 3 and the metal surface of the semiconductor. The "getter" structure in this figure forms a substantially solid sheet with holes allowing the selected electrodes to contact the environment. This and similar structures extend the lifetime of semiconductor circuitry thereby making practical the submersion of a chip in ionic solutions.
Figure 48A:
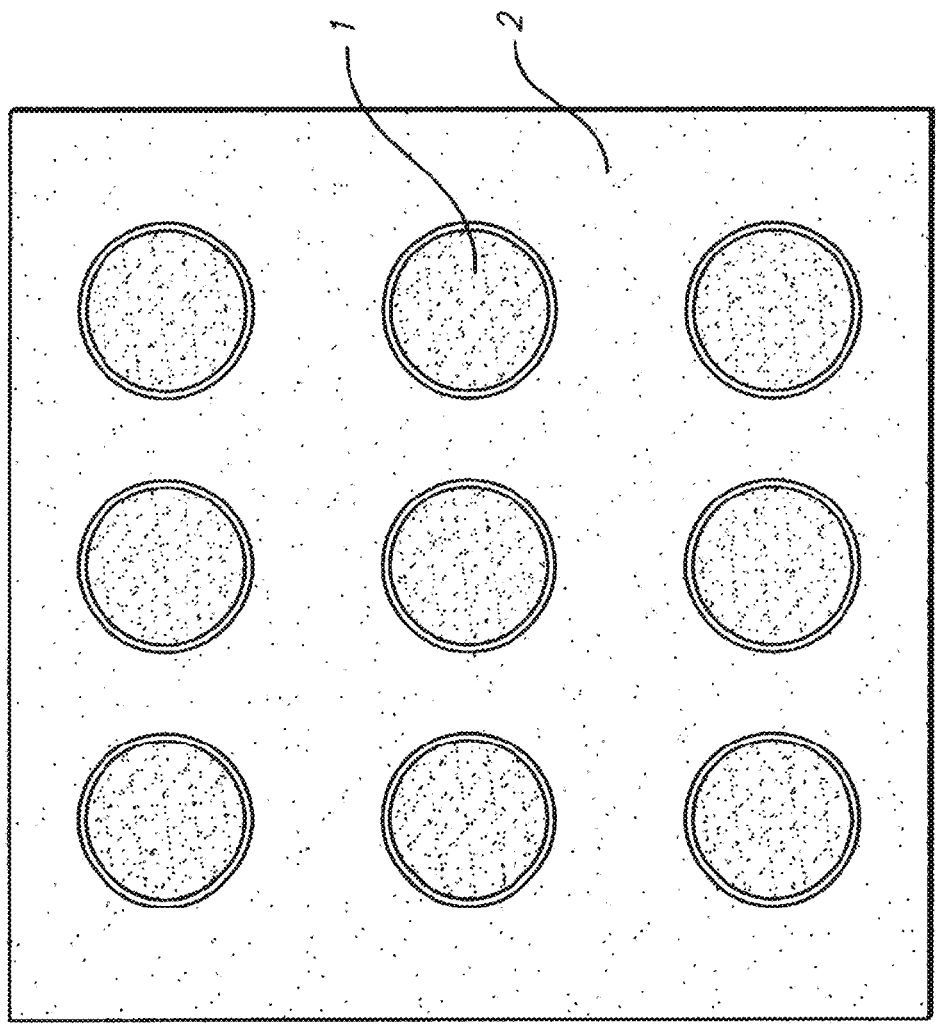
FIG. 48a depicts a top view of an electrode array having a "getter" structure 2 which forms a substantial sheet around the individual electrodes 1 configured in the electrode array. Such a "getter" structure 2 in a sheet functions to capture ions which may diffuse into or toward the semiconductor circuitry.
Figure 50A:
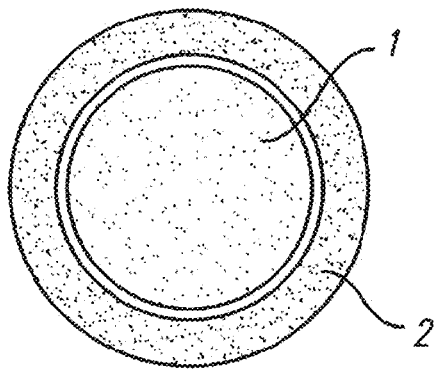
FIGS. 50a and 50b represent an exemplary selected electrode 1 useful according to the present invention having a "getter" structure 2 beneath the surface of the electrode. Such a configuration may be especially useful to control ion diffusion toward and into semiconductor circuitry.
Figure 49A:
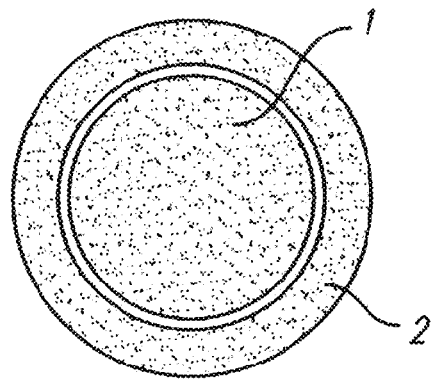
FIGS. 49a and 49b represent an exemplary selected electrode 1 useful according to the present invention having a "getter" structure 2 substantially exposed to the external environment. Such a configuration may be especially useful to control electrochemically generated reagents diffusing between electrodes in an array as well as ions diffusing toward and into semiconductor circuitry.
Figure 50B:
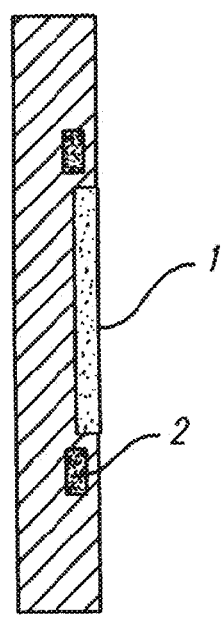
Figure 49B:
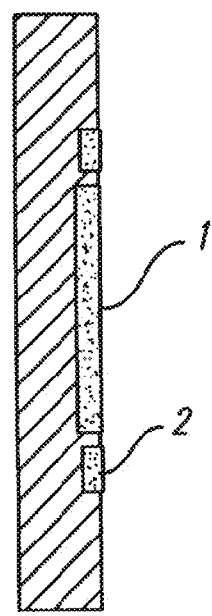

Some preferred embodiments of such a "getter" structure include a metal sheet that may cover or substantially cover the surface of the circuitry of the electrode device used in the present invention. An example of such a structure is depicted in FIG. 48. This metal sheet may have holes existing where the electrodes are placed. The electrodes may in turn be separated from the "getter" structure by a dielectric as is demonstrated in FIG. 45. Even more preferred embodiments of such a "getter" structure include a ring electrode around the selected electrode(s). A ringed "getter" structure offers at least two advantages over other embodiments such as those described above. First, much of the diffusion of ions occurs along defect sites that form at the interface between the selected electrode(s) and the dielectric. Second, it is relatively easy to monitor the effects of the "getter" structure on the environment when such a structure is utilized. Such a structure is exemplified in FIGS. 45 and 48-50.

The "getter" structure according to the present invention further solves the problem associated with exposing semiconductor devices that may be used in conjunction with the selected electrodes to environments that contain ions that diffuse into the device. In particular, ions from solutions to which a semiconductor device is exposed may diffuse into regions of a semiconductor device that have been doped with ions in a precise manner to impart particular electrical properties to these regions. An important example is the gate of a metal oxide semiconductor (MOS) transistor circuit element. Here either positive or negative ions (e.g., p-doped or n-doped) have been diffused into the gate region to make the region semiconducting. The threshold voltage and current-voltage characteristics of the transistor gate depend in a sensitive way on doping levels. The long term reliability of many semiconductor devices depends on isolating them effectively from ionic contamination. For example, the adhesives and encapsulants used in the semiconductor industry are treated to render the ion concentrations in these materials as low as possible, often less than parts per million.

Semiconductor transistors are rapidly destroyed when silicon chips are used in ion-containing solutions. Semiconductor transistors are presently manufactured with a thin layer of partially conductive material in their transistor junctions. This partially conductive layer is infused or doped with a concentration of particles, i.e. ions, to achieve a balanced level of conductivity. This is typically done at present by doping the junction with a substance rich in ions such as arsenic, boron or phosphorous. When too many ions are present, the material functions as a metal and becomes highly conductive. When there are too few ions present, the material functions as an insulator and demonstrates very low conductivity. In order to perform properly as a transistor, the material must achieve a very specific level of conductivity intermediate between that of a metal and that of an insulator. Contamination of the partially conductive layer at the transistor junction by ions diffusing into a semiconductor device changes conductivity of the junction and thus destroys the transistor.

Ion contamination represents a serious obstacle for exposing semiconductor circuitry to hostile or ion-containing solutions. This presents a major impediment to devices according to some embodiments of the present invention wherein semiconductor circuitry may be operably linked to selected electrode(s), which are in turn immersed in high concentration ionic solutions for extended periods of time. As a result, embodiments according to the present invention that utilize structures such as a "getter" structure are designed both to monitor and to obviate ion contamination are particularly preferred.

Such devices may be designed to work by scavenging ions that diffuse into the device from solutions to which the electrode and associated circuitry may be exposed. Contaminating ions may be scavenged passively by reacting chemically with a material that is placed between them and the active circuitry. Alternatively, they can be scavenged actively by applying a voltage to a second electrode placed proximate to the selected electrode(s) that sets up an electric field that causes ions to migrate to the electrode and away from the active circuitry. Ion contamination can be monitored by placing transistor gates adjacent to the getter structure and monitoring shifts in threshold voltage. Such "getter" structures may be designed by skilled artisans of any suitable material in any suitable size or shape and thereby be adapted to any electrode geometries. Moreover, it is generally preferable to place the "getter" structure beneath an electrically insulating or dielectric layer such as a silicon nitride that generally covers a semiconductor and thereby separates the semiconductor from the environment, and, in particular, from the ionic solutions required in the practice of the present invention. It is particularly preferable to place the "getter" structure in a ring either substantially beneath or substantially within a dielectric layer and substantially surrounding the select electrode(s). An exemplary cross-section of such a structure is presented in FIG. 48. As a result of the "getter" structure used in accordance with the present invention, selected electrode(s) may be advantageously controlled by automated computer circuitry while maintaining a viable lifespan for the same in the environment of ionic solutions. Thus, it is practical to synthesize a variety of chemical molecules on the surface of electrodes integrated into or operably linked to a computer chip in accordance with methods well known to those of skill in the art.

The present invention advantageously minimizes, and preferably eliminates, chemical cross-talk between nearby areas of polymer or nucleic acid sequence synthesis on a substrate, thus enabling the synthesis of separate arrays of pure polymers or nucleic acid sequences in a small specified area on a substrate using conventional electrochemically generated reagents and known electrochemical reactions. The ability of the inventive methods to place materials at specific locations on a substrate enables the inventive method to be used in several areas of synthesis in addition to polymer synthesis. Several examples of this synthesis include DNA and oligonucleotide synthesis, monomer decoration, which involves the addition of chemical moieties to a single monomer, and inorganic synthesis, which involves the addition of, for example, metals to porphyrins.

Other embodiments of the present invention contemplate an array of electrodes of small micron size, for example, ranging from 1 to 100 microns in diameter, and separated by many microns. However, it is also contemplated that electrodes separated by only submicron distances can be used, if desired. This arrangement affords a large quantity of separate and pure polymers or nucleic acid sequences to be synthesized simultaneously in a small area on a substrate in accordance with the inventive method. This capability renders the inventive method easily automated. The ability of the present invention to be automated easily while retaining the capability of producing separate and diverse arrays of pure polymers and nucleic acid sequences makes the present invention ideal for use in the rapidly developing areas of combinatorial chemistry and functional genomics.

Essentially, any conceivable substrate may be employed in accordance with the present invention. The substrate may be biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, circle, etc. The substrate is preferably flat, but may take on a variety of alternative structure configurations. For example, the substrate may contain raised or depressed regions on which synthesis may take place. The substrate and its surface preferably form a rigid support on which to carry out the reactions described herein. The substrate and the area for synthesis of each individual polymer or small molecule may be of any size and shape. Moreover, a substrate may comprise different materials at different regions.

Contemplated materials, which are preferably used as substrates and which are capable of holding and insulating electrically the electrodes, include: undoped semiconductors, such as silicon nitride, silicon oxide, silicon, diamond, chalcopyrites, wurtzites, sphalerites, halites, Group III-V compounds, and Group I-VI compounds; glass, such as, cobalt glass, pyrex glass, vycor glass, borosilicate glass and quartz; ceramics, such as, alumina, porcelain, zircon, corderite, titanates, metal oxides, clays, and zeolites; polymers, such as, paralyene, high density polyethylene, teflons, nylons, polycarbonates, polystyrenes, polyacylates, polycyanoacrylates, polyvinyl alcohols, polyimides, polyamides, polysiloxanes, polysilicones, polynitriles, polyvinyl chlorides, alkyd polymers, celluloses, expoxy polymers, melamines, urethanes, copolymers and mixtures of any of the above with other polymers, and mixtures of any of the above with glass or ceramics; and waxes, such as, apeizon. Other substrate materials will be readily apparent to those of skill in the art upon review of this disclosure.

The substrate of the invention is proximate to at least one electrode, i.e., an electrically conducting region of the substrate that is substantially surrounded by an electrically insulating region. The electrode(s), by being "proximate" to the substrate, can be located at the substrate, i.e., embedded in or on the substrate, can be next to, below, or above the substrate, but need to be in close enough proximity to the substrate so that the reagents electrochemically generated at the electrode(s) can accomplish the desired deprotection of the chemical functional groups on the monomer(s) and/or molecule(s).

In addition to being proximate to at least one electrode, the substrate has on a surface thereof, at least one molecule, and preferably several molecules, bearing at least one chemical functional group protected by an electrochemically removable protecting group. These molecules bearing protected chemical functional groups also need to be proximate to the electrode(s). In this regard, the molecules on the surface of the substrate need to be in close enough proximity to the electrode(s) so that the electrochemical reagents generated at the electrode can remove the protecting group from at least one protected functional group on the proximate molecule(s).

The molecules bearing a protected chemical functional group that are attached to the surface of the substrate may be selected generally from monomers, linker molecules and pre-formed molecules. Preferably, the molecules attached to the surface of the substrate include monomers, nucleotides, and linker molecules. All of these molecules generally bond to the substrate by covalent bonds or ionic interactions. Alternatively, all of these molecules can be bonded, also by covalent bonds or ionic interactions, to a layer overlaying the substrate, for example, a permeable membrane layer, which layer can be adhered to the substrate surface in several different ways, including covalent bonding, ionic interactions, dispersive interactions and hydrophilic or hydrophobic interactions. In still another manner of attachment, a monomer or pre-formed molecule may be bonded to a linker molecule that is bonded to either the substrate or a layer overlaying the substrate.

The monomers, linker molecules and pre-formed molecules used herein, are preferably provided with a chemical functional group that is protected by a protecting group removable by electrochemically generated reagents. If a chemical functional group capable of being deprotected by an electrochemically generated reagent is not present on the molecule on the substrate surface, bonding of subsequent monomers or pre-formed molecules cannot occur at this molecule. Preferably, the protecting group is on the distal or terminal end of the linker molecule, monomer, or pre-formed molecule, opposite the substrate. That is, the linker molecule preferably terminates in a chemical functional group, such as an amino or carboxy acid group, bearing an electrochemically removable protective group. Chemical functional groups that are found on the monomers, linker molecules and pre-formed molecules include any chemically reactive functionality. Usually, chemical functional groups are associated with corresponding protective groups and will be chosen or utilized based on the product being synthesized. The molecules of the invention bond to deprotected chemical functional groups by covalent bonds or ionic interactions.

Monomers used in accordance with the present invention to synthesize the various polymers contemplated include all members of the set of small molecules that can be joined together to form a polymer. This set includes, but is not limited to, the set of common L-amino acids, the set of D-amino acids, the set of synthetic amino acids, the set of nucleotides and the set of pentoses and hexoses. As used herein, monomers include any member of a basis set for synthesis of a polymer. For example, trimers of L-amino acids form a basis set of approximately 8000 monomers for synthesis of polypeptides. Different basis sets of monomers may be used at successive steps in the synthesis of a polymer using the inventive method. The number of monomers that can be used in accordance with the inventive synthesis methods can vary widely, for example from 2 to several thousand monomers can be used, but in more preferred embodiments, the number of monomers will range from approximately 4 to approximately 200, and, more preferably, the number of monomers will range from 4-20.

Additional monomers that can be used in accordance with the invention also include the set of monomers that can be decorated, i.e., monomers to which chemical moieties can be added, such as prostaglandins, benzodiazapines, thromboxanes and leukotrienes. Combinations of monomers useful for polymer synthesis and monomers that can be decorated are also contemplated by the invention. The above-discussed monomers may be obtained in unprotected form from most any chemical supply company, and most, if not all, can be obtained in protected form from Bachem, Inc., Torrance, Calif. Phosphoramidite monomers for nucleic acid synthesis can be obtained from Applied Biosystems, Inc., Foster City, Calif.

In a preferred embodiment of the invention, the monomers are amino acids containing a protective group at its amino or carboxy terminus that is removable by an electrochemically generated reagent. A polymer in which the monomers are alpha amino acids and are joined together through amide bonds is a peptide, also known as a polypeptide. In the context of the present invention, it should be appreciated that the amino acids may be the L-optical isomer or the D-optical isomer or a mixture of the two. Peptides are at least two amino acid monomers long, and often are more than 20 amino acid monomers long.

Furthermore, essentially any pre-formed molecule can be bonded to the substrate, a layer overlaying the substrate, a monomer or a linker molecule. Pre-formed molecules include, for example, proteins, including in particular, receptors, enzymes, ion channels, and antibodies, nucleic acids, polysaccharides, porphyrins, and the like. Pre-formed molecules are, in general, formed at a site other than on the substrate of the invention. In a preferred embodiment, a pre-formed molecule is bonded to a deprotected functional group on a molecule, monomer, or another pre-formed molecule. In this regard, a pre-formed molecule that is already attached to the substrate may additionally bear at least one protected chemical functional group to which a monomer or other pre-formed molecule may bond, following deprotection of the chemical functional group.

Protective groups are materials that bind to a monomer, a linker molecule or a pre-formed molecule to protect a reactive functionality on the monomer, linker molecule or pre-formed molecule, which may be removed upon selective exposure to an activator, such as an electrochemically generated reagent. Protective groups that may be used in accordance with the present invention preferably include all acid and base labile protecting groups. For example, peptide amine groups are preferably protected by t-butyloxycarbonyl (BOC) or benzyloxycarbonyl (CBZ), both of which are acid labile, or by 9-fluorenylmethoxycarbonyl (FMOC), which is base labile. Additionally, hydroxy groups on phosphoramidites may be protected by dimethoxytrityl (DMT), which is acid labile. Exocyclic amine groups on nucleosides, in particular on phosphoramidites, are preferably protected by dimethylformamidine on the adenosine and guanosine bases, and isobutyryl on the cytidine bases, both of which are base labile protecting groups. This protection strategy is known as fast oligonucleotide deprotection (FOD). Phosphoramidites protected in this manner are known as FOD phosphoramidites.

Additional protecting groups that may be used in accordance with the present invention include acid labile groups for protecting amino moieties: tertbutyloxycarbonyl,- tert-amyloxycarbonyl, adamantyloxycarbonyl, 1-methylcyclobutyloxycarbonyl, 2-(p-biphenyl)propyl(2)oxycarbonyl, 2- (p-phenylazophenylyl)propyl(2)oxycarbonyl, .alpha...alpha.-dimethyl-3,5-dimethyloxybenzyloxy-carbonyl, 2-phenylpropyl(2)oxycarbonyl, 4-methyloxybenzyloxycarbonyl, benzyloxycarbonyl, furfuryloxycarbonyl, triphenylmethyl (trityl), p-toluenesulfenylaminocarbonyl, dimethylphosphinothioyl, diphenylphosphinothioyl, 2-benzoyl-1-methylvinyl, o-nitrophenylsulfenyl, and 1- naphthylidene; as base labile groups for protecting amino moieties: 9- fluorenylmethyloxycarbonyl, methylsulfonylethyloxycarbonyl, and 5-benzisoazolylmethyleneoxycarbonyl; as groups for protecting amino moieties that are labile when reduced: dithiasuccinoyl, p-toluene sulfonyl, and piperidino-oxycarbonyl; as groups for protecting amino moieties that are labile when oxidized: (ethylthio)carbonyl; as groups for protecting amino moieties that are labile to miscellaneous reagents, the appropriate agent is listed in parenthesis after the group: phthaloyl (hydrazine), trifluoroacetyl (piperidine), and chloroacetyl (2- aminothiophenol); acid labile groups for protecting carboxylic acids: tert-butyl ester; acid labile groups for protecting hydroxyl groups: dimethyltrityl; and basic labile groups for protecting phosphotriester groups: cyanoethyl.

As mentioned above, any unreacted deprotected chemical functional groups may be capped at any point during a synthesis reaction to avoid or to prevent further bonding at such molecule. Capping groups "cap" deprotected functional groups by, for example, binding with the unreacted amino functions to form amides. Capping agents suitable for use in the present invention include: acetic anhydride, n-acetylimidizole, isopropenyl formate, fluorescamine, 3-nitrophthalic anhydride and 3-sulfoproponic anhydride. Of these, acetic anhydride and n-acetylimidizole are preferred.

In accordance with the invention, the surface of the substrate is preferably provided with a layer of linker molecules. Linker molecules allow for indirect attachment of monomers or pre-formed molecules to the substrate or a layer overlaying the substrate. The linker molecules are preferably attached to an overlaying layer via silicon-carbon bonds, using, for example, controlled porosity glass (CPG) as the layer material. Linker molecules also facilitate target recognition of the synthesized polymers. Furthermore, the linker molecules are preferably chosen based upon their hydrophilic/hydrophobic properties to improve presentation of synthesized polymers to certain receptors. For example, in the case of a hydrophilic receptor, hydrophilic linker molecules will be preferred so as to permit the receptor to approach more closely the synthesized polymer.

The linker molecules are preferably of sufficient length to permit polymers on a completed substrate to interact freely with binding entities exposed to the substrate. The linker molecules, when used, are preferably 650 atoms long to provide sufficient exposure of the functional groups to the binding entity. The linker molecules, which may be advantageously used in accordance with the invention include, for example, aryl acetylene, ethylene glycol oligomers containing from 2 to 20 monomer units, diamines, diacids, amino acids, and combinations thereof. Other linker molecules may be used in accordance with the different embodiments of the present invention and will be recognized by those skilled in the art in light of this disclosure.

According to another preferred embodiment, linker molecules may be provided with a cleavable group at an intermediate position, which group can be cleaved with an electrochemically generated reagent. This group is preferably cleaved with a reagent different from the reagent(s) used to remove the protective groups. This enables removal of the various synthesized polymers or nucleic acid sequences following completion of the synthesis by include: acetic anhydride, n-acetylimidizole, isopropenyl formate, fluorescamine, 3-nitrophthalic anhydride and 3-sulfopropionic anhydride. Of these, acetic anhydride and n-acetylimidizole are preferred.

In accordance with the invention, the surface of the substrate is preferably provided with a layer of linker molecules. Linker molecules allow for indirect attachment of monomers or pre-formed molecules to the substrate or a layer overlaying the substrate. The linker molecules are preferably attached to an overlaying layer via silicon-carbon bonds, using, for example, controlled porosity glass (CPG) as the layer material. Linker molecules also facilitate target recognition of the synthesized polymers. Furthermore, the linker molecules are preferably chosen based upon their hydrophilic/hydrophobic properties to improve presentation of synthesized polymers to certain receptors. For example, in the case of a hydrophilic receptor, hydrophilic linker molecules will be preferred so as to permit the receptor to approach more closely the synthesized polymer.

The linker molecules are preferably of sufficient length to permit polymers on a completed substrate to interact freely with binding entities exposed to the substrate. The linker molecules, when used, are preferably 650 atoms long to provide sufficient exposure of the functional groups to the binding entity. The linker molecules, which may be advantageously used in accordance with the invention include, for example, aryl acetylene, ethylene glycol oligomers containing from 2 to 20 monomer units, diamines, diacids, amino acids, and combinations thereof. Other linker molecules may be used in accordance with the different embodiments of the present invention and will be recognized by those skilled in the art in light of this disclosure.

According to another preferred embodiment, linker molecules may be provided with a cleavable group at an intermediate position, which group can be cleaved with an electrochemically generated reagent. This group is preferably cleaved with a reagent different from the reagent(s) used to remove the protective groups. This enables removal of the various synthesized polymers or nucleic acid sequences following completion of the synthesis by way of electrochemically generated reagents. In particular, derivatives of the acid labile 4,4'-dimethyoxytrityl molecules with an exocyclic active ester can be used in accordance with the present invention. These linker molecules can be obtained from Perspective Biosystems, Framingham, Mass. More preferably, N-succinimidyl-4[bis-(4-methoxyphenyl)-chloromethyl]-benzoate is used as a cleavable linker molecule during DNA synthesis. The synthesis and use of this molecule is described in A Versatile Acid-Labile Linker for Modification of Synthetic Biomolecules, by Brian D. Gildea, James M. Coull and Hubert Koester, Tetrahedron Letters, Volume 31, No. 49, pgs 7095-7098 (1990). Alternatively, other manners of cleaving can be used over the entire array at the same time, such as chemical reagents, light or heat.

The use of cleavable linker groups affords dissociation or separation of synthesized molecules, e.g., polymers or nucleic acid sequences, from the electrode array at any desired time. This dissociation allows transfer of the, for example, synthesized polymer or nucleic acid sequence, to another electrode array or to a second substrate. The second substrate could contain bacteria and serve to assay the effectiveness of molecules made on the original electrode array at killing bacteria. Alternatively, the second substrate could be used to purify the materials made on the original electrode array. Obviously, those skilled in the art can contemplate several uses for transferring the molecules synthesized on the original electrode to a second substrate.

The molecules of the invention, i.e., the monomers, linker molecules and pre-formed molecules, can be attached directly to the substrate or can be attached to a layer or membrane of separating material that overlays the substrate. Materials that can form a layer or membrane overlaying the substrate, such that molecules can be bound there for modification by electrochemically generated reagents, include: controlled porosity glass (CPG); generic polymers, such as, teflons, nylons, polycarbonates, polystyrenes, polyacylates, polycyanoacrylates, polyvinyl alcohols, polyamides, polyimides, polysiloxanes, polysilicones, polynitriles, polyelectrolytes, hydrogels, epoxy polymers, melamines, urethanes and copolymers and mixtures of these and other polymers; biologically derived polymers, such as, polysaccharides, polyhyaluric acids, celluloses, and chitons; ceramics, such as, alumina, metal oxides, clays, and zeolites; surfactants; thiols; self-assembled monolayers; porous carbon; and fullerine materials. The membrane can be coated onto the substrate by spin coating, dip coating or manual application, or any other art acceptable form of coating.

Reagents that can be generated electrochemically at the electrodes fall into two broad classes: oxidants and reductants. There are also miscellaneous reagents that are useful in accordance with the invention. Oxidants that can be generated electrochemically include iodine, iodate, periodic acid, hydrogen peroxide, hypochlorite, metavanadate, bromate, dichromate, cerium (IV), and permanganate. Reductants that can be generated electrochemicaily include chromium (II), ferrocyanide, thiols, thiosulfate, titanium (III), arsenic (III) and iron (II). The miscellaneous reagents include bromine, chloride, protons and hydroxyl ions. Among the foregoing reagents, protons, hydroxyl ions, iodine, bromine, chlorine and the thiols are preferred.

Figure 51:
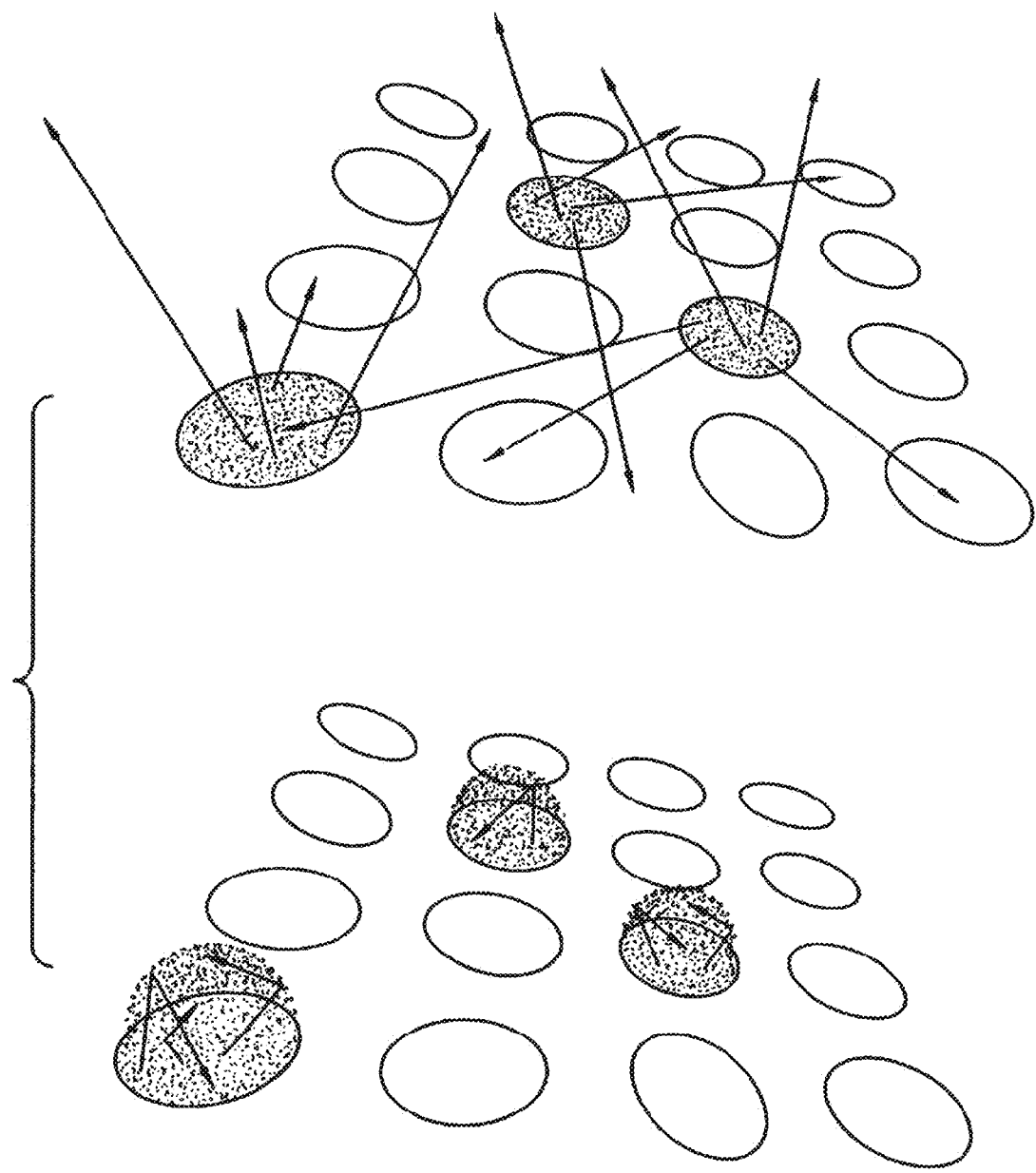
FIG. 51 illustrates how the methods of the present invention function to isolate contaminating ions and thereby prevent chemical cross-talk between neighboring selected electrodes. The buffering and/or scavenging solutions of the present invention alone or combination with a "getter" structure effectively isolate reactive electrochemically generated reagents thereby allowing multiple chemical reactions in close proximity.

In accordance with preferred embodiments of the present invention, a buffering and/or scavenging solution is in contact with each electrode. The buffering and/or scavenging solutions that may be used in accordance with the invention are preferably buffered toward, or scavenge, ions such as protons and/or hydroxyl ions, although other electrochemically generated reagents capable of being buffered and/or scavenged are clearly contemplated. The buffering solution functions to prevent chemical cross-talk due to diffusion of electrochemically generated reagents from one electrode in an array to another electrode in the array, while a scavenging solution functions to seek out and neutralize/deactivate the electrochemically generated reagents by binding or reacting with them. Thus, the spatial extent of excursion of electrochemically generated reagents can be actively controlled by the use of a buffering solution and/or a scavenging solution. This function is graphically explained in FIG. 51. In accordance with the invention, the buffering and scavenging solutions may be used independently or together. Preferably, a buffering solution is used because the capacity of a buffering solution is more easily maintained, as compared with a scavenging solution.

Buffering solutions that can be used in accordance with the present invention include all electrolyte salts used in aqueous or partially aqueous preparations. Buffering solutions preferably used in accordance with the present invention include: acetate buffers, which typically buffer around pH 5; borate buffers, which typically buffer around pH 8;

carbonate buffers, which typically buffer around pH 9; citrate buffers, which typically buffer around pH 6; glycine buffers, which typically buffer around pH 3; HEPES (4-[2-hydroxyethyl]-1pipirazine ethane sulfonic acid) buffers, which typically buffer around pH 7; MOPS (morpholinopropanesulfonic acid) buffers, which typically buffer around pH 7; phosphate buffers, which typically buffer around pH 7; TRIS (tris[hydroxymethyl]amino methane) buffers, which typically buffer around pH 8; and 0.1 M KI (potassium iodide) in solution, which buffers the iodine concentration by the equilibrium reaction $I_2+I^-=I_3^-$, the equilibrium coefficient for this reaction being around $10^2$.

Alternatively, or in combination with a buffering solution, a scavenging solution may be used that contains species such as ternary amines that function as hydroxyl ion scavengers or sulfonic acids that function as proton scavengers in nonaqueous media. The rate at which a reagent/species is scavenged depends both on the intrinsic rate of the reaction occurring and on the concentration of the scavenger. For example, solvents make good scavengers because they are frequently present in high concentrations. Most molecules scavenge in a nonselective way, however, some molecules, such as superoxide dismutase and horseradish peroxidase, scavenge in a selective manner.

Of particular interest to the present invention are scavenger molecules that can scavenge the different reactive species commonly generated, for example, by water hydrolysis at electrodes, including hydroxyl radicals, superoxides, oxygen radicals, and hydrogen peroxide. Hydroxyl radicals are among the most reactive molecules known, their rate of reaction is diffusion controlled, that is, they react with the first reactant/species they encounter. When hydroxyl radicals are generated by water hydrolysis, the first molecule they usually encounter is a water molecule. For this reason, water is a rapid and effective scavenger of hydroxyl radicals. Superoxides are also a relatively reactive species, but can be stable in some nonaqueous or partially aqueous solvents. In aqueous media, superoxides rapidly react with most molecules, including water. In many solvents, they can be scavenged selectively with superoxidase dismutase.

Oxygen radicals are a family of oxygen species that exist as free radicals. They can be scavenged by a wide variety of molecules such as water or ascorbic acid. Hydrogen peroxide is a relatively mild reactive species that is useful, in particular, in combinatorial synthesis. Hydrogen peroxide is scavenged by water and many types of oxidizing and reducing agents. The rate at which hydrogen peroxide is scavenged depends on the redox potential of the scavenger molecules being used. Hydrogen peroxide can also be scavenged selectively by horseradish peroxidase. Another electrochemically generated species that can be scavenged is iodine. Iodine is a mild oxidizing reagent that is also useful for combinatorial synthesis. Iodine can be scavenged by reaction with hydroxyl ions to form iodide ions and hypoiodite. The rate at which iodine is scavenged is pH dependent; higher pH solutions scavenge iodine faster. All of the scavenger molecules discussed above may be used in accordance with the present invention. Other scavenger molecules will be readily apparent to those skilled in the art upon review of this disclosure.

In accordance with the present invention, the buffering solutions are preferably used in a concentration of at least 0.01 mM. More preferably, the buffering solution is present in a concentration ranging from 1 to 100 mM, and still more preferably, the buffering solution is present in a concentration ranging from 10 to 100 mM. Most preferably, the buffering solution concentration is approximately 30 mM. A buffering solution concentration of approximately 0.1 molar, will allow protons or hydroxyl ions to move approximately 100 angstroms before buffering the pH to the bulk values. Lower buffering solution concentrations, such as 0.00001 molar, will allow ion excursion of approximately several microns, which still may be acceptable distance depending on the distance between electrodes in an array.

In accordance with the present invention, the concentration of scavenger molecules in a solution will depend on the specific scavenger molecules used since different scavenging molecules react at different rates. The more reactive the scavenger, the lower the concentration of scavenging solution needed, and vice versa. Those skilled in the art will be able to determine the appropriate concentration of scavenging solution depending upon the specific scavenger selected.

The at least one electrode proximate the substrate of the invention is preferably an array of electrodes. Arrays of electrodes of any dimension may be used, including arrays containing up to several million electrodes. Preferably, multiple electrodes in an array are simultaneously addressable and controllable by an electrical source. More preferably, each electrode is individually addressable and controllable by its own electrical source, thereby affording selective application of different potentials to select electrodes in the array. In this regard, the electrodes can be described as "switchable".

Figure 20:
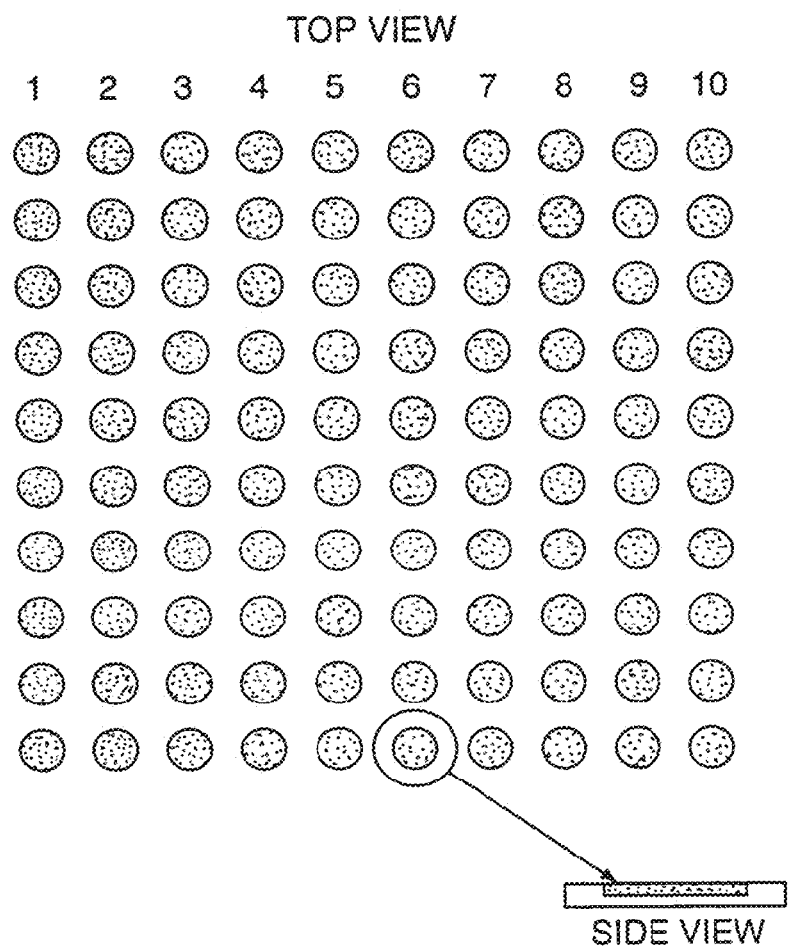
FIG. 20 illustrates a top view diagram of a substrate having at its surface a 10×10 electrode array, having 100 electrodes. A side view of an exemplary electrode at the surface of the substrate is also shown.

The arrays need not be in any specific shape, that is, the electrodes need not be in a square matrix shape. Contemplated electrode array geometries include: squares; rectangles; rectilinear and hexagonal grid arrays with any sort of polygon boundary; concentric circle grid geometries wherein the electrodes form concentric circles about a common center, and which may be bounded by an arbitrary polygon; and fractal grid array geometries having electrodes with the same or different diameters. Interlaced electrodes may also be used in accordance with the present invention. Preferably, however, the array of electrodes contains at least 100 electrodes in a 10×10 matrix. One embodiment of a substrate that may be used in accordance with the present invention having a 10×10 matrix of electrodes is shown in FIG. 20. A side view of an electrode at the surface of the substrate is also shown.

More preferably, the array of electrodes contains at least 400 electrodes in, for example, an at least 20×20 matrix. Even more preferably, the array contains at least 2048 electrodes in, for example, an at least 64×32 matrix, and still more preferably, the array contains at least 204,800 electrodes in, for example, an at least 640×320 array. Other sized arrays that may be used in accordance with the present invention will be readily apparent to those of skill in the art upon review of this disclosure.

Electrode arrays containing electrodes ranging in diameter from approximately less than 1 micron to approximately 100 microns (0.1 millimeters) are advantageously used in accordance with the present invention. Further, electrode arrays having a distance of approximately 10-1000 microns from center to center of the electrodes, regardless of the electrode diameter, are advantageously used in accordance with the present invention. More preferably, a distance of 50-100 microns exists between the centers of two neighboring electrodes.

As shown in the side view of FIG. 20, the electrodes may be flush with the surface of the substrate. However, in accordance with a preferred embodiment of the present invention, the electrodes are hemisphere shaped, rather than flat disks. More specifically, the profile of the hemisphere shaped electrodes is represented by an arctangent function that looks like a hemisphere. Those skilled in the art will be familiar with electrodes of this shape. Hemisphere shaped electrodes help assure that the electric potential is constant across the radial profile of the electrode. That is, hemisphere shaped electrodes help assure that the electric potential is not larger near the edge of the electrode than in the middle of the electrode, thus assuring that the generation of electrochemical reagents occurs at the same rate at all parts of the electrode.

Electrodes that may be used in accordance with the invention may be composed of, but are not limited to, noble metals such as iridium and/or platinum, and other metals, such as, palladium, gold, silver, copper, mercury, nickel, zinc, titanium, tungsten, aluminum, as well as alloys of various metals, and other conducting materials, such as, carbon, including glassy carbon, reticulated vitreous carbon, basal plane graphite, edge plane graphite and graphite. Doped oxides such as indium tin oxide, and semiconductors such as silicon oxide and gallium arsenide are also contemplated. Additionally, the electrodes may be composed of conducting polymers, metal doped polymers, conducting ceramics and conducting clays. Among the noble metals, platinum and palladium are especially preferred because of the advantageous properties associated with their ability to absorb hydrogen, i.e., their ability to be "preloaded" with hydrogen before being used in the methods of the invention.

In accordance with other preferred embodiments of the present invention, one or more of the electrodes are proximate to a "getter" structure. Preferably the "getter" structure comprises a second electrode. The second electrode may be of any shape or size. However, it may function to scavenge electrochemically generated reagents alone or in conjunction with a scavenging solution and/or a buffering solution or it may function to reduce or eliminate diffusion of ions into nearby electric sources such as semiconductor circuitry. Such second electrodes may be made of the same material as the selected electrodes discussed above.

The electrode(s) used in accordance with the invention may be connected to an electric source in any known manner. Preferred ways of connecting the electrodes to the electric source include CMOS switching circuitry, radio and microwave frequency addressable switches, light addressable switches, and direct connection from an electrode to a bond pad on the perimeter of a semiconductor chip. The placement of a "getter" structure in accordance with the description set forth above and such as the structure exemplified in FIGS. 45 and 48-50 effectively prolongs the life of a semiconductor chip thereby making such a connection particularly advantageous.

CMOS switching circuitry involves the connection of each of the electrodes to a CMOS transistor switch. The switch is accessed by sending an electronic address signal down a common bus to SRAM (static random access memory) circuitry associated with each electrode. When the switch is "on", the electrode is connected to an electric source. This is a preferred mode of operation.

Radio and microwave frequency addressable switches involve the electrodes being switched by a RF or microwave signal. This allows the switches to be thrown both with and/or without using switching logic. The switches can be tuned to receive a particular frequency or modulation frequency and switch without switching logic. Alternatively, the switches can use both methods.

Light addressable switches are switched by light. In this method, the electrodes can also be switched with and without switching logic. The light signal can be spatially localized to afford switching without switching logic. This is accomplished, for example, by scanning a laser beam over the electrode array; the electrode being switched each time the laser illuminates it. Alternatively, the whole array can be flood illuminated and the light signal can be temporally modulated to generate a coded signal. However, switching logic is required for flood illumination.

One can also perform a type of light addressable switching in an indirect way. In this method, the electrodes are formed from semiconductor materials. The semiconductor electrodes are then biased below their threshold voltage. At sufficiently low biases, there is no electrochemistry occurring because the electrons do not have enough energy to overcome the band gap. The electrodes that are "on" will already have been switched on by another method. When the electrodes are illuminated, the electrons will acquire enough energy from the light to overcome the band gap and cause electrochemistry to occur.

Thus, an array of electrodes can be poised to perform electrochemistry whenever they are illuminated. With this method, the whole array can be flood illuminated or each electrode can be illuminated separately. This technique is useful for very rapid pulsing of the electrochemistry without the need for fast switching electronics. Direct connection from an electrode to a bond pad on the perimeter of the semiconductor chip is another possibility, although this method of connection could limit the density of the array.

Electrochemical generation of the desired type of chemical species requires that the electric potential of each electrode have a certain minimum value. That is to say, a certain minimum potential is necessary, which may be achieved by specifying either the voltage or the current. Thus, there are two ways to achieve the necessary minimum potential at each electrode: either the voltage may be specified at the necessary value or the current can be determined such that it is sufficient to accommodate the necessary voltage. The necessary minimum potential value will be determined by the type of chemical reagent chosen to be generated. One skilled in the art can easily determine the necessary voltage and/or current to be used based on the chemical species desired. The maximum value of potential that can be used is also determined by the chemical species desired. If the maximum value of potential associated with the desired chemical species is exceeded, undesired chemical species may be resultantly produced.

The substrates prepared in accordance with the present invention will have a variety of uses including, for example, screening large numbers of polymers for biological activity. To screen for biological activity, for example, in the field of pharmaceutical drug discovery, the substrate is exposed to one or more receptors such as antibodies, whole cells, receptors on vesicles, lipids, or any one of a variety of other receptors. The receptors are preferably labeled with, for example, an electrochemical marker, an electrochemiluminescent marker, a chemiluminescent marker, a fluorescent marker, a radioactive marker, or a labeled antibody reactive with the receptor. The location of the marker on the substrate is detected with, for example, electrochemical, fluorescence or autoradiographic techniques. Through knowledge of the sequence of the material at the location where binding is detected, it is possible to determine quickly which sequence binds with the receptor and, therefore, the technique can be used to screen large numbers of peptides.

The present invention can also be used for therapeutic materials development, i.e., for drug development and for biomaterial studies, as well as for biomedical research, analytical chemistry and bioprocess monitoring. An exemplary application of the present invention includes diagnostics in which various ligands for particular receptors can be placed on a substrate and, for example, blood sera can be screened. Another exemplary application includes the placement of single or multiple pre- formed receptor molecules at selected sites on a substrate and, for example, drug screening could be conducted by exposing the substrate to drug candidate molecules to determine which molecules bind to which pre-formed receptor molecules.

Yet another application includes, for example, sequencing genomic DNA by the technique of sequencing by hybridization. Another contemplated application includes the synthesis and display of differing quantities of molecules or ligands at different spatial locations on an electrode array chip and the subsequent performance of dilution series experiments directly on the chip. Dilution series experiments afford differentiation between specific and non-specific binding of, for example, ligands and receptors. Non-biological applications are also contemplated, and include the production of organic materials with varying levels of doping for use, for example, in semiconductor devices. Other examples of non-biological uses include anticorrosives, antifoulants, and paints.

It is specifically contemplated that the present invention may be used for developing materials. Materials may be developed by methods according to the present invention for many purposes including, but not limited to corrosion resistance, battery energy storage, electroplating, low voltage phosphorescence, bone graft compatibility, resisting fouling by marine organisms, superconductivity, epitaxial lattice matching, or chemical catalysis. Materials for these or other utilities may be formed proximate to one or a plurality of electrodes. Alternatively, materials may be formed by modifying the surface of one or a plurality of electrodes by generating reagents electrochemically. Additionally, materials may be formed by modifying the bulk electrode material of one or a plurality of electrodes using electrochemically generated reagents.

It is further contemplated that methods according to the present invention may be used to develop protocols for testing materials. That is, reagents electrochemically generated by methods according to the present invention may be used to test the physical and chemical properties of materials proximate to one or a plurality of electrodes. For instance, skilled artisans may readily develop protocols to evaluate such properties as corrosion resistance, electroplating efficiency, chemical kinetics, superconductivity, electrochemiluminescence and catalyst lifetimes using electrochemically generated reagents in accordance with the present invention.

The present invention will further be clarified and illustrated by the following examples, which are intended to be merely exemplary of the invention.

EXAMPLES

Example 1

Combinatorial Synthesis of the Leu-Enkephalin Epitope
Background

Endorphins are naturally occurring small peptides (including approximately 20-40 amino acids) that bind to opiate receptors in the brain. It has been discovered that most of the activity of endorphins is due to the last five amino acids on the peptides. These terminal pentapeptides are called enkephalins.

The immunofluorescent technique for detecting the Leu-enkephalin epitope follows standard detection protocols. See for example, F. M. Ausubel et al., Short Protocols in Molecular Biology, Third edition, Unit 14, pgs. 14-23 (1995). This assay requires a primary antibody, e.g., the 3-E7 monoclonal antibody, and a secondary antibody-fluorochrome conjugate specific to the source species of primary antibody, e.g., the goat anti-mouse fluorescent conjugate. The 3-E7 antibody is a mouse monoclonal antibody against endorphins that bind to leu-enkephalins. Both of the antibodies for this technique can be obtained from Boehringer Mannheim Biochemicals, Indianapolis, Ind.

For additional information regarding the 3-E7 monoclonal antibody, see, e.g. Meo, Tommaso, et al., "Monoclonal antibody to the message sequence Tyr-Gly-Gly-Phe [SEQ ID NO:5] of opioid peptides exhibits the specificity requirements of mammalian opioid receptors," Proc. Natl. Acad. Sci. USA 80, pp. 4084-4088 (1983).

Preparation of an Electrode Array for Use in Combinatorial Synthesis

A 10×10 platinum electrode array is used, as is shown in FIG. 20. Columns 1 and 10 are used as counter electrodes. The active columns of the array are columns 2, 3, 5, 6 and 7. Columns 4, 8 and 9 are never activated in this synthesis.

The surface of the array is modified with a permeable membrane layer formed from controlled porosity glass (CPG) that is applied to the array by deposition of silicon dioxide under appropriate conditions in the semiconductor manufacturing process. The CPG forms a chemically inert membrane that is permeable to ions. This membrane is functionalized by silanation with chloromethyl silane. The chloromethyl silane groups are further modified by ethylene glycol linker molecules containing ten ethylene glycol moieties by reacting the silanized CPG membrane with a molecule containing ten ethylene glycol moieties and two amino groups at each end. This membrane provides a layer overlaying the surface of the array that is functionalized by amine groups that are, in turn, attached to the CPG matrix via a silane moiety. The diamino ethylene glycol molecules act as linker molecules (spacer groups) between the membrane and the epitope molecules which are formed.

Addition of Protected Functional Groups to the Membrane

Figure 21:
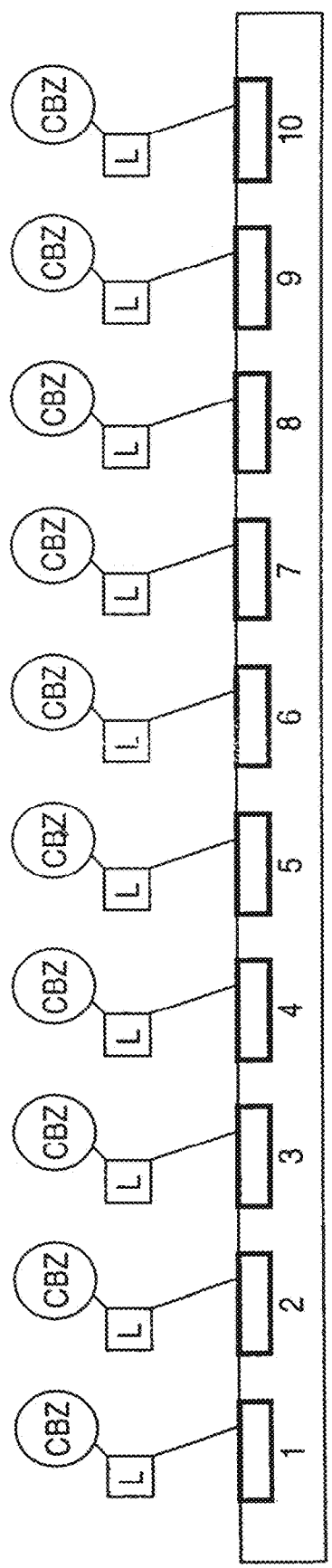
FIG. 21 illustrates a substrate having a permeable attachment layer or membrane having CBZ-protected leucine monomers (L) bonded thereto. The layer/membrane overlays the electrodes at the surface of the substrate.

The functionalized CPG membrane covered electrode array is exposed to a DMF solution of benzyloxycarbonyl (CBZ) protected 1-leucine containing coupling reagents, such as, but not limited to, dicyclohexylcarbodiimide (DCC) or diisopropylcarbodiimide, at room temperature for approximately two hours. This exposure produces a CPG membrane layer covering the array that is completely covered with CBZ-protected 1-leucine moieties attached to the membrane layer by ethylene glycol linker molecules. This moiety covered membrane layer is shown in FIG. 21. This is the bed of molecules on which the epitope molecule is built.

The moiety covered membrane layer is then washed three times with an aqueous 0.1 M phosphate buffer solution having a pH of 7.4.

Removal of the Protecting Groups (Deprotection)

Removal of the CBZ protecting groups from the protected amino acids, i.e., deprotection, using electrochemically generated reagents (protons) is performed as follows.

Referring to the electrode array of FIG. 20, a preconditioning step is performed: columns 2, 3, 5, 6, and 7 are biased negative with respect to columns 1 and 10, which serve as counter electrodes. There is no reference electrode in this system. The potential difference is approximately 3 volts, which voltage is applied for approximately 10 seconds. This preconditioning step causes hydroxyl ions to be formed at the electrodes with a negative bias and protons to be formed at the counter electrodes having a positive bias.

This preconditioning step also causes protons to be reduced to hydrogen molecules at electrodes with a negative bias. The platinum electrodes absorb and hold some of these hydrogen molecules in the bulk metal.

Following the preconditioning step, the bias is then reversed. The electrodes of columns 1 and 10 (counter electrodes) are biased negative with respect to columns 2, 3, 5, 6, and 7. The potential difference is approximately 2.6 volts, which voltage is applied for approximately three seconds. This step causes protons to be formed at the electrodes with a positive bias both from hydrolysis of water and from oxidation of hydrogen molecules that are absorbed into the platinum electrodes during the preconditioning step. As a result of the preconditioning step and this subsequent step, the CBZ protecting groups are removed from the leucine amino acid moieties at the electrodes in columns 2, 3, 5, 6, and 7.

Figure 22:
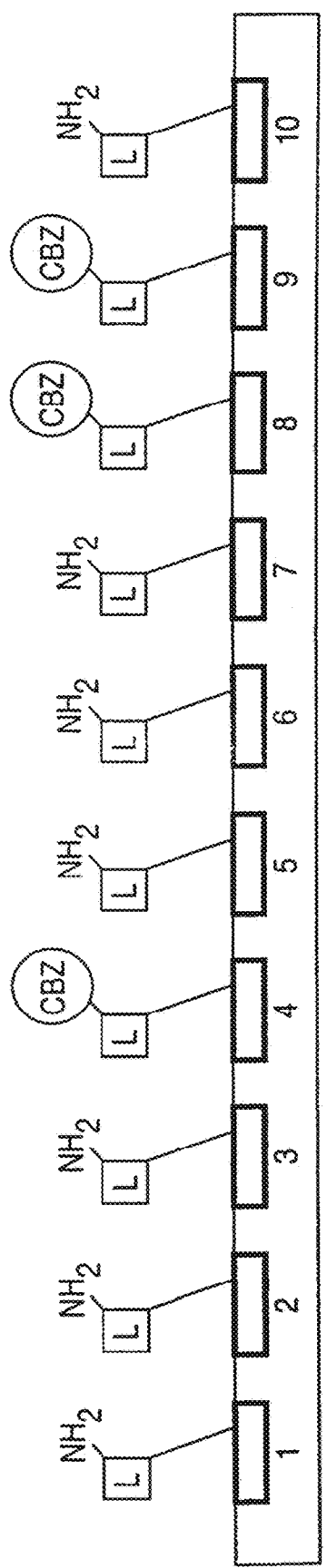
FIG. 22 illustrates a substrate having a permeable attachment layer or membrane overlaying the electrodes at the surface, which layer/membrane contains leucine monomers (L) bearing reactive amine functionalities, e.g., following removal of protecting groups (P.dbd.CBZ) at monomers proximate electrodes 2, 3, 5, 6, and 7 and counter electrodes 1 and 10.

These two steps result in deprotected reactive amine moieties remaining attached to the leucine molecules at these sites (columns 2, 3, 5, 6, and 7) as illustrated in FIG. 22.

Preparation of the Membrane for Coupling

Figure 23:
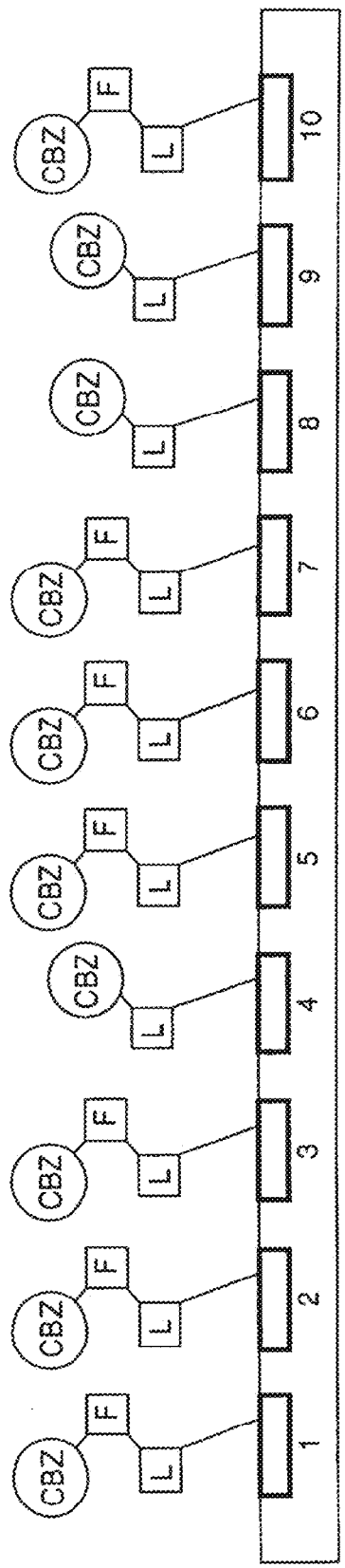
FIG. 23 illustrates modification of monomers proximate electrodes 2, 3, 5, 6, and 7 following CBZ-protected phenylalanine monomers (F) have bonded with the reactive amine functionalities on the leucine monomers proximate these electrodes (a dipeptide is formed).

To prepare the reactive amine moiety covered membrane for coupling CBZ-L-phenylalanine to the deprotected leucine groups, the following steps are performed:

The electrode array containing the reactive amine moiety covered membrane is washed twice with pure DME. The electrode array is then exposed to a DMF solution containing CBZ-L-phenylalanine and coupling reagents, such as DCC at room temperature for approximately two hours. This step results in the electrodes of columns 2, 3, 5, 6, and 7 being modified with an CBZ-protected dipeptide of leucine and phenylalanine. This is shown in FIG. 23.

Figure 24:
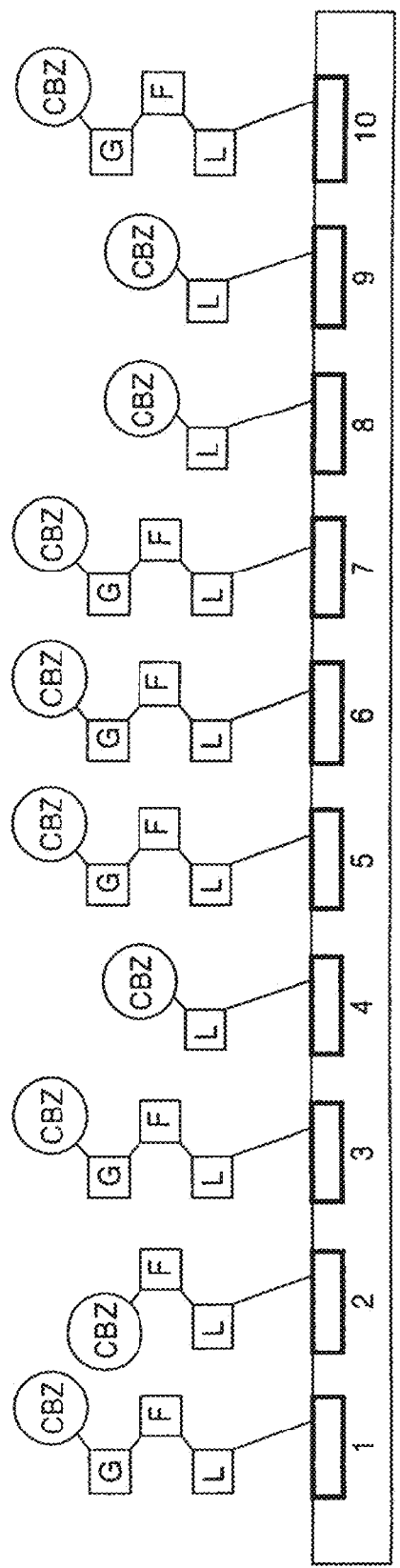
FIG. 24 illustrates modification of the substrate surface by CBZ-protected tripeptides, glycine-phenylalanine-leucine (G-F-L) proximate electrodes 3, 5, 6, and 7.

The deprotection and coupling steps are then repeated at columns 3, 5, 6, and 7. That is, the electrode array is again exposed to an aqueous 0.1 M phosphate buffer solution having a pH of 7.4. The electrode array is then exposed to a DMF solution of CBZ-protected glycine and coupling reagents for approximately 2 hours at room temperature. This results in the electrodes in columns 3, 5, 6, and 7 being modified with the CBZ-protected tripeptide glycine-phenylalanine-leucine (G-F-L [SEQ ID NO:8]), as shown in FIG. 24.

The deprotection and coupling steps are then repeated at columns 5, 6, and 7. That is, the electrode array is again exposed to an aqueous 0.1 M phosphate buffer solution having a pH of 7.4 and then exposed to a DMF solution of CBZ-protected glycine and coupling reagents for approximately two hours at room temperature. This results in the electrodes in columns 5, 6, and 7 being modified with the CBZ-protected tetrapeptide glycine-glycine-phenylalanine-leucine (G-G-F-L [SEQ ID NO:6]).

Figure 25:
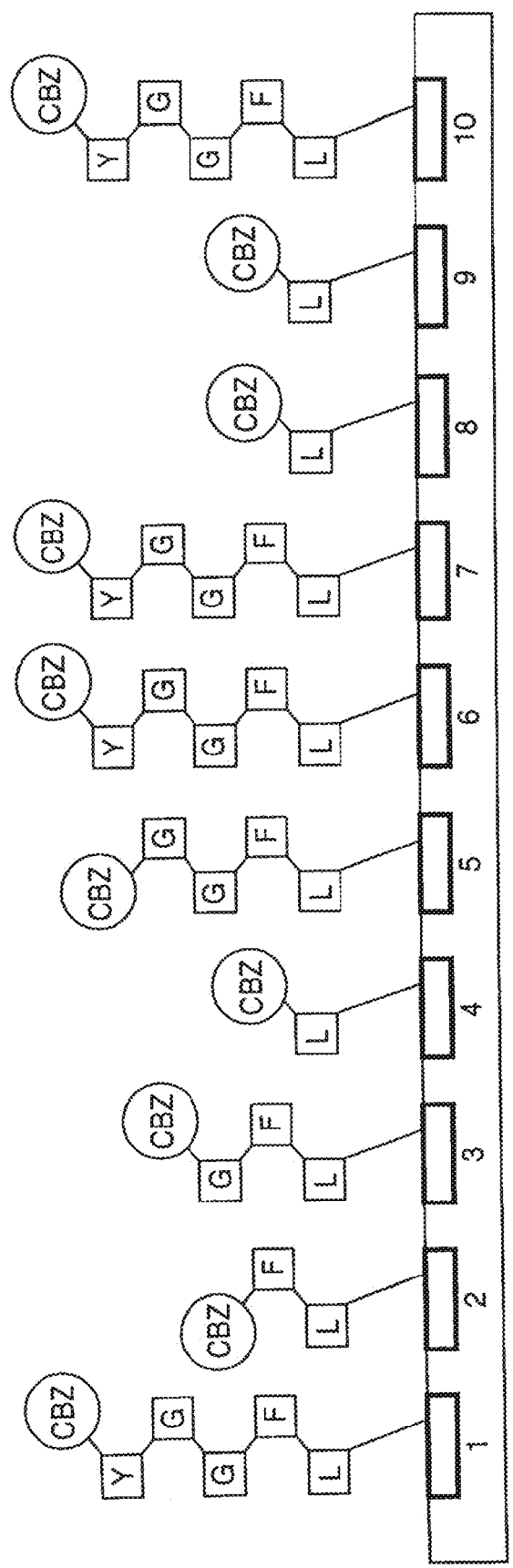
FIG. 25 illustrates modification of the substrate surface by CBZ-protected pentapeptides, tyrosine-glycine-glycine-phenylalanine-leucine (Y-G-G-F-L) (SEQ ID NO:7) proximate electrodes 6 and 7.

The deprotection and coupling steps are then repeated at columns 6 and 7 while the electrode array is again exposed to an aqueous 0.1 M phosphate buffer solution having a pH of 7.4. The electrode array is then exposed to a DMF solution of CBZ-protected 1-tyrosine and coupling reagents for approximately two hours at room temperature. This results in the electrodes in columns 6 and 7 being modified with the CBZ-protected pentapeptide tyrosine-glycine-glycine-phenylalanine-leucine (Y-G-G-F-L [SEQ ID NO:7]), as shown in FIG. 25. This is the CBZ-protected version of the desired Leu-enkephalin epitope.

The deprotecting step is then repeated at columns 2, 3, 5, and 6, without a preconditioning step, to remove the CBZ protecting groups from the terminal amino acids of the combinatorial sequences. This procedure produces the following sequences:

Columns 1 and 10: modified with the protected Leu-enkephalin epitope (these are the counter electrodes).

Column 2: modified with the deprotected dipeptide F-L.

Column 3: modified with the deprotected tripeptide G-F-L [SEQ ID NO:8].

Columns 4, 8 and 9: modified with the CBZ-protected leucine amino acid.

Column 5: modified with the deprotected tetrapeptide G-G-F-L [SEQ ID NO:6].

Column 6: modified with the deprotected Leu-enkephalin epitope.

Column 7: modified with the CBZ-protected Leu-enkephalin epitope.

3-E7 Monoclonal Antibody Assay

Figure 26:
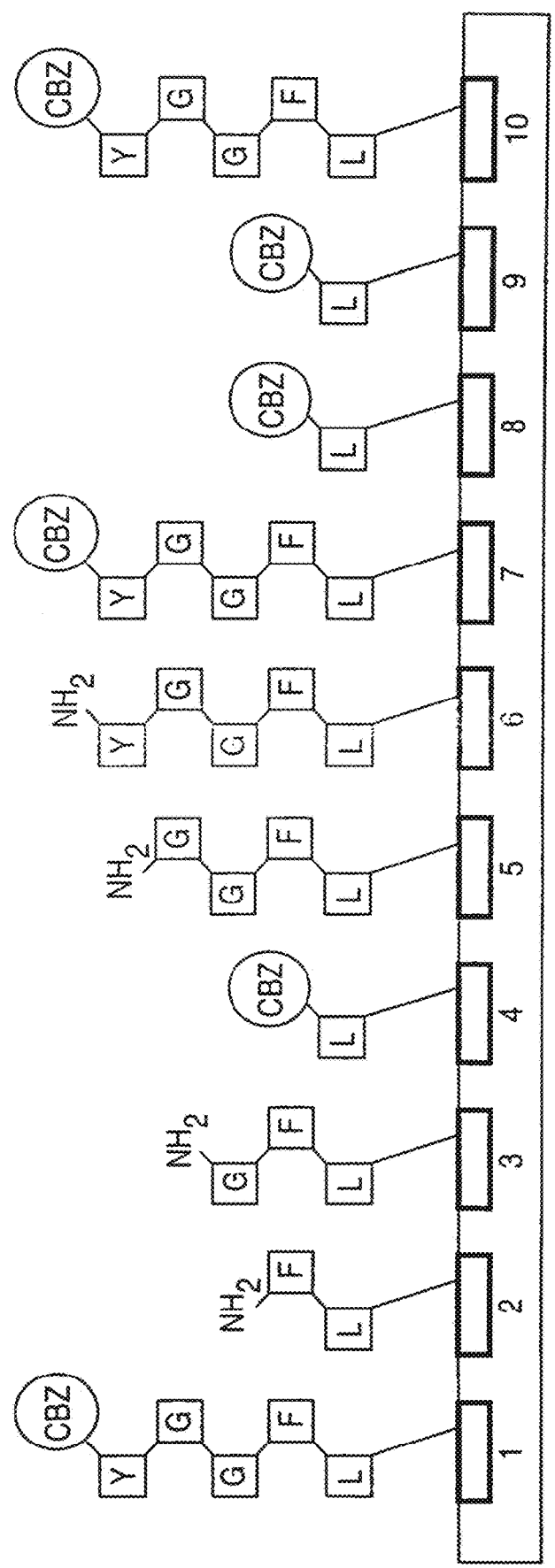
FIG. 26 illustrates a protected leu-enkephalin epitope proximate electrode 7 and counter electrodes 1 and 10, and a deprotected leu-enkephalin epitope proximate electrode 6.
Figure 27:
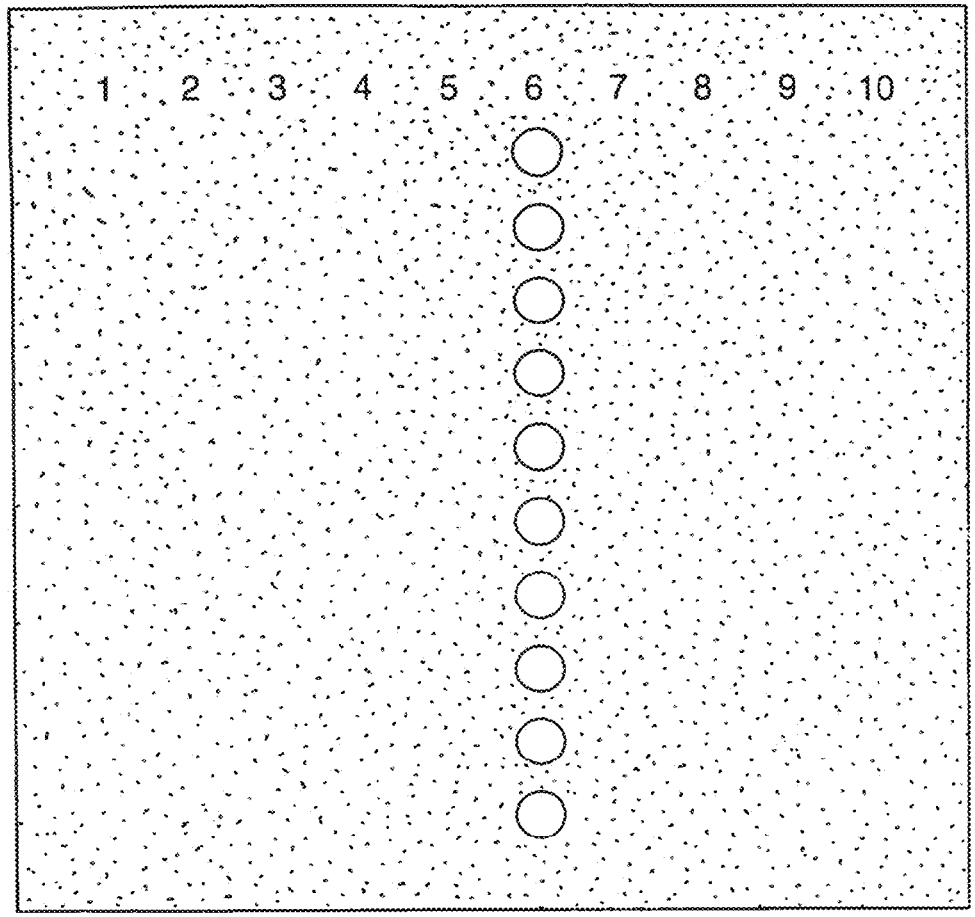
FIG. 27 illustrates representative results as would be observed using an epifluorescent microscope following exposure to the antibody and fluorescent conjugate in accordance with Example 1.

The modified electrode array, i.e., with the 10 modified columns, is exposed, via the Leu-enkephalin epitope detection technique discussed above, to the 3-E7 monoclonal antibody, followed by exposure to the goat anti-mouse fluorescent conjugate. The electrode array is then examined using an epifluorescent microscope. The expected results are shown in FIGS. 26 and 27. As is shown in FIGS. 26 and 27, the active Leu-enkephalin epitope is present proximate to the electrodes of column 6. (Column 6 is the only column modified with the deprotected Leu-enkephalin epitope.)

Note: The synthesis proceeds at the counter electrodes (electrodes 1 and 10) because protons are generated at the counter electrodes during each preconditioning (deprotecting) step. Since a preconditioning step is not performed in the final deprotection step, no protons are produced at the counter electrodes in the final step and a protected Leu-enkephalin epitope is produced at the counter electrodes, which does not react upon exposure to the antibody and fluorescent conjugate.

Example 2

Combinatorial Synthesis of Deoxyribonucleic Acids

Background

The monomer units for combinatorial synthesis of DNA are called phosphoramidites. Phosphoramidites are linked together into a single strand nucleic acid polymer through phosphodiester bonds. Since the phosphorous is protected by a cyanoethyl ether moiety during synthesis, the bonds are phosphotriester bonds. The cyanoethyl group can be removed by a base at the end of synthesis to give the phosphodiester linkage. Phosphoramidites have two ends that are called 3' and 5' ends. The 3' end of one phosphoramidite will couple with the 5' end of another. Usually the 3' end is attached to a solid support and the 5' end is modified by another phosphoramidite to start the synthesis cycle. The 5' end is a hydroxy group that can be protected by a molecule called dimethyltrityl (DMT). DMT groups are acid labile protecting groups.

There are four naturally occurring deoxyribonucleotide monomers that form DNA polymers. They are adenosine (A), thymidine (T), cytosine (C), and guanosine (G). DNA is considered an acid because the phosphodiester groups that bind the monomers together are acidic. The nucleosides (A, T, C, G) are organic bases. DNA in nature is normally tens of millions to billions of base units long. A fifteen base unit long piece of DNA will be prepared in the following example. A piece of DNA of this length is known as a oligonucleotide. DNA molecules should be at least this long, otherwise it is very difficult to distinguish between them.

The nucleosides are protected because the exocyclic amine bases (A, C, G) are susceptible to depurination by acids. The protecting groups on these bases are base labile. There are three kinds of protecting groups on phosphoramidites. They are the DMT groups, which protect the 5' hydroxyl groups, the cyanoethyl ether groups, which protect the phosphorous, and the FOD (fast oligonucleotide deprotection) groups, which protect the exocyclic amines on the nucleoside bases. The DMT groups are acid labile and the others are base labile.

DNA is found in nature mostly as the "duplex" form having the famous double helix structure. This means that two single strands of DNA are bound together by interactions between the nucleoside bases. The nucleoside base T interacts with the nucleoside base A to form an A-T linkage. The nucleoside base C interacts with the nucleoside base G to form a C-G linkage. The A-T and the C-G interactions are the only stable interactions; other combinations are weak. Linkages that are not A-T or C-G can occur, and are called mismatches. When two complimentary single strands of DNA come together to form a duplex, this is called hybridization. When the single strands of DNA in a duplex come apart, the duplex DNA is said to have denatured. DNA duplexes typically denature when they are exposed to heat and/or low ionic strength aqueous solutions.

To determine whether or not a specific DNA sequence has been synthesized at a particular site, one uses probe strands of DNA that are complimentary with the strands that presumably were synthesized at that site. These probe strands are labeled covalently with a fluorescent dye. The probe strands will bind to DNA molecules on the surface with both the correct sequence and the incorrect sequence. However, the melting temperatures are much lower for the DNA duplexes that contain mismatches, i.e., non A-T and C-G link, than those that are complimentary, i.e., A-T and C-G links. Thus, upon heating, the probes forming duplexes with the incorrect DNA strands win denature first. By increasing the temperature to a level where all of the mismatched DNA duplexes have denatured, it is possible to detect only the DNA molecules with the correct sequence by observing the fluorescent dye using epifluorescent microscopy. Alternatively, the test surface can be washed with low ionic strength aqueous solutions. This has the same effect as raising the temperature and is more convenient experimentally.

Synthesis Procedure

The electrode array is first modified with an acrylate/polyvinyl alcohol copolymer layer or membrane. The copolymer layer contains numerous pendant hydroxyl groups that are reactive toward phosphoramidites. The polymer modified electrode array is then exposed to DMT-protected cytidine phosphoramidite and tetrazole at a concentration of 0.05 M in an anhydrous acetonitrile for 30 seconds at room temperature. The cytosine base and all of the other bases used in this example are protected using the FOD protecting scheme. (FOD protecting groups afford the best protection against depurination of exocyclic amines.) The array is then washed with anhydrous acetonitrile. Any unreacted hydroxyl groups on the surface are then capped by exposing the surface to an anhydrous acetonitrile solution of acetic anhydride and 1-methylimidizole for thirty seconds. This results in a surface modified everywhere with DMT protected C base units.

The trivalent phosphite linkage between the polymer and the phosphoramidite is oxidized to the more stable pentavalent phosphotriester linkage by electrochemically generated iodine. The iodine is produced electrochemically by the oxidation of iodide ions in an aqueous THF solution of potassium iodide. Iodine can be confined to the local area where it is formed by both an iodine buffering reaction and a scavenging reaction. Iodine is buffered by an equilibrium reaction with iodide ions to form the triiodide ion. The triiodide ion is not a useful reagent. Further, the solution can be buffered with respect to hydroxyl ions such that it is slightly basic. Iodine reacts with hydroxyl ions to form iodide ions and hypoiodite. Both of these chemical species are unreactive. Thus, hydroxyl ions serve as scavengers for iodine. Because the electrochemical oxidation of iodide ions to iodine can occur under conditions that also produce protons, the local environment can be made acidic while the iodine is being generated. There will be no scavenging in the acidic regions where iodine needs to be active. As a result, there are stable phosphodiester linkages to the polymer film only over those electrodes that electrochemically generate iodine. The unoxidized phosphite linked groups will eventually fall off after repeated exposure to the acetic anhydride capping solution.

The electrode array is next exposed to an aqueous 0.1 M sodium phosphate solution. A positive potential is applied for one second to first selected areas and the DMT protecting groups are removed from the cytidine phosphoramidites in first selected areas. The array is then washed with anhydrous acetic anhydride. The reactive array is then exposed to a 0.05 M solution of thymidine phosphoramidite, T, and tetrazole in anhydrous acetonitrile for 30 seconds. The T nucleotides react with the C nucleotides at the first selected sites to form a C-T dimer. The remaining unreacted C nucleotides are capped and the phosphite linkages are reduced to phosphotriester linkages as outlined above.

This procedure is repeated at second, third, fourth, and so on, selected sites to synthesize combinatorially four different fifteenmer oligonucleotides at selected sites on the array. The array is then exposed to a 0.1 M aqueous ammonium hydroxide solution at 50° C. for an hour. The FOD protecting groups and the cyanoethyl protecting groups on the phosphotriester are removed by the hydroxyl ions. The resulting array consists of single strands of the oligomer nucleic acids bound covalently to the polymer membrane.

Evaluation of the Fidelity of the Array

The fidelity of the combinatorial array is tested using four different fluorescently labeled oligonucleotide probes that are complimentary to the oligonucleotides synthesized on the array. The array is exposed to a first 100 nanomolar solution of a fluorescently labeled oligonucleotide probe in a 0.1 M sodium phosphate buffer at pH 7.2 at room temperature for thirty minutes. The array is then washed three times with a 0.1 M sodium phosphate buffer solution at pH 7.2. The array is then examined with an epifluorescent microscope. Bright spots appear in first areas where the oligonucleotide probe is present To ensure that the oligonucleotide probe and its compliment actually hybridized, the array is washed several times with deionized water at 70° C. for five minutes. Reexamination of the array with the epifluorescent microscope reveals a dark field. This means that the probe hybridized to its compliment and the results are not due to nonspecific absorption. The array is then exposed to a second 100 nanomolar solution of another fluorescently labeled oligonucleotide probe in 0.1 M aqueous sodium phosphate buffer at pH 7.2. The array is subsequently washed, examined with the epifluorescent microscope and then checked for nonspecific absorption. Bright spots appear in the second areas where the nucleotide probes are synthesized. The procedure is repeated for the third and fourth oligonucleotide sequences. The control areas will not bind the fluorescently labeled probe and become bright at any point in the assay.

Example 3 and Comparative Example 4

For the following example and comparative example, results were recorded and reproduced in the form of video photomicrographs that were captured digitally of the respective electrode array chips under various conditions.

Recording of Results—Taking of Pictures

The photomicrographs were taken using an Olympus BX60 microscope with a Pulnix TM-745 integrating CCD camera. The camera was controlled by, and the images were captured by, a Data Translation DT3155 video capture card run by a Pentium-based personal computer. The software that controlled the DT3155 card can easily be written by one of ordinary skill in the art.

Most of the photomicrographs were taken with a 10× objective that allowed approximately 16 electrodes to be seen in each image; however, for purposes of evaluation, the images were sometimes cropped to focus on the activity of the electrodes of interest. At times, a 4× objective was also used. Two types of photomicrographs were taken. A few were taken using white light illumination. In these, the electrodes appear reflective. For example, see FIG. 28. The majority of the photomicrographs were taken using epifluorescent illumination. In these, the electrodes appear dark in the photomicrographs when they are uncoated, i.e., when no fluorescent coating is present, because the metal of the electrodes, e.g., the platinum, quenches any fluorescence present.

Epifluorescent microscopy involves illuminating the electrode array chip from a position above the chip surface, along a path normal to the chip surface. The illuminating beam is filtered to obtain a narrow band centered at the excitation wavelength of the fluorescent dye being used. The fluorescent dye used in the following example and comparative example was Texas Red, which has an absorption maximum at 595 nm. This dye emits a fluorescent light with an emission maximum at 615 nm when it is excited with light of approximately 595 nm. Texas Red can be obtained from Molecular Probes, Eugene Oreg. Filters in the Olympus BX60 microscope prevent the excitation light from traveling to the optical detector of the CCD camera. The Olympus BX60 microscope is equipped with an ancillary art-recognized instrumentation module to perform epifluorescent microscopy using Texas Red dye.

Figure 28:
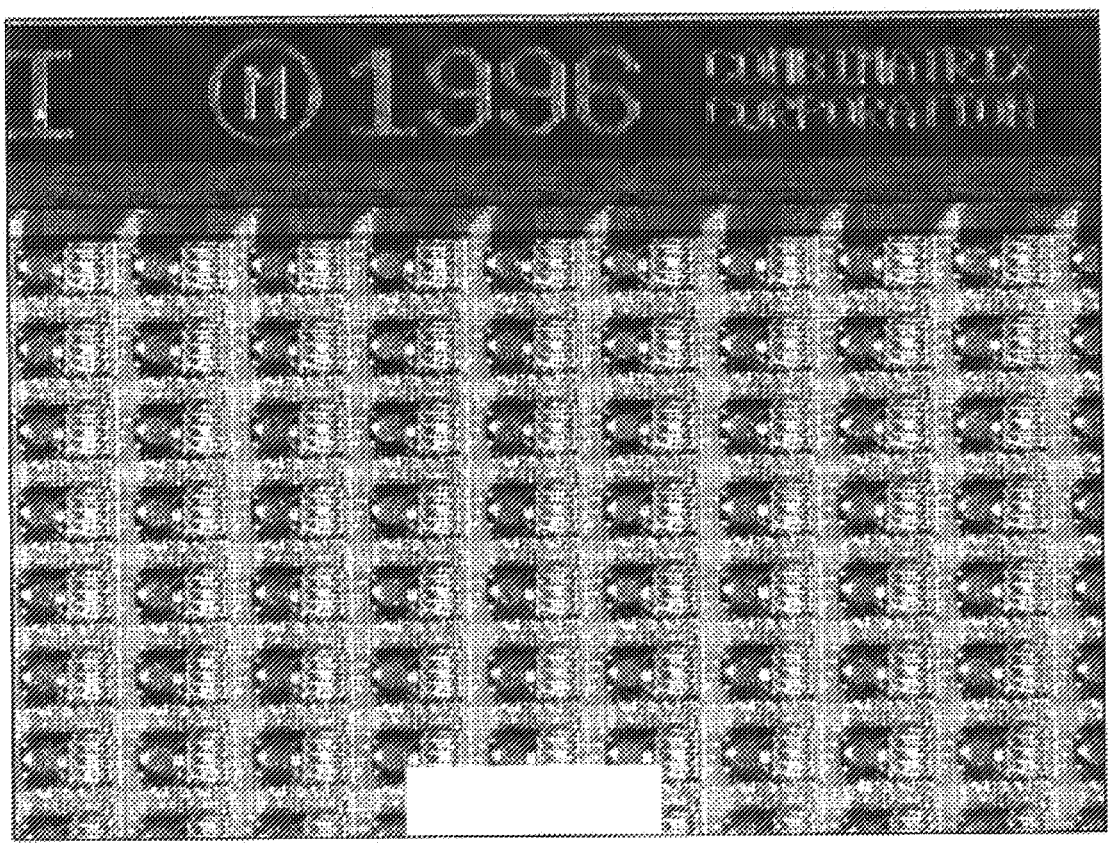
FIG. 28 is a digitally captured white light photomicrograph of an uncoated electrode array chip showing approximately seventy electrodes. This photomicrograph was taken using a 4×objective by an Olympus BX60 microscope with a Pulnix TM-745 integrating CCD camera. Note, there is electrical circuitry associated with these independently addressable electrodes.
Figure 29:
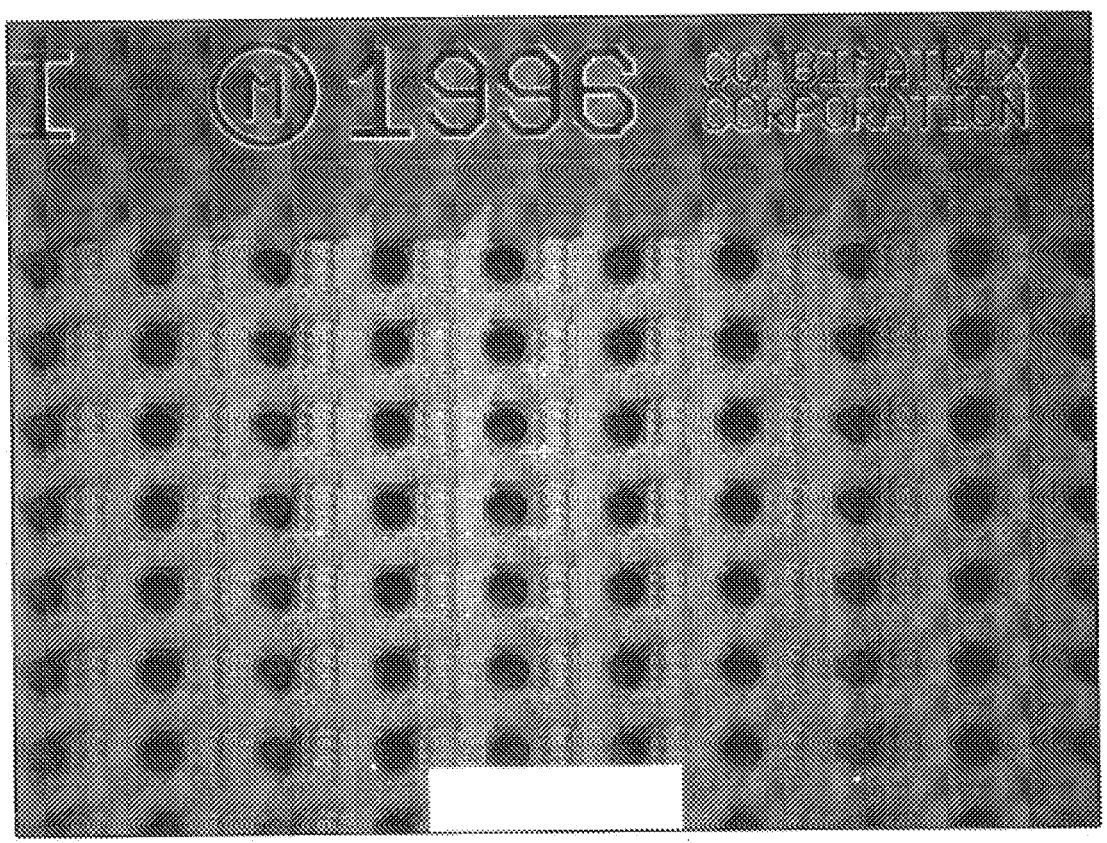
FIG. 29 is a digitally captured epifluorescent photomicrograph of the same array of electrodes pictured in FIG. 28, at the same magnification. This photomicrograph shows that on an uncoated electrode array chip, without any fluorescent coating material thereon, the electrodes are dark. The darkness of the electrodes is explained by the metal of the electrode (platinum) quenching any fluorescence present.
Figure 30:
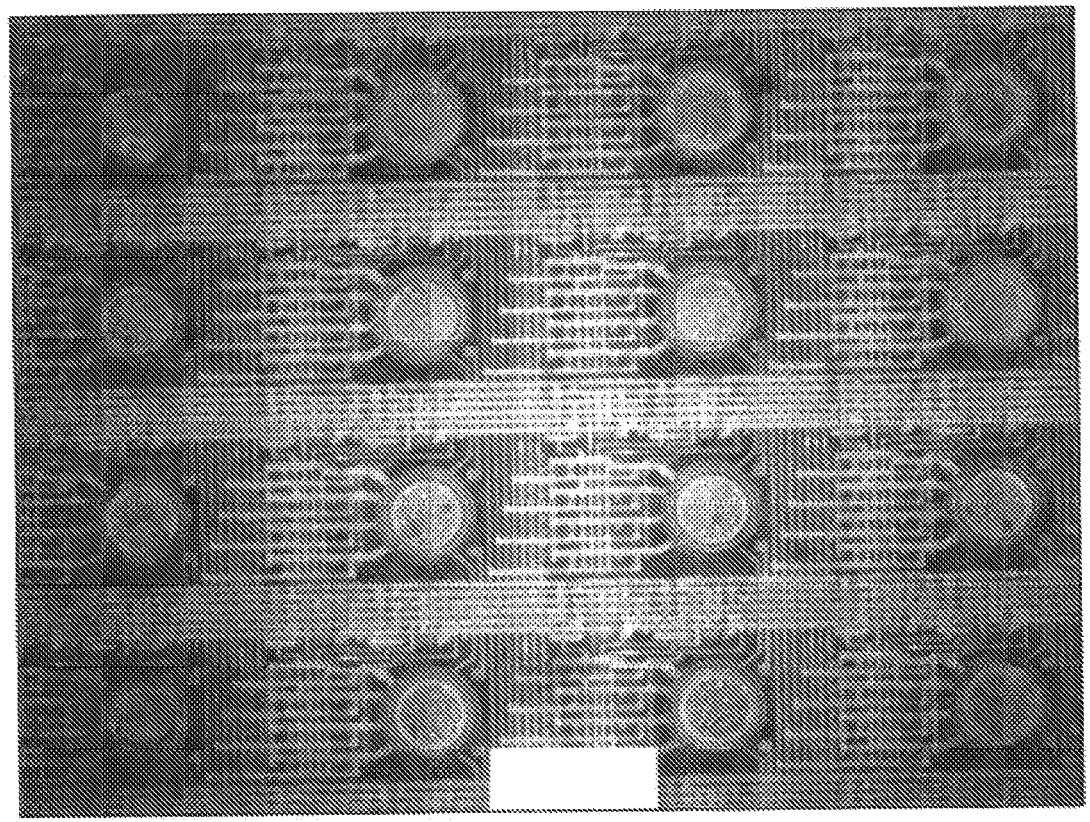
FIG. 30 is a digitally captured epifluorescent photomicrograph of electrodes in the same array as in FIGS. 28 and 29, but taken using a 10×objective and showing only sixteen electrodes. This photomicrograph is of a chip that is coated with a fluorescent membrane material, i.e., there are fluorescent labeled molecules attached to a membrane overlaying the electrodes. This photomicrograph shows that when the electrodes are coated with a membrane containing florescent material, the area proximate/over the electrodes is bright. The fluorescent material used for this photomicrograph was streptavidin molecules labeled with Texas Red dye.

Exemplary photomicrographs taken using white illumination and epifluorescent illumination are shown in FIGS. 28-30. FIGS. 28 and 29 depict an uncoated electrode array chip, while FIG. 30 depicts an electrode array chip coated with a fluorescent membrane.

Description and Preparation of the Electrode Array Chips

The chips prepared and used in the following example and comparative example were rectangular devices with a 16 (in the x-direction) by 64 (in the y-direction) array of 100 micron diameter platinum electrodes. The total number of electrodes in these arrays was 1024. The dimensions of the chips were approximately 0.5 cm (x- direction) by 2.3 cm (y-direction), and the total surface area of the chips was approximately 1 square centimeter. The electrodes in each array were approximately 250 microns apart in the x-direction and approximately 350 microns apart in the y- direction, measured from the center of the electrodes.

Each electrode in the array was capable of being addressed independently using an SRAM cell (static random access memory), a standard art-recognized way to address independently electric circuitry in an array. The SRAM cell was located next to the electrodes in the electrical circuitry associated with electrode. Each electrode in the array had four separate switchable voltage lines that attached to it, allowing each electrode in the array to be switched independently from one voltage line to another. The voltage was arbitrary and was set by an external voltage source.

Figure 31:
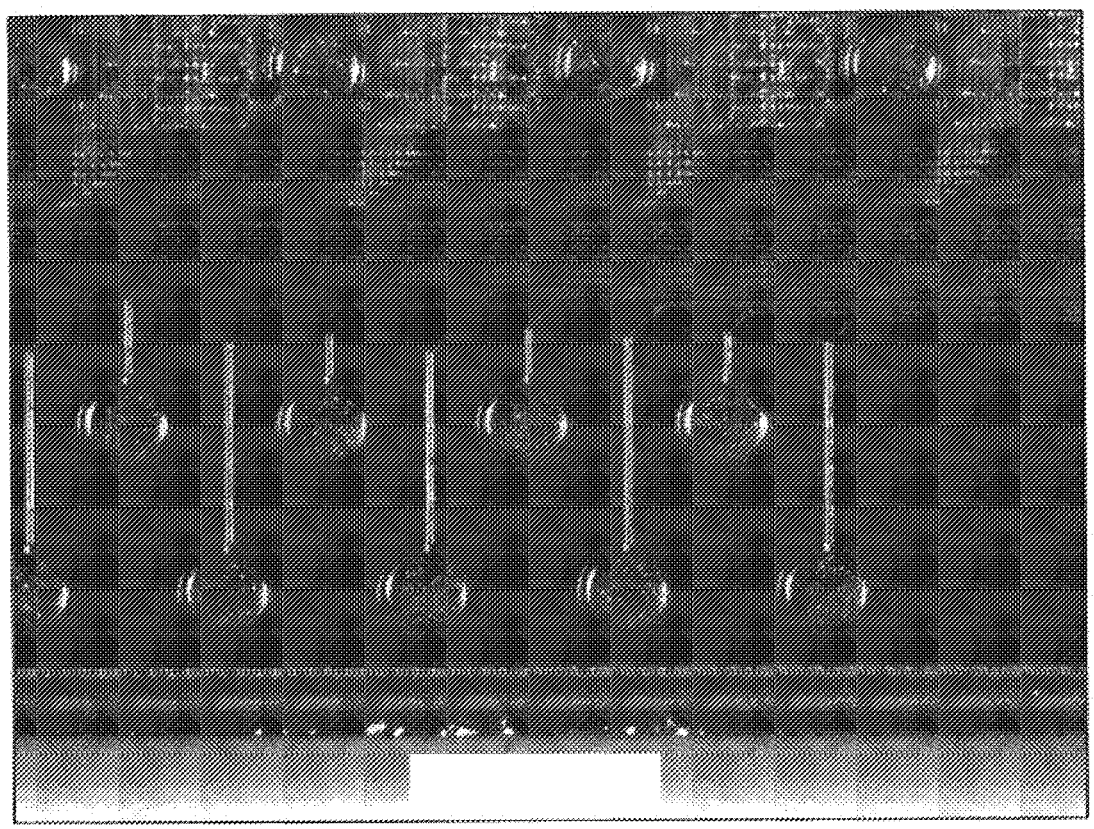
FIG. 31 is a digitally captured white light photomicrograph similar to FIG. 28, except that these electrodes are hard wired, as shown by the leads connecting the electrodes to the electrical source located off the micrograph. In addition, this photomicrograph was taken using a 10×objective. These hardwired electrodes are located on the side of the electrode array chips. Note, there is no circuitry associated with these hard wired-electrodes.

In the chips used in the following example and comparative example, there were additionally 13 electrodes on the side of the chips that were hard wired to bond pads, meaning they were not switchable or independently addressable as were the electrodes in the 16×64 array. These 13 electrodes had no circuitry associated with them except for a single voltage line, and thus allowed protocols to be run-on them without engaging the associated electrode array. These 13 electrodes were 100 microns in diameter and were spaced differently from the electrodes in the array. See, for example, FIG. 31, showing the triangular orientation of the hard-wired electrodes, wherein the electrodes are 250 microns apart from the centers of the electrodes.

The chips were made by a 3 micron process using hybrid digital/analog very large scale integration (VLSI). One skilled in the art would be familiar with such a process and could easily prepare a chip for use in accordance with the present invention. See, Mead, C., Analog VLSI and Neural Systems, Addison/Wesley (1989). The circuitry used was CMOS (complimentary metal-oxide silicon) based and is also well known to those of ordinary skill in the art.

The chips were controlled by at least one Advantech PCL-812 digital I/O card (in the computer) that was driven by a Pentium based personal computer. These digital I/O cards can be obtained from Cyber Research, Branford, Conn. Preferably the chip is connected through interface hardware, i.e., an interface card, to the I/O card. The software for driving the I/O card can easily be written by one of ordinary skill in the art. DC voltage for powering the chips was provided by the PCL-812 and/or a Hewlett-Packard E3612A DC power supply. Voltage for the electrodes was supplied by the PCL-812 card and/or by an external Keithley 2400 source-measure unit.

Figure 32A:
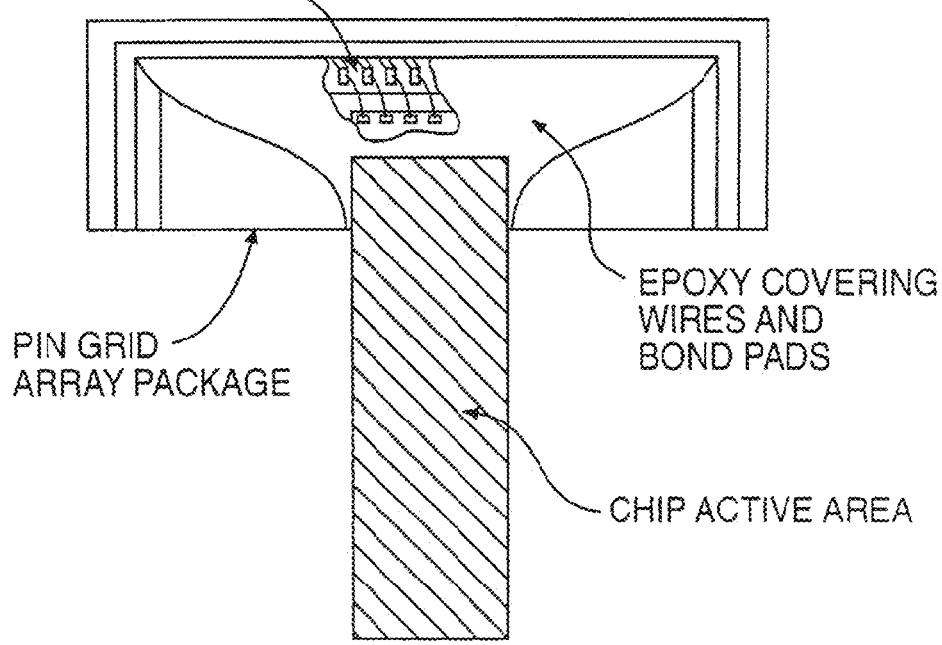
FIGS. 32*a* and 32*b* depict the chip/pin grid array (PGA) package assembly. As is shown in FIG. 32*a*, the chip is attached to the PGA package with glue on the opposite side of the chip from the active area (active area is the area having electrodes at its surface), which leaves the active electrode area protruding from the end of the PGA package in a manner that allows the active area of the chip to be dipped or immersed into solutions. The electrical wires that connect the bond pads on the chip to the bond pads on the PGA package are encased in epoxy. The pins shown in FIG. 32*b* are located on the opposite side of the PGA package shown in FIG. 32*a*.
Figure 32B:
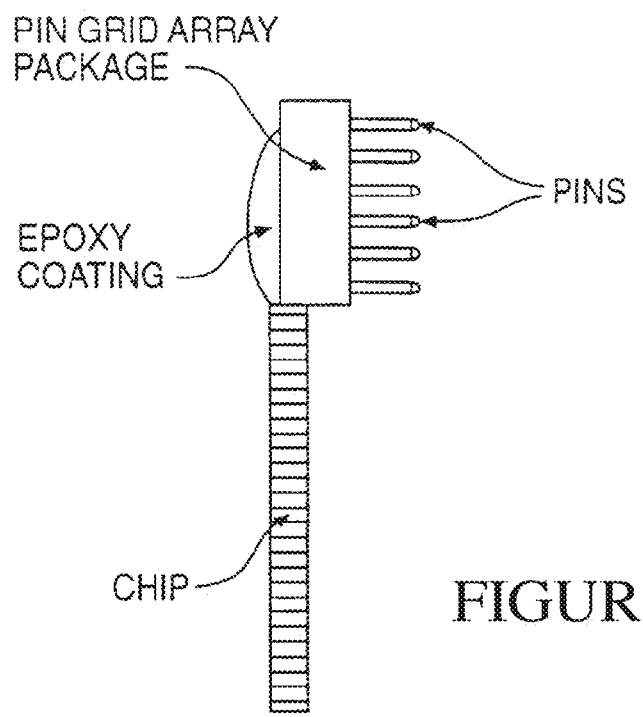

The electrode array chips were designed so that the bond pads for all of the on- chip circuitry were located at one end of the long side of the chips. See FIGS. 32a and 32b. The chips were attached to a standard 121 pin PGA (pin grid array) package that had been sawn in half so that approximately 2 cm of the chip extended out from the end, analogous to a diving board. See FIG. 32b. PGA packages can be obtained from Spectrum Semiconductor Materials, San Jose, Calif. Connecting wires ran between the bond pads on the chip and the contacts (bond pads) on the PGA package. The bond pads on the chip, the connecting wires, and the contacts on the PGA package were covered with epoxy for protection and insulation. See cut away in FIG. 32a. The section of the chips that extended into the air contained the electrode array and was not covered by epoxy. This section of the chips was available for dipping into solutions of interest for chemical synthesis at the electrodes at the surface of the chip. One of ordinary skill in the art could easily set up and design chips appropriate for use in accordance with the present invention.

Example 3 (Inventive)—Deprotection and Localization

Background Description

One of the above described electrode array chips comprising 16×64 platinum electrodes was used for this example. As indicated above, the chip contained 13 hardwired electrodes located at one end of the long side of the chip, however, these hardwired electrodes were not involved in this example.

The model chemical system used in this example to demonstrate localization and selective deprotection using electrochemically generated reagents involved attaching fluorescent labeled streptavidin molecules, a well-known variety of avidin, obtainable from Vector Laboratories, Burlingame, Calif., to a membrane overlaying the electrode array chip via a trityl linker molecule. The overlaying membrane used was polysaccharide-based. The trityl linker molecule used was acid labile, i.e., labile to protons, and detached from the overlaying membrane in the presence of protons, taking with it the attached fluorescent labeled streptavidin molecule. More specifically, the trityl linker molecule used was a modified 4,4'-dimethoxytrityl molecule with an exocyclic active ester obtained from Perseptive Biosystems, Framingham, Mass.

Experimental Procedure
Preparation of the Chip for Attachment of Molecules

To enable the attachment of molecules, in particular trityl linker molecules, to the surface of the electrode array chip for synthesis and/or deprotection proximate the electrodes, the chip was coated/modified with an overlaying membrane of a polysaccharide-based material. Specifically, a polygalactoside was used as the overlaying membrane material in this example. The polygalactoside membrane was dip coated onto the chip. However, dipping or coating according to any method known to one of ordinary skill in the art would be acceptable.

Attachment of the Trityl Linker Molecules

Once the electrode array chip was coated with the polysaccharide membrane, the trityl linker molecules were attached to the chip. The trityl linker molecule used for this example was a modified 4,4'-dimethoxytrityl molecule with an exocyclic active ester, specifically the molecule was N-succininimidyl-4[bis-(4-methoxyphenyl)-chloromethyl]-benzoate. The synthesis and use of this molecule is described in A Versatile Acid-Labile Linker for Modification of Synthetic Biomolecules, by Brian D. Gildea, James M. Coull and Hubert Koester, Tetrahedron Letters, Volume 31, No. 49, pgs 7095-7098 (1990).

The trityl linker molecules were attached to the polysaccharide membrane via immersion of the polysaccharide membrane coated chip in a DMF solution containing 0.5M of tertbutyl ammonium perchlorate, 0.75M of 2,4,6-collidine and 0.2M of the trityl linker. The immersion of the polysaccharide membrane coated chip in the DMF linker solution lasted for 30 minutes at ambient temperature. The trityl linker coated chip was then washed with DMF to remove any remaining reactants. Next, the trityl linker coated chip was washed in an aqueous 0.1 M sodium phosphate buffer that was adjusted to pH 8.0, and dried.

Attachment of the Fluorescent Dye Labeled Molecules

The trityl linker coated chip was then immersed in an aqueous solution of fluorescent dye (Texas Red) labeled streptavidin molecules having a concentration of 50 micrograms per milliliter and allowed to remain in this solution for one hour at ambient temperature. During this immersion, the linker molecule was derivatized and the fluorescent dye labeled streptavidin molecules were attached to the linker molecules.

The chip containing fluorescent dye labeled streptavidin molecules was then washed with an aqueous 0.1M sodium phosphate buffer that was adjusted to pH 8.0 to remove remaining reactants, and dried. The chip was now ready for use in the electrochemical process of the invention, i.e., the selective deprotection step.

Figure 33A:
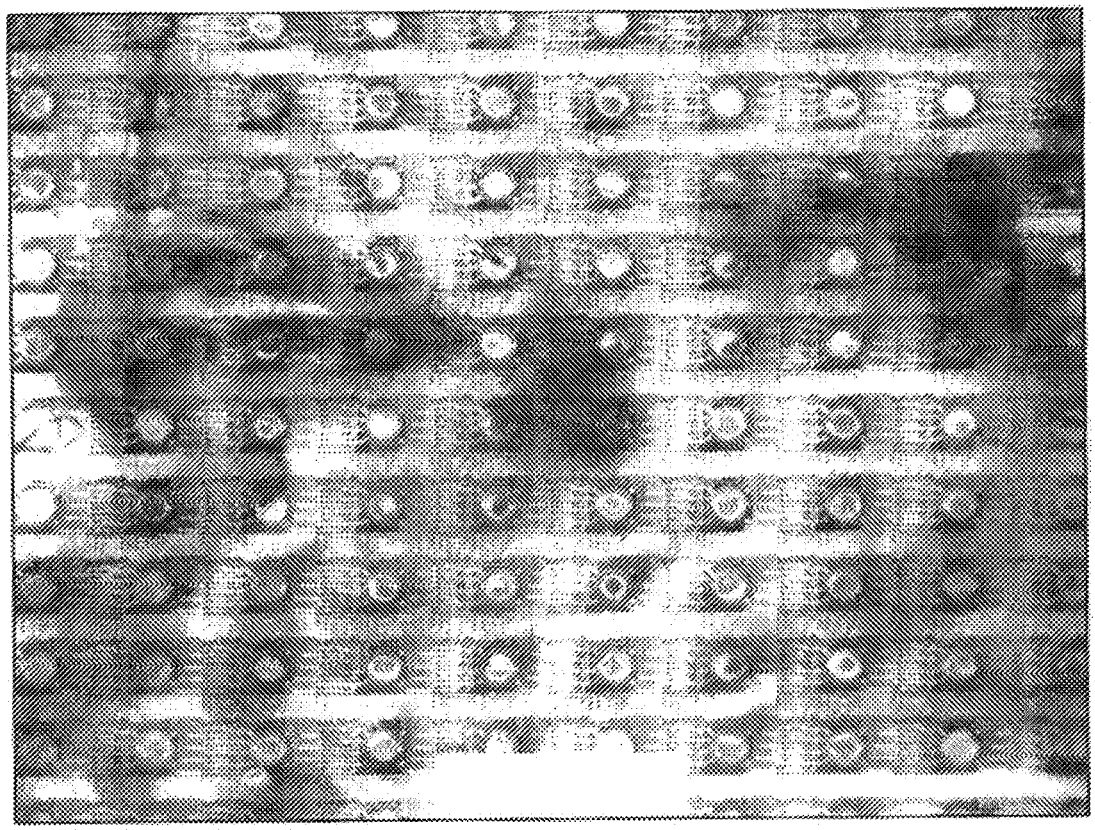
FIGS. 33*a* and 33*b* represent digitally captured epifluorescent photomicrographs showing an electrode array chip before (FIG. 33*a*) and after (FIG. 33*b*) application of voltage and performance of a deprotection step. Prior to application of any voltage, a 0.05M aqueous sodium phosphate buffer at a pH of 8.0 was placed in contact with all the electrodes of the array to enable production of electrochemical reagents.
Figure 33B:
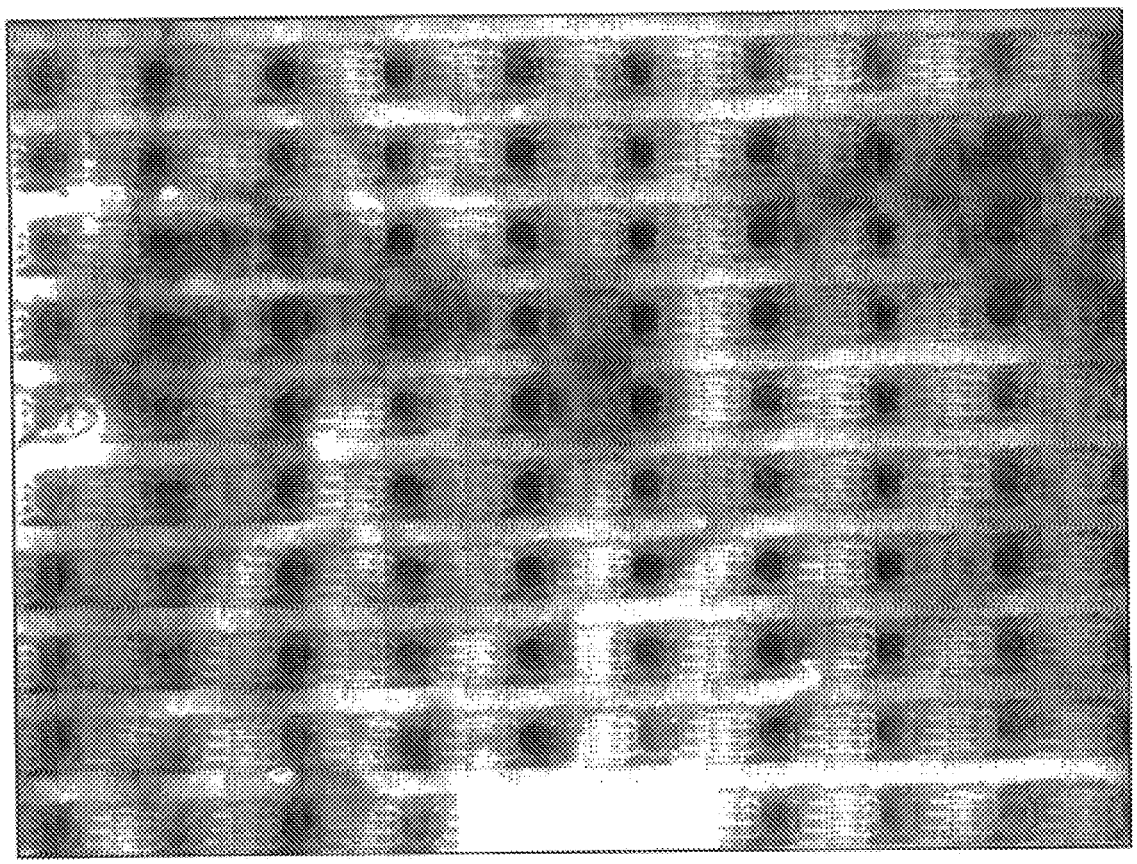

Following exposure of the prepared chip to the fluorescent labeled streptavidin molecules, but prior to any electrical current or voltage being applied, the electrodes in the array were all bright with fluorescence because the membrane proximate to them contained the fluorescent labeled streptavidin molecules bound to the membrane via the trityl linker. A photomicrograph of this is shown in FIG. 33a.

Selective Deprotection

To perform the selective deprotection step, the prepared chip was immersed in a 0.05M aqueous sodium phosphate buffer solution to enable electrochemical generation of reagents. A voltage difference of 2.8 volts was applied to select electrodes (alternating in a checkerboard pattern) for approximately 10 minutes, causing protons to be generated electrochemically at the anodes.

After the protons were electrochemically generated at the anodes, the anodes became dark because the trityl linker previously bound proximate to the anodes dissociated from the anodes and the fluorescent labeled streptavidin molecules were washed away. The extent to which this occurred at the anodes and not at the cathodes in the checkerboard pattern, is a measure of the chemical crosstalk occurring between the electrodes in the array. That is, if chemical crosstalk were occurring, the cathodes would also be dark because the protons would have migrated and dissociated the trityl linkers at the cathodes.

Thus, under epifluorescent microscopy, the bright electrodes (cathodes) indicate the presence of a Texas Red labeled streptavidin molecule bound to a linker molecule at the electrode and the dark electrodes (anodes) indicate the lack of a Texas Red labeled streptavidin molecule bound to a linker molecule at the electrode. This is shown in FIGS. 34 and 35, FIG. 34 having been taken using a 4× objective with an integration time of 2 seconds, and FIG. 35 having been taken using a 10× objective with a 500 millisecond integration time.

Results

Figure 34:
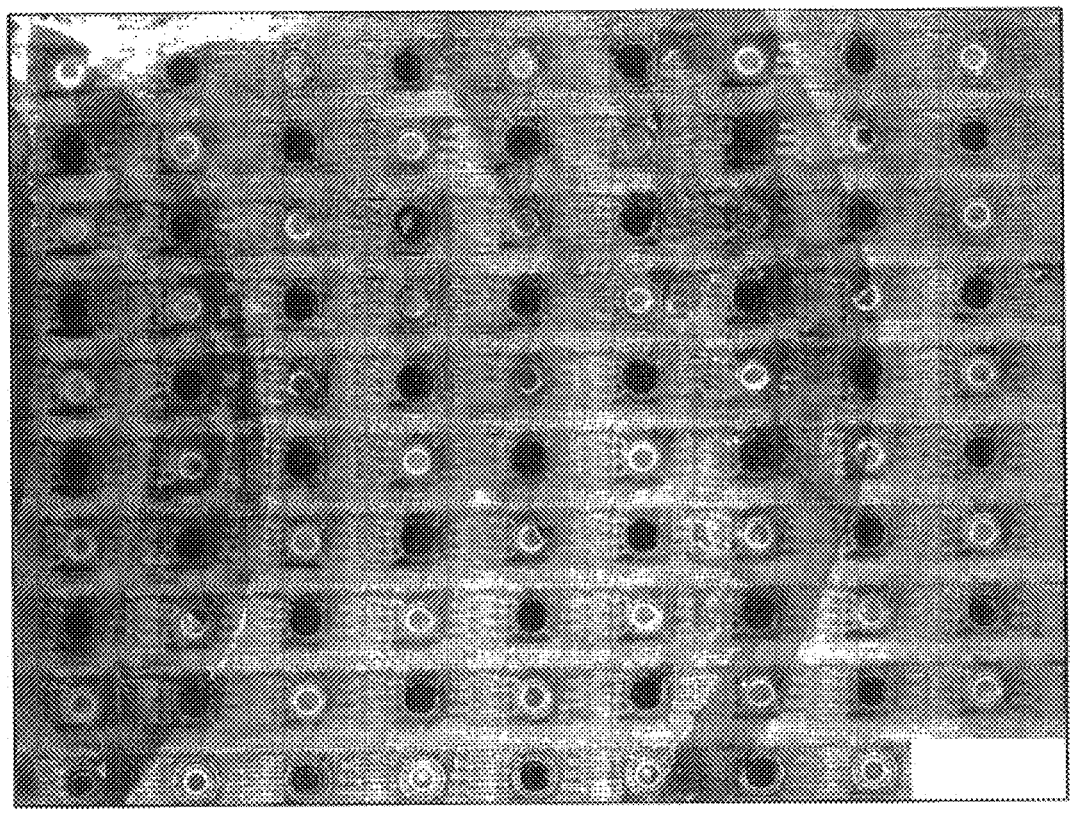
FIG. 34 represents a digitally captured epifluorescent photomicrograph showing a hardwired electrode array chip wherein the anodes (the dark electrodes) and the cathodes were alternating electrodes. The depicted checkerboard pattern was obtained following application of 2.8 volts for 10 minutes. The objective used to obtain this photomicrograph was 4× and the integration time was 1 second. Note, the localization of the acid at the anodes. The precision of the localization achieved in accordance with the present invention allowed the checkerboard pattern to be obtained.
Figure 35:
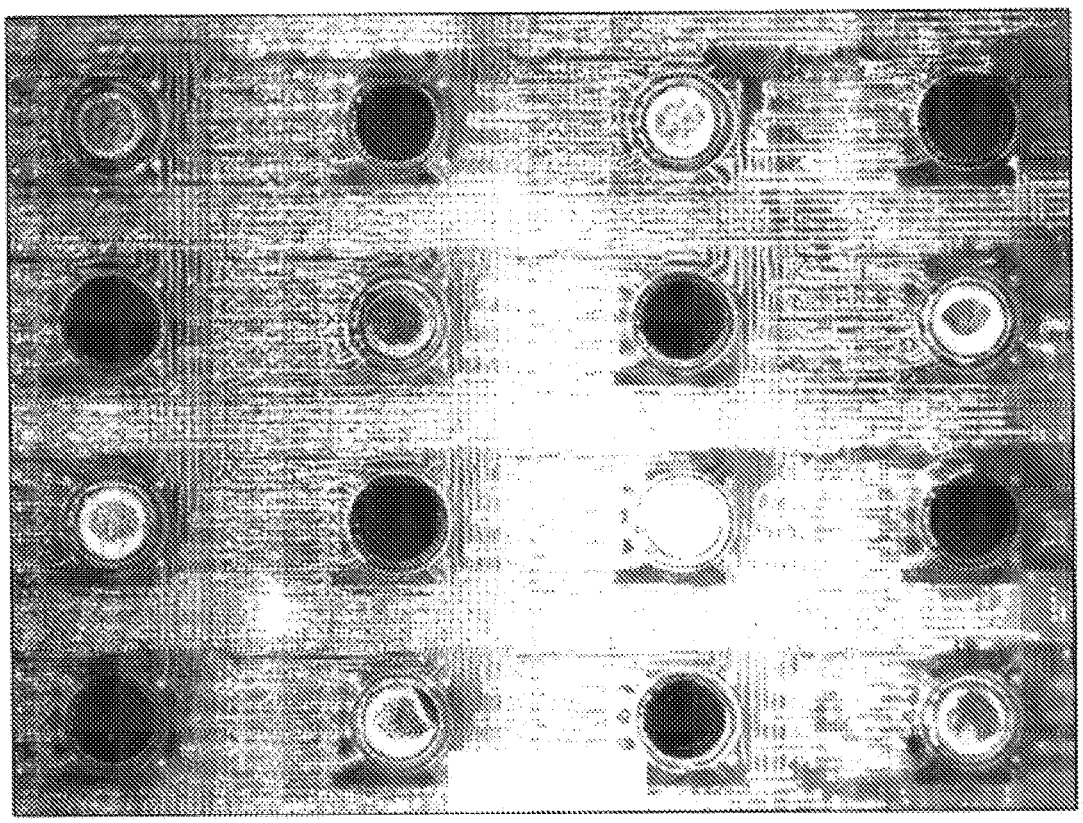
FIG. 35 represents a digitally captured epifluorescent photomicrograph showing the same hardwired electrode array chip as in FIG. 34, but this photomicrograph was taken using a 10× objective with a 700 millisecond integration time.

Following drying of the chip, photomicrographs were taken of the electrode array following completion of the deprotection step, and are reproduced in FIGS. 34 and 35. As shown in these figures, selective deprotection was achieved using the process of the present invention. As is shown in these figures, a repeating checkerboard pattern was produced, exemplifying that the process of the present invention achieved localization of the protons generated at the anodes and prevented migration of these protons to the cathodes. The dark areas (anodes) are clearly defined and distinguished from the also clearly defined bright areas (cathodes). The clearly demarcated checkerboard pattern shown in the photomicrographs indicates that no, or very little, chemical cross talk occurred during the deprotection step.

Example 4

Comparative Example

Using two electrode array chips prepared in accordance with the present invention, one chip was processed using the selective deprotection procedure in accordance with the present invention using a buffering solution, and the second chip was processed using a selective deprotection procedure varying only in that the electrolyte used in the Examples of Southern (WO 93/22480, held Nov. 11, 1993) replaced the buffering solution of the present invention.

Rather than using an electrode array, this comparison was conducted on a few of the hard wired electrodes found on the side of the electrode array chips. FIG. 31 is a photomicrograph taken under the same conditions as FIG. 28, but showing the hard wired electrodes used in this example.

Deprotection in Accordance with the Invention

The steps of coating the chip with the polysaccharide membrane and attaching the trityl linker molecules to the membrane were performed in accordance with the procedures used above in Example 3.

The attaching of the fluorescent dye labeled streptavidin molecules and the deprotection steps were also performed in accordance with Example 3, but a 20 mM aqueous sodium phosphate buffer solution was used instead of the 0.05M solution used in Example 3, to enable the electrochemical generation of reagents. The voltage that was applied between selected electrodes was 2.8 volts, which was applied for approximately 30 seconds.

Similar results to Example 3 were obtained. These results are shown in FIGS. 36-38.

Figure 36:
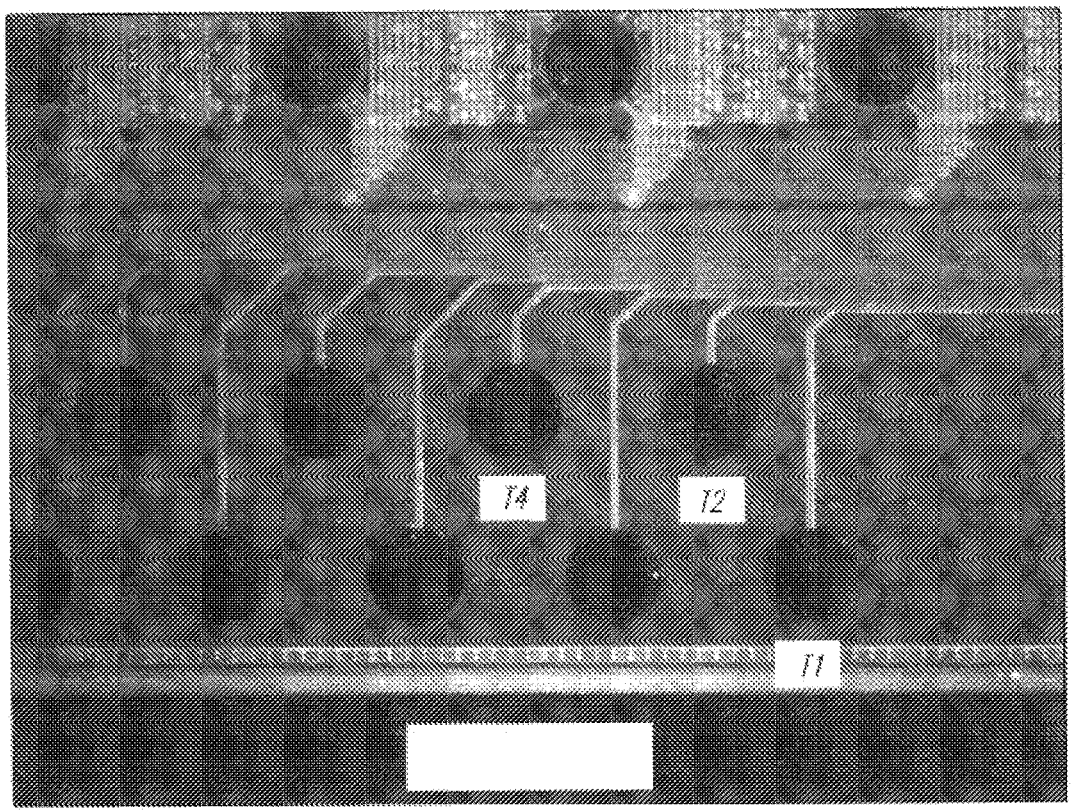
FIG. 36 is a digitally captured epifluorescent photomicrograph of an uncoated electrode array chip showing an array of hardwired electrodes. (The neighboring electrode array is also shown in this figure.) The orientation of the array shown allows accurate reading of the brightness of the electrodes. The electrodes shown are dark. The three electrodes to which electrical connection was provided, and of which brightness or darkness observations were made, are labeled "T1", "T2", and "T4".

FIG. 36 shows the hardwired electrodes involved in this process, labeled as T1, T2 and T4. In this process, T1 was the counter electrode, i.e., the cathode, and T2 and T4 were the anodes where protons were generated upon the application of the electric current or voltage. No voltage had been applied to the electrodes shown in FIG. 36.

Figure 37:
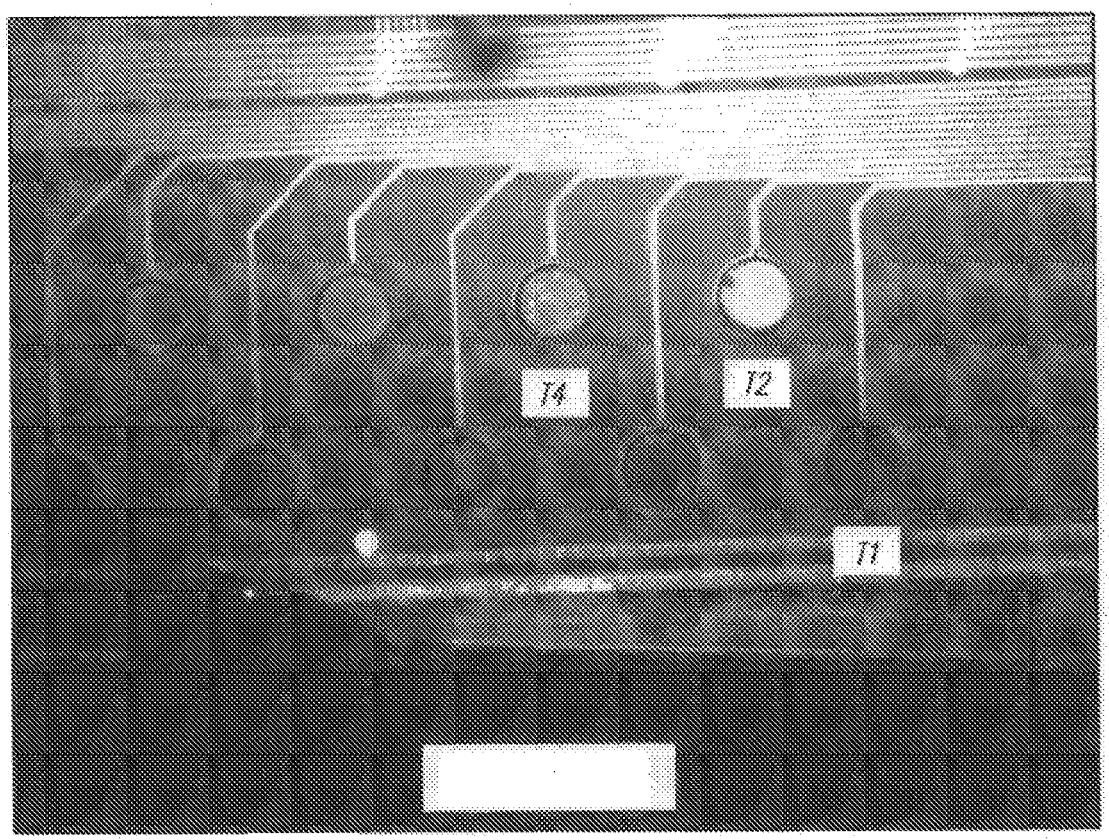
FIG. 37 is a digitally captured epifluorescent photomicrograph of a chip that is coated with a fluorescent membrane containing Texas Red labeled streptavidin molecules that are attached to the electrodes via trityl linker molecules. Electrodes T2 and T4 have a strong bright signal. Electrode T1 is dark. No voltage has been applied to the electrodes yet.

FIG. 37 shows the same electrodes following derivatization or bonding with the fluorescent labeled streptavidin molecules. As is shown, electrodes T2 and T4 are bright, indicating the presence of a Texas Red labeled streptavidin molecule bound to a linker molecule proximate each of these electrodes.

Figure 38:
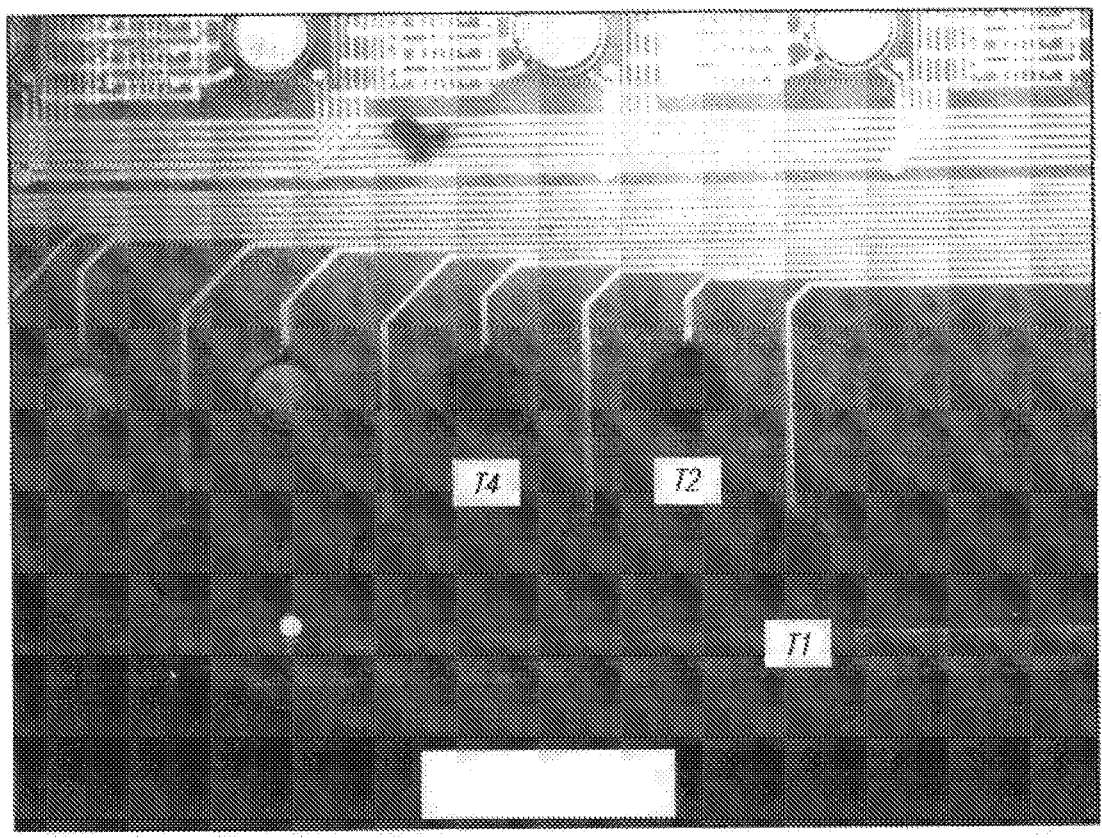
FIG. 38 is a digitally captured epifluorescent photomicrograph of the chip shown in FIG. 37 after positive voltage has been applied to electrodes T2 and T4. Positive voltage produced protons at these electrodes. Electrodes T2 and T4 are dark because the trityl linker molecule has dissociated from the membrane overlaying the electrodes. Electrode T1 was used as the counter electrode. Note that the dark areas are confined to electrodes T2 and T4, i.e., there is very little chemical cross talk occurring between neighboring electrodes.
Figure 39A:
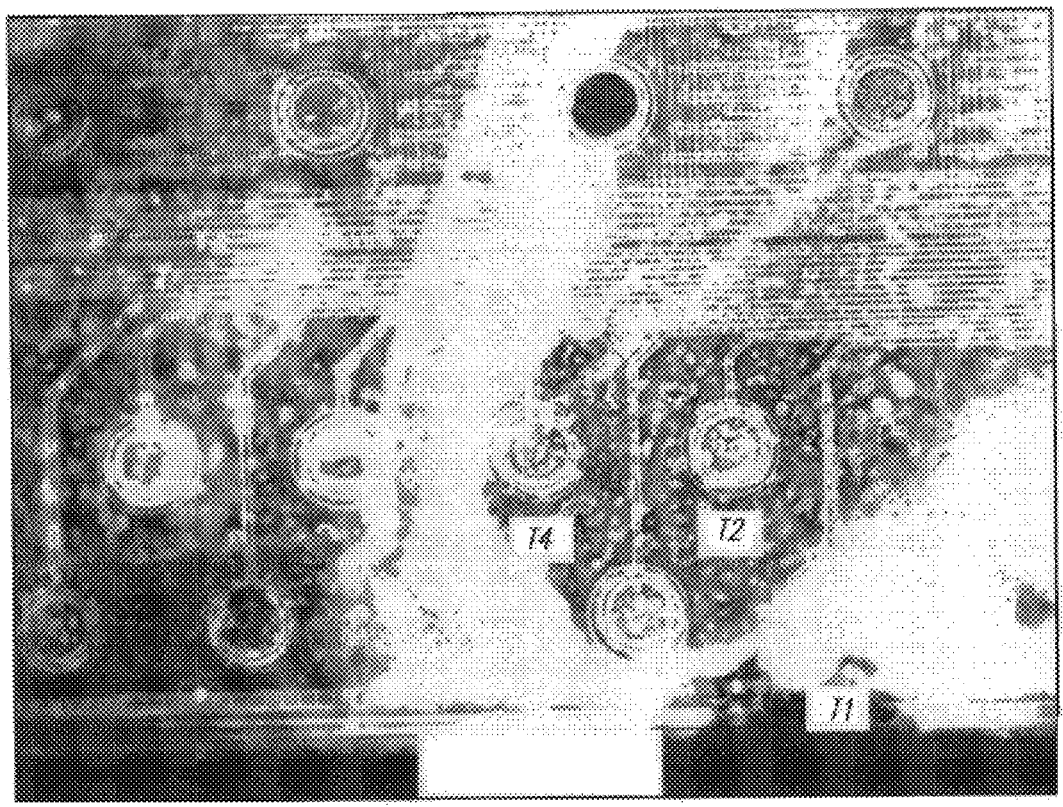
FIGS. 39a and 39b represent digitally captured epifluorescent photomicrographs showing hardwired electrodes before (FIG. 39a) and after (FIG. 39b) a deprotection step performed in accordance with the reaction conditions, i.e., electrolyte, of the prior art, Southern WO 93/22480. These photomicrographs, taken through a 10× objective, show the imprecision and randomness caused by "chemical crosstalk" between the electrodes. The large areas of black-out and white-out surrounding the electrodes in these photomicrographs represent the excursion of the electrochemical reagents (protons) away from the electrode at which they were generated.
Figure 39B:
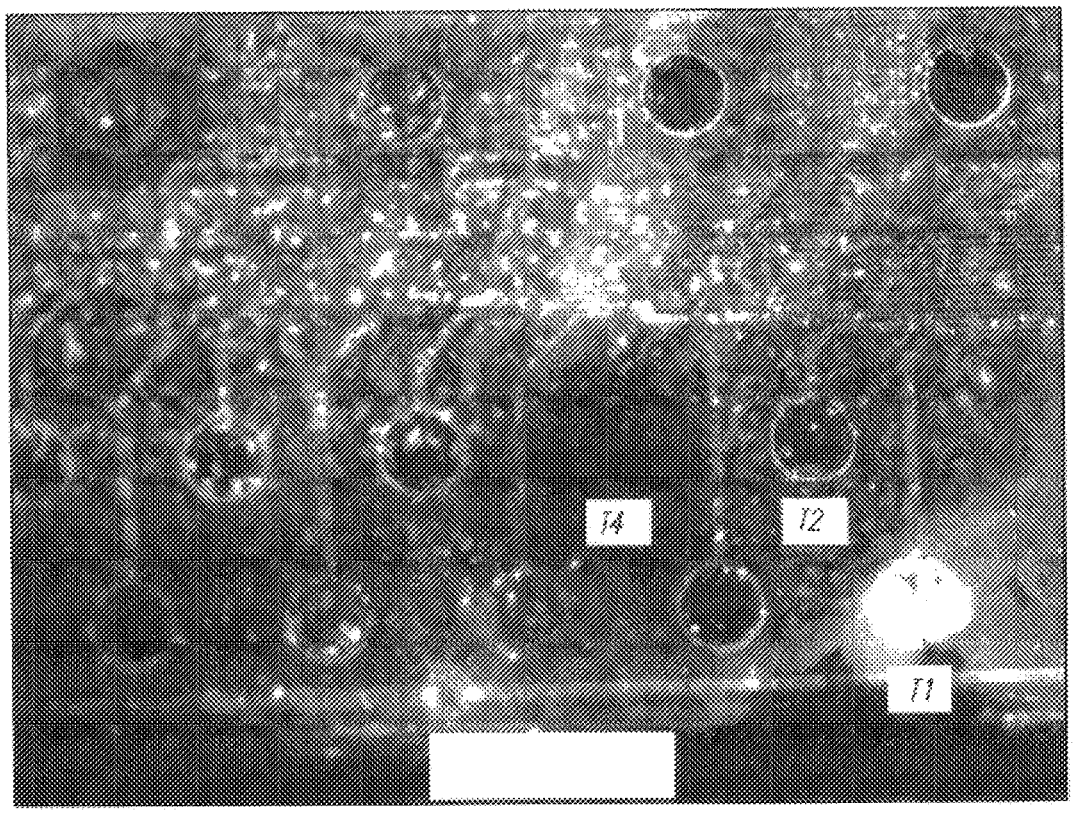
Figure 40A:
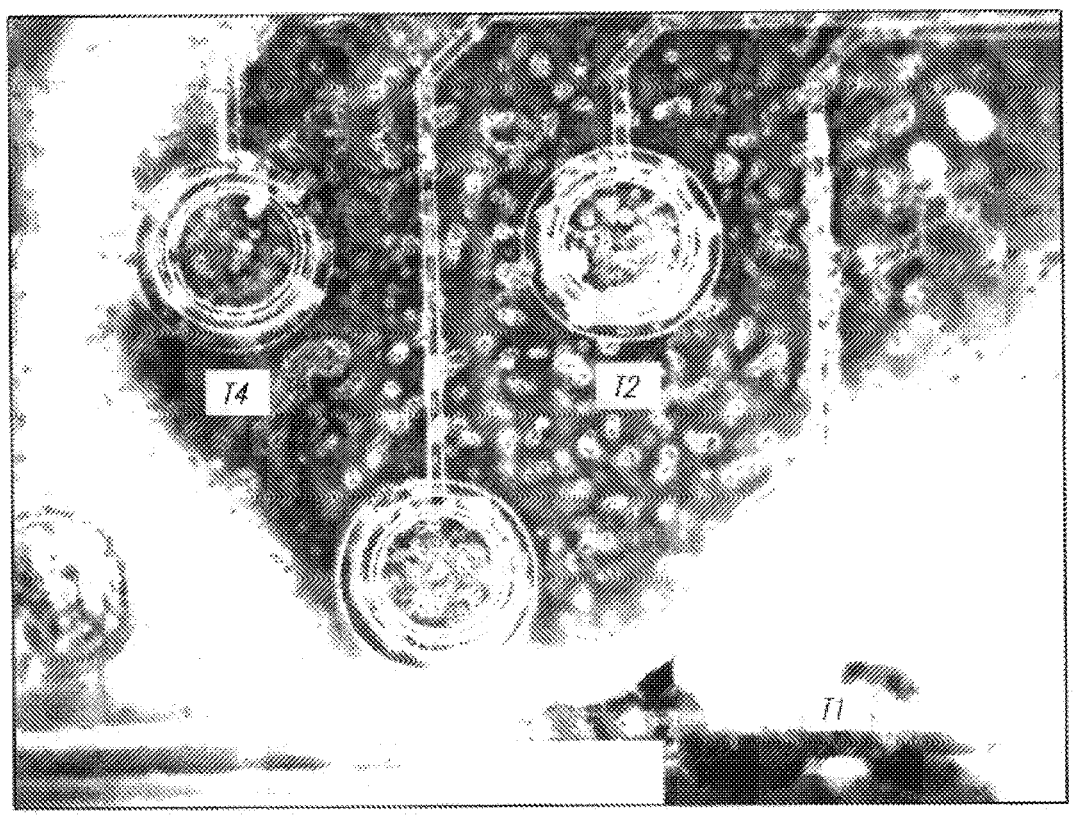
FIGS. 40a and 40b represent digitally captured epifluorescent photomicrographs taken through a 20× objective with a 100 millisecond integration time of the same hardwired electrodes as shown in FIGS. 39a and 39b.
Figure 40B:
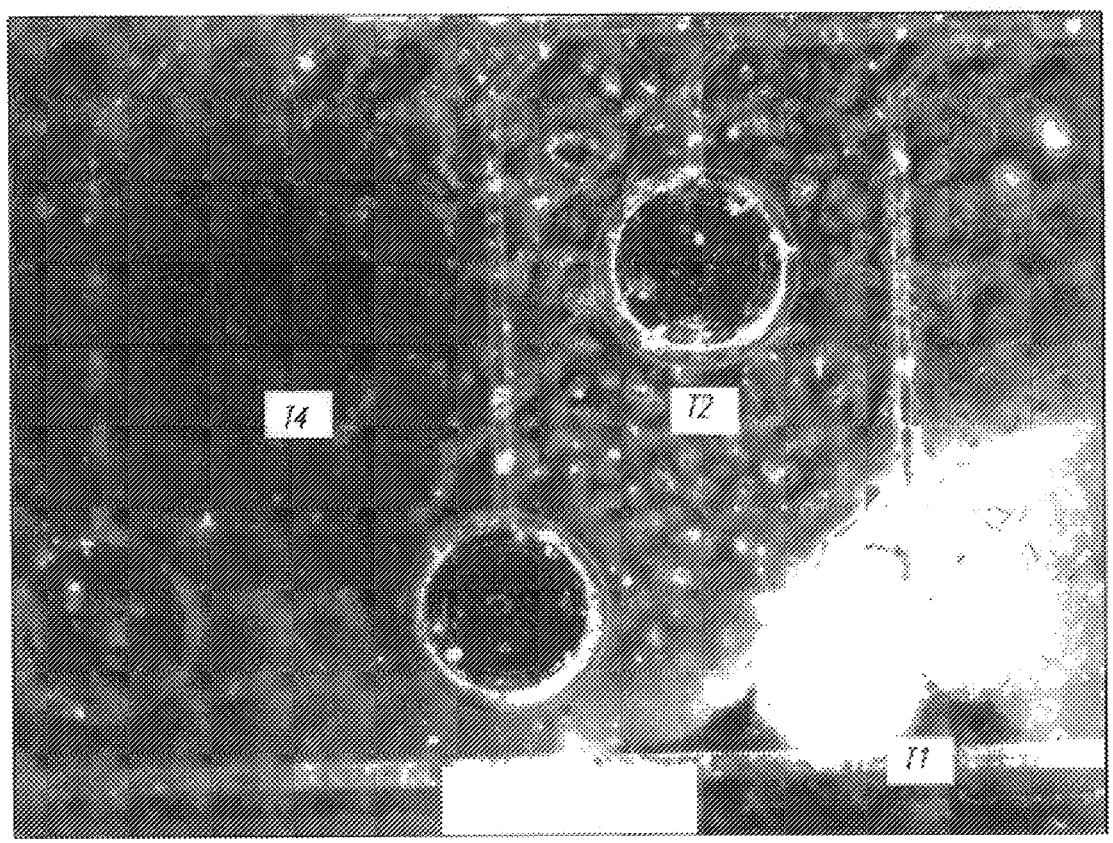

FIG. 38 shows the condition of anodes T2 and T4 following application of the voltage causing electrochemical generation of protons at the anodes and resultant dissociation of the trityl linker at these positions. Once dissociation occurred, the fluorescent labeled streptavidin molecules were washed away, leaving the anodes dark. Notably, anodes T2 and T4 are darker than the neighboring electrodes, indicating no chemical crosstalk was occurring.

As is shown by FIGS. 37 and 38, localization and selective deprotection were achieved at anodes T2 and T4, as was desired.

Deprotection Using Electrolyte of Southern (WO 93/24480)

All steps were performed identical to that for the above process in accordance with the present invention, except that instead of using a buffering solution in accordance with the invention, deprotection was performed in the presence of a 1% triethylammonium sulfate electrolyte in an acetonitrile solvent, as disclosed in the Examples of Southern.

The results of this process are shown in FIGS. 39a, 39b, 40a and 40b. In the electrodes shown, labeled T1 and T4, electrode T1 represented the cathode and electrode T4 represented the anode.

FIGS. 39a, 39b, 40a and 40b show that the membrane exhibited random and imprecise bright and dark areas. These bright and dark areas indicate that the protons generated at the anode (electrode T4) are not confined or localized to the area proximate the electrode, causing significant dissociation of the trityl linker over the entire field of the photomicrograph T1 appears to have retained most of the fluorescence directly above the electrode. This is explained by the base that is generated at the T1 cathode, which neutralized the acid generated proximate the T4 anode.

As is seen from a comparison of the photomicrographs illustrating the results achieved in accordance with the present invention (i.e., using a buffering solution overlaying the electrodes) and those illustrating the results achieved from the analogous experiment performed using the electrolyte of Southern (WO 93/22480), superior localization of the electrochemical generated reagents was achieved using the process of the present invention. The superior localization achieved in accordance with the present invention greatly reduced, if not eliminated, undesirable chemical crosstalk between proximate electrodes. In contrast, very little localization of the electrochemical generated reagents was achieved using the electrolyte of the prior art, resulting in random and imprecise deprotection over the entire field of the micrograph.

Example 5

Formation of Carbon-Carbon Bonds by Electrochemically-Catalyzed Olefin Addition Reactions.

Microscopy and chip control were performed according to the descriptions set forth in Examples 3 and 4 described above.

Electrode array chips comprising 16×64 platinum electrodes with thirteen ancillary hardwired electrodes were used in this example. Electrochemistry was conducted on a few of the hardwired electrodes found on the side of the array in this example. This example demonstrates the formation of carbon-carbon bonds by the method of this invention between an activated olefin immobilized proximate to one or a plurality of electrodes and an anhydride contained in a solution to which the one or a plurality of electrodes is exposed. The overlaying membrane was polysaccharide-based. The activated olefins were attached covalently to the overlaying membrane. More specifically, the activated olefins were acryloyl groups. The anhydride contained in the solution was a biotin anhydride.

An electrochemically activated catalyst was used to mediate the coupling of biotin to the immobilized olefins. More specifically vitamin $B_{12}$ was used as the catalyst. The active component of vitamin $B_{12}$ is a cobalt atom. Normally, the formal oxidation state of the cobalt atom in vitamin $B_{12}$ is +3 (Co(III)). Vitamin $B_{12}$ can be reduced electrochemically such that the formal oxidation state of the cobalt atom is +1(Co(I)). The Co(I) species is active as a catalyst that mediates the formation of carbon-carbon bonds.

Experimental Procedure

Preparation of Bulk Acryloyl Modified Polysaccharide Materials.

Acryloyl groups were added to hydroxyl moieties on polysaccharides by the following procedure. A mixture of 0.2 g of the bulk polysaccharide, 0.05 g of acryloyl chloride (Aldrich, Milwaukee, Wis.), 0.1 ml of pyridine (Aldrich, Milwaukee, Wis.) in 5 ml of DMF (Aldrich, Milwaukee, Wis.) was stirred at room temperature for 30 minutes. The suspended polysaccharide was isolated by filtration. The acryloyl-modified polysaccharide was washed with DMF, then deionized water, and then acetone. The washed filter cake was dried in vacuo overnight at room temperature.

Preparation of Biotin Anhydride.

A stirred suspension of 0.09 g of d-biotin (Sigma, St. Louis, Mo.) in 5 ml of dry THF (Aldrich, Milwaukee, Wis.) was degassed with dry nitrogen. 30 microliters of thionyl chloride (Aldrich, Milwaukee, Wis. was added dropwise to the stirred suspension. The reaction mixture was stirred under nitrogen at room temperature for one hour. All of the suspended d-biotin went into solution upon reaction. The solvent was evaporated and the remaining solid material taken up in 5 ml of dry THF and filtered. The filtrate was added dropwise to a stirred suspension of 0.09 g of d-biotin and 44 microliters of triethyl amine in 5 ml of dry THF. The reaction mixture was stirred under nitrogen for one hour at room temperature. The contents were then filtered. The product biotin anhydride was isolated by removing the solvent from the filtrate.

Preparation of the Chip for Attachment of Molecules.

To enable the attachment of molecules by vitamin $B_{12}$ mediated carbon-carbon bond formation proximate to the surface of the electrode array chip, the chip was coated/modified with an overlaying membrane of a polysaccharide-based material. Specifically, a polygalactoside that was modified with acryloyl groups was used as overlaying membrane materials in this example. The membrane was applied by spin coating onto the chip.

Elecrochemically Mediated Formation of Carbon-Carbon Bonds Between Biotin and Activated Olefin Groups.

A DMF solution that was 0.01M in biotin anhydride, 0.37 mM in vitamin $B_{12}$, and 0.032M in tetrabutylammonium nitrate was prepared. A chip was immersed in the solution and a potential difference of 3.0 V was applied between the anode and the cathode for 5 minutes. This was repeated with different pairs of electrodes as needed. After the electrochemistry was completed, chips were removed from solution and washed with deionized water and acetone.

Assay with Fluorescent Dye Labeled Molecules

The electrochemically modified chip was immersed in an aqueous solution of fluorescent dye (Texas Red) labeled streptavidin molecules having a concentration of 50 micrograms per milliliter and allowed to remain in this solution for one hour. Fluorescent dye labeled streptavidin was obtained from Vector Laboratories (Burlingame, Calif.). During this immersion, biotin molecules attached to the membrane formed a complex with the fluorescent dye labeled streptavidin molecules.

The chip was then washed with an aqueous 0.1M sodium phosphate buffer that was adjusted to pH 8.0 to remove dye labeled streptavidin that was not complexed with membrane bound biotin. The chip was now ready for evaluation by epifluorescent microscopy.

Results

Formation of Carbon-Carbon Bond Between Acryloyl Groups and Biotin

A potential difference of 3.0 V was applied between hardwired electrodes $T_1$ and $T_2$ for 5 minutes. $T_1$ was the cathode and $T_2$ was the anode. Then, a 3.0 V potential difference was applied across hardwired electrodes $T_2$ and $T_4$. $T_4$ was the cathode and $T_2$ was the anode. Electrochemical reduction of vitamin $B_{12}$ occurred at the cathodes. The chip was then exposed to Texas Red labeled streptavidin as described and the photomicrograph of FIG. 41 was obtained. Bright spots at the cathodes indicate the presence of biotin bound to the overlaying membrane. Control experiments were performed to rule out the possibility of unanticipated artifacts causing a false positive.

Control Experiments

To demonstrate that the observed results were due to the formation of carbon-carbon bonds between biotin and an immobilized activated olefin the following control experiments were performed. The conditions used in the control experiments were identical to the conditions used for the carbon-carbon bond forming experiments.

Figure 41:
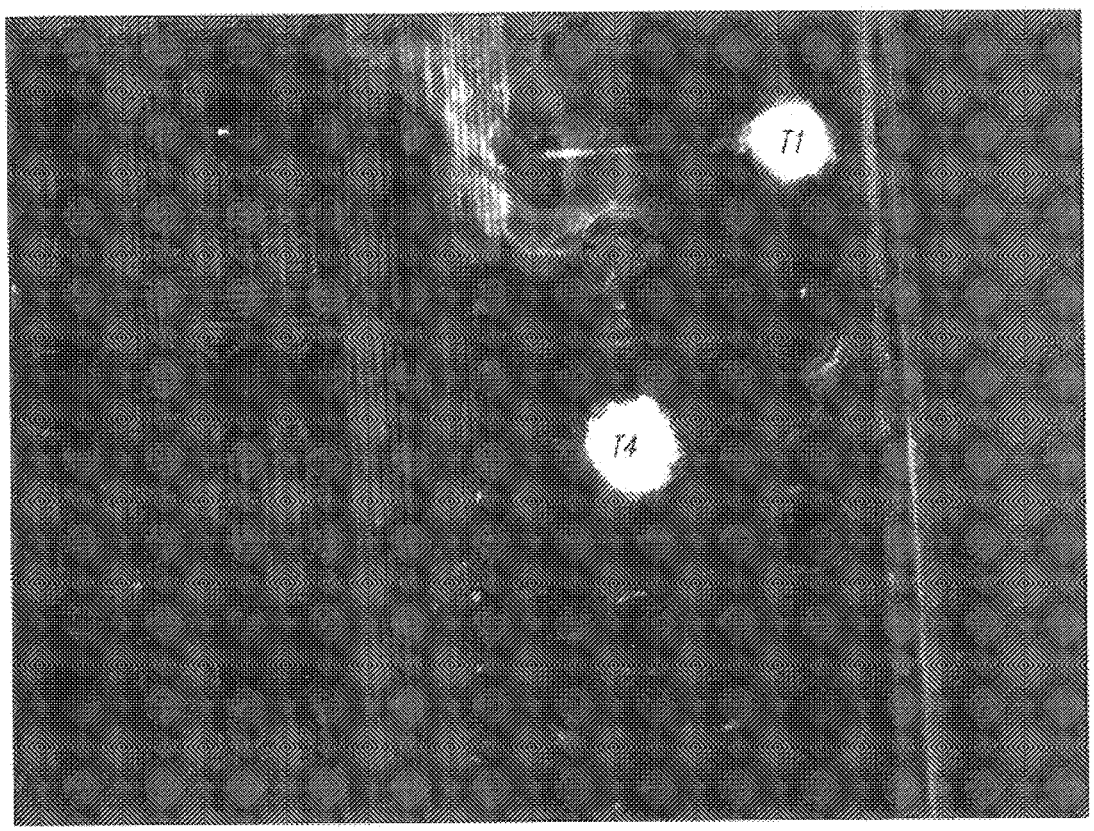
FIG. 41 represents electrochemical reduction of vitamin $B_{12}$ at the cathodes of electrode array chips described in Experiment 5. The chips were exposed to Texas Red labeled streptavidin and this photomicrograph was obtained. Bright spots at the cathodes indicate the presence of biotin bound to the overlaying membrane.
Figure 42:
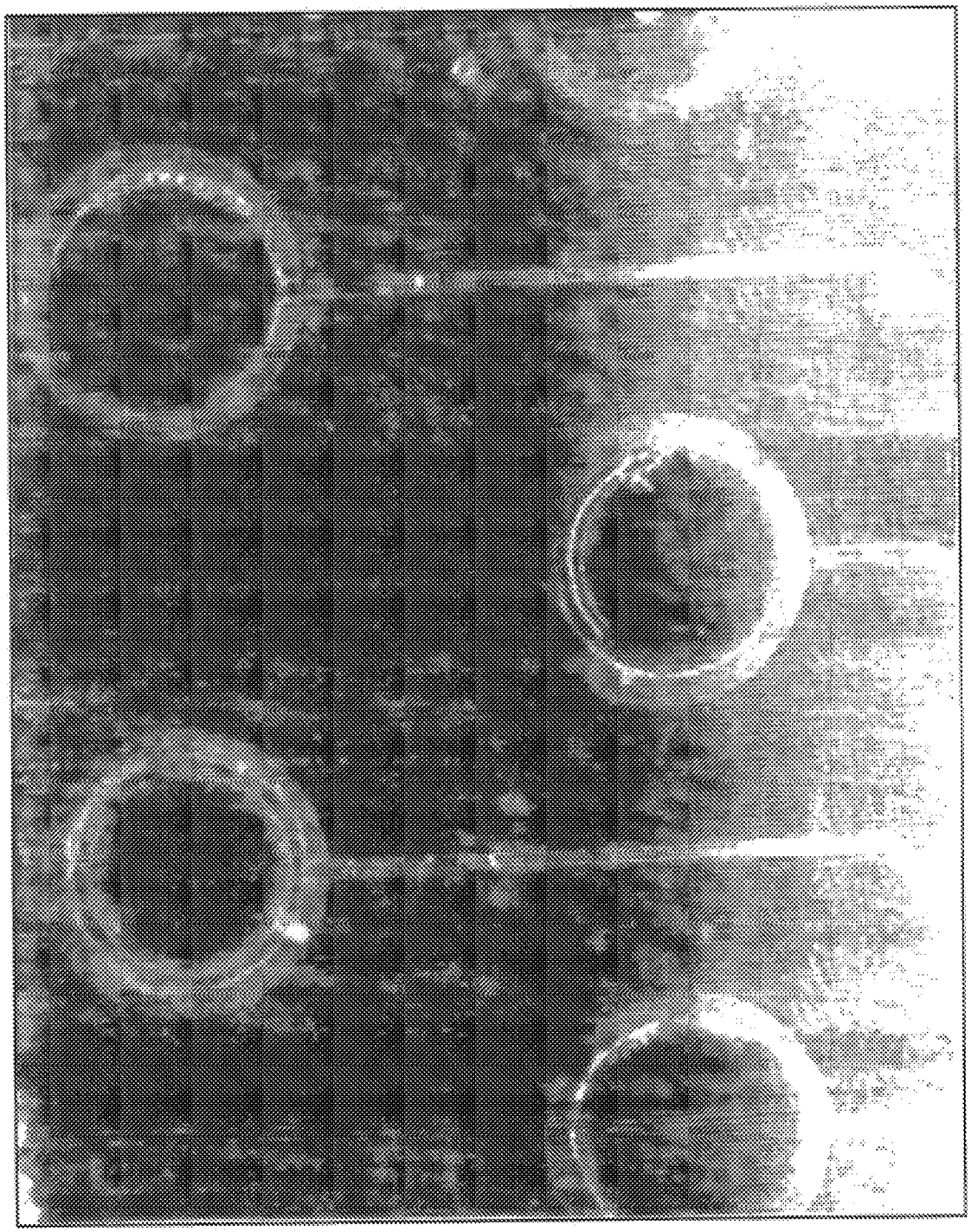
FIG. 42 confirms that the vitamin $B_{12}$ catalyst was necessary for the results depicted in FIG. 41. No vitamin $B_{12}$ was added to the solution and a voltage difference of 3.0 volts between the anode and the cathode was set. No observable current passed between the electrodes. At this potential difference, there are no electroactive species in solution without vitamin $B_{12}$. The chip was then exposed to Texas Red labeled streptavidin and washed. No evidence of carbon-carbon bond formation is seen.

A first control experiment was designed to confirm that the vitamin $B_{12}$ catalyst was necessary for the results obtained in FIG. 41. Chip was prepared with an acryloyl modified polysaccharide membrane as described. This chip was then immersed in a DMF solution identical to the DMF solution used to form carbon-carbon bonds, except that there was no vitamin $B_{12}$ added to the solution. A voltage difference of 3.0 volts between the anode and the cathode was set for 5 minutes. No observable current passed between the electrodes. At this potential difference, there are no electroactive species in solution without vitamin $B_{12}$. The first control chip was then exposed to Texas Red labeled streptavidin and washed in a procedure identical to the one outlined above. The results are shown in FIG. 42. No evidence of carbon-carbon bond formation is seen.

Figure 43:
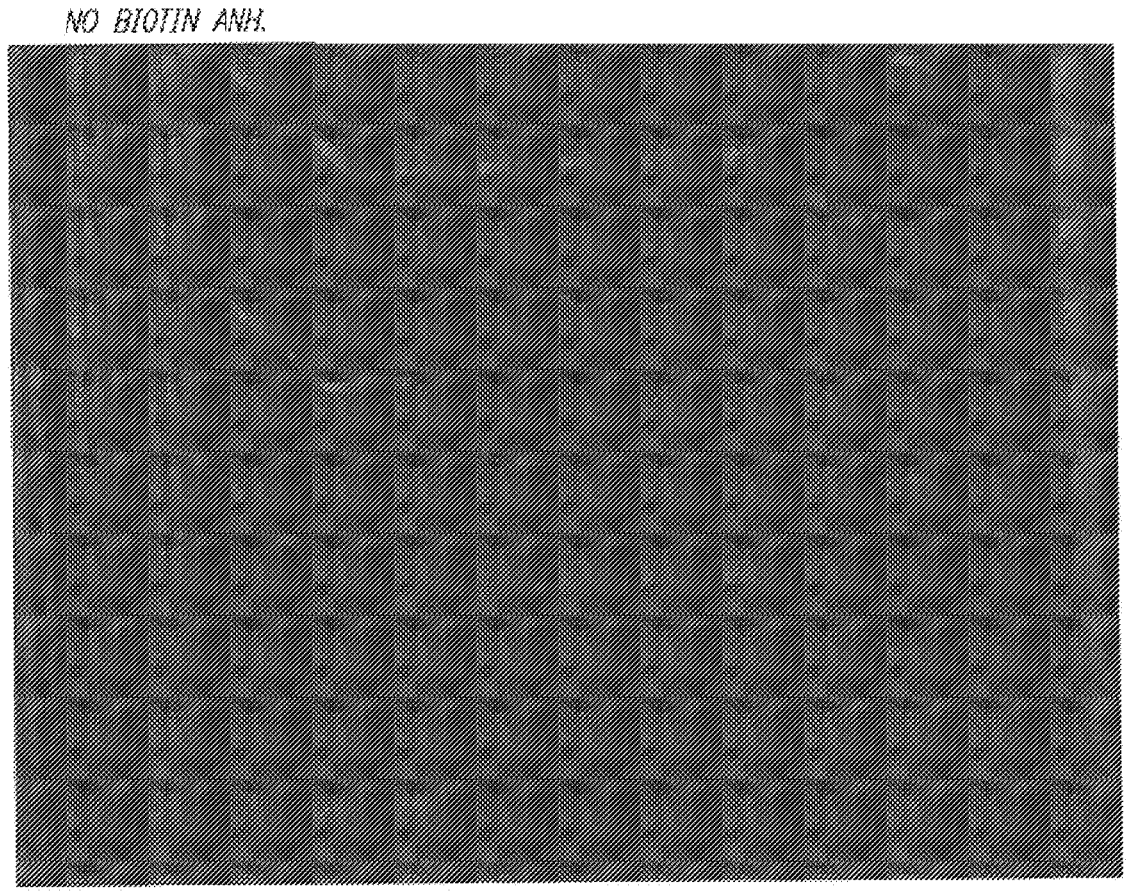
FIG. 43 confirms that the biotin anhydride substrate was necessary to obtain the results depicted in FIG. 41. A chip was immersed in a DMF solution identical to the DMF solution used to form carbon-carbon bonds, except that there was no biotin anhydride added to the solution. A voltage difference of 3.0 volts between the anode and the cathode was set. The chip was then exposed to Texas Red labeled streptavidin and washed. No evidence of carbon-carbon bond formation is seen.

A second control experiment was designed to confirm that the biotin anhydride substrate was necessary to obtain the results of FIG. 41. A chip was prepared with an acryloyl modified polysaccharide membrane as described. The chip was then immersed in a DMF solution identical to the DMF solution used to form carbon-carbon bonds, except that there was no biotin anhydride added to the solution. A voltage difference of 3.0 volts between the anode and the cathode was set for 5 minutes. The second control chip was then exposed to Texas Red labeled streptavidin and washed in a procedure identical to the one outlined above. The results are shown in FIG. 43. No evidence of carbon-carbon bond formation is seen.

Figure 44:
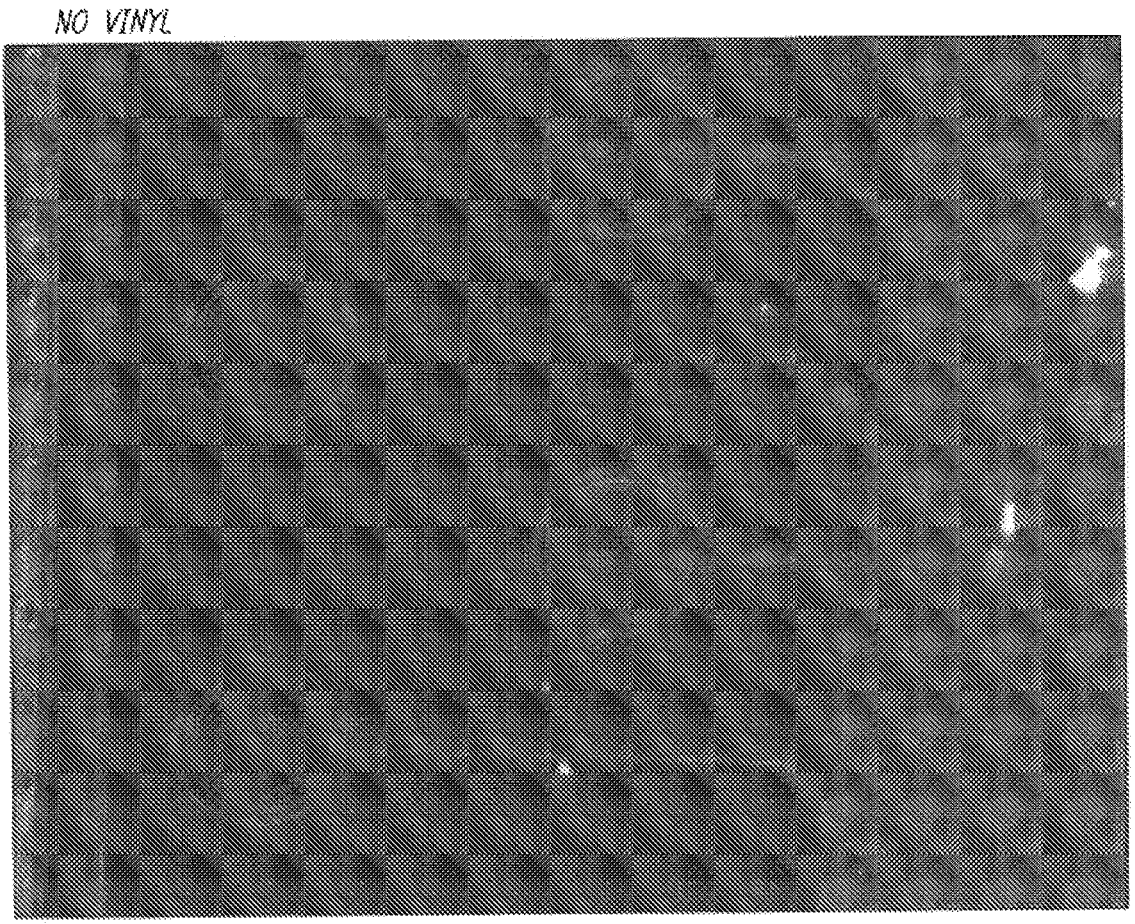
FIG. 44 confirms that the activated olefin was necessary to obtain the results depicted in FIG. 41. A chip was immersed in a DMF solution identical to the DMF solution used to form carbon-carbon bonds, except that there was no activated olefin attached to the overlaying membrane. A voltage difference of 3.0 volts between the anode and the cathode was set. The chip was then exposed to Texas Red labeled streptavidin and washed. No evidence of carbon-carbon bond formation is seen.

A third control experiment was designed to confirm that the activated olefin was necessary to obtain the results of FIG. 41. A chip was prepared with an unmodified polysaccharide membrane as described. The chip was then immersed in a DMF solution identical to the DMF solution used to form carbon-carbon bonds, except that there was no activated olefin attached to the overlaying membrane. A voltage difference of 3.0 volts between the anode and the cathode was set for 5 minutes. The third control chip was then exposed to Texas Red labeled streptavidin and washed in a procedure identical to the one outlined above. The results are shown in FIG. 44.

Example 6

Background

A major obstacle to exposing semiconductor devices to environments that contain ions is that the ions diffuse into the device. In particular, ions diffuse into regions of the device that have been doped with ions in a precise manner to impart particular electrical properties to these regions. An important example is the gate of a metal oxide semiconductor (MOS) transistor circuit element. Here either positive or negative ions (e.g., p-doped or n-doped) have been diffused into the gate region to make the region semiconducting. The threshold voltage and current-voltage characteristics of the transistor gate depend in a sensitive way on doping levels.

The long term reliability of many semiconductor devices depends on isolating them effectively from ionic contamination. The adhesives and encapsulants used in the semiconductor industry are treated to render the ion concentrations in these materials as low as possible, often less than parts per million.

Likewise, ion contamination represents a potential problem for utilizing devices comprising selected electrode(s) whose electrical activity is controlled by computer generated signaling because such devices would be immersed and operating in high concentration ionic solutions for extended periods of time. As a result, it is desirable to incorporate structures into such that are designed both to monitor and to obviate ion contamination.

Such devices are designed to work by scavenging ions that diffuse into the device from the solutions to which they are exposed. These contaminating ions can be scavenged passively by reacting chemically with a material that is placed between them and the active circuitry. Alternatively, they can be scavenged actively by applying a voltage to an electrode that sets up an electric field that causes ions to migrate to the electrode and away from the active circuitry. We call these electrodes 'gettering' structures. Ion contamination can be monitored by placing transistor gates adjacent to the gettering electrodes and monitoring shifts in threshold voltage.

Figure 45:
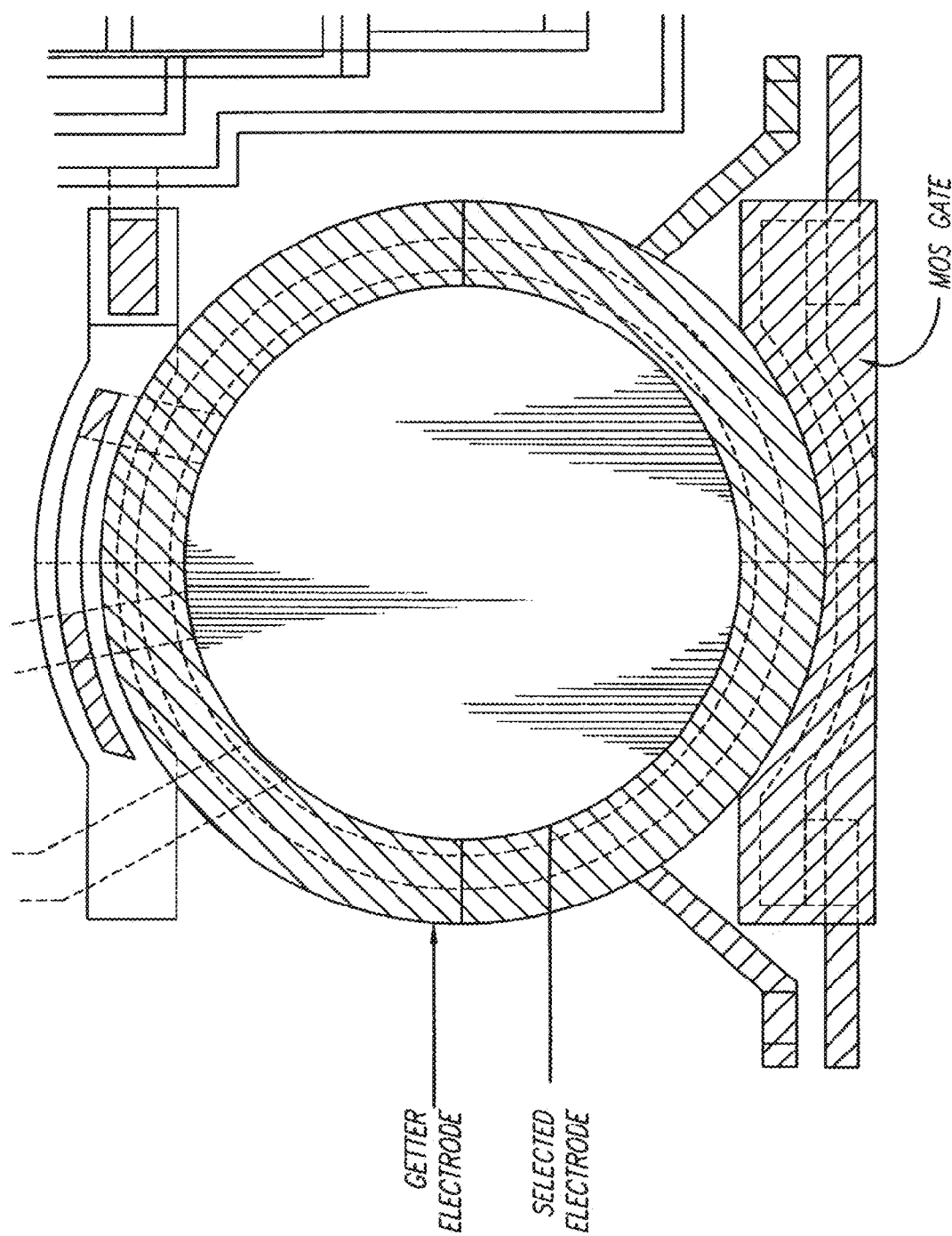
FIG. 45 depicts a transistor design representative of those used in electrode arrays in accordance with the present invention. A key feature is the placement of a "getter" structure which in this case is an electrode proximate to and in a ring around the selected electrode.
Figure 46:
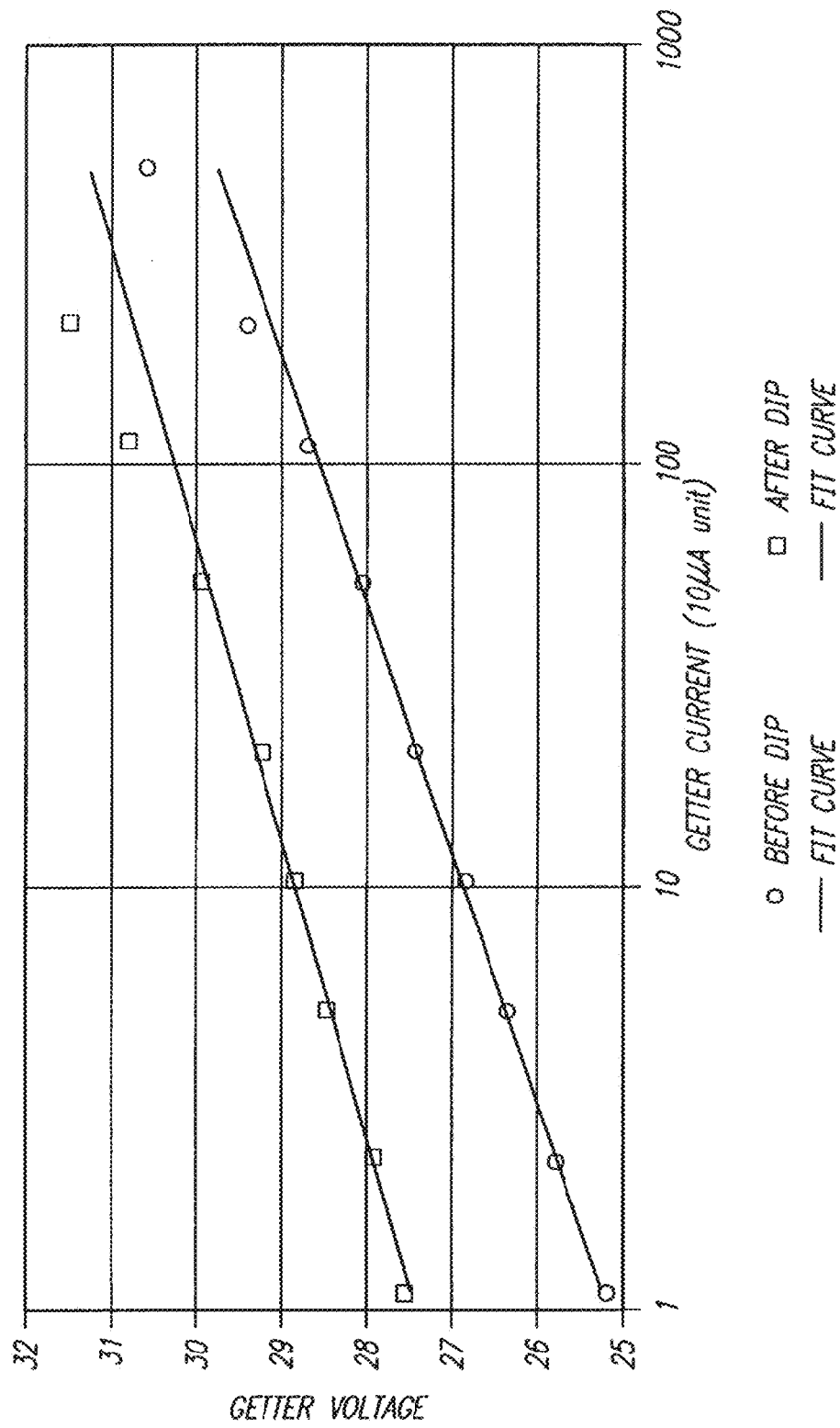
FIG. 46 demonstrates ionic contamination at the monitoring transistor when the chips were dipped into aqueous salt solutions. This illustrates the shift in the threshold voltage of the transistor monitoring device after a 20 minute exposure to a 0.1 M $NaPO_4$ solution. The measured data is fit to a subthreshold MOS curve of the form $V=V_0 \ln(I/I_0)$.

The time course of ionic contamination was monitored in such devices. To do this, a transistor using a ring getter electrode as a gate electrode was prepared. The MOS gate of this transistor was close to the electrochemical electrode. The MOS gate in this case is n-doped. The device was designed to allow getter voltages of up to 50 volts. The transistor design is illustrated in FIG. 45.

Results

Initial evaluation of the gettering device confirmed that there was ionic contamination at the monitoring transistor when the chips were dipped into aqueous salt solutions. FIG. 45 illustrates the shift in the threshold voltage of the transistor monitoring device after a 20 minute exposure to a 0.1 M $NaPO_4$ solution. The measured data is fit to a subthreshold MOS curve of the form $V = V_0 \ln(I/I_0)$.

Ions appear to contaminate the MOS gate of the monitoring transistor fairly quickly. The threshold voltage goes up, indicating that sodium ions are the primary contaminating species. The threshold voltage goes up because the conductivity of the MOS gate goes down. Since the MOS gate is n-doped, this means that positive sodium ions are, to some extent, neutralizing the negative ions that were used to dope the gate.

Figure 47:
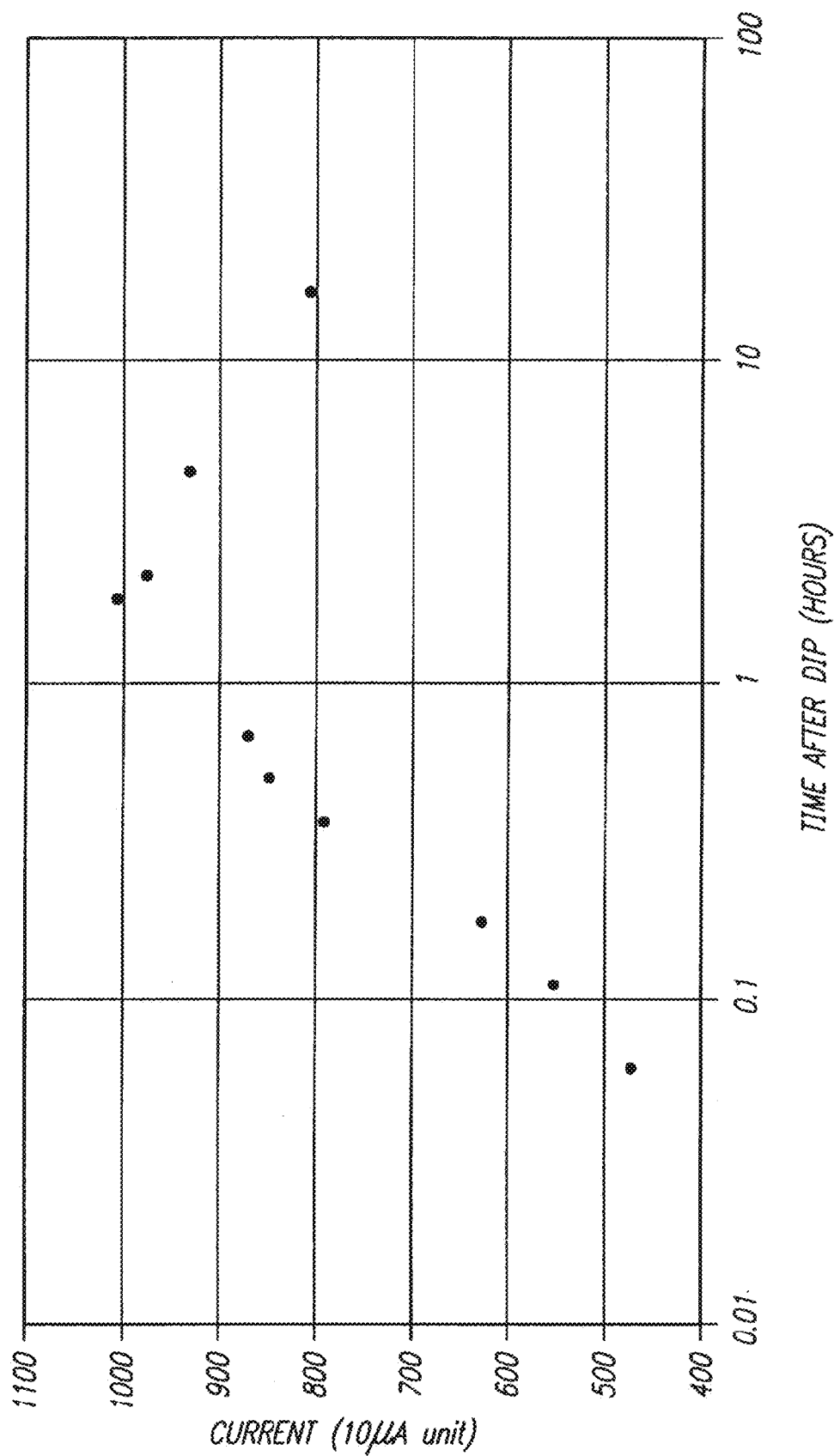
FIG. 47 demonstrates that the getter current continues to rise for several hours after initial exposure to ions indicating a concomitant lowering in the threshold voltage of the gate. These results indicate that the sodium ions are diffusing away from the gate region. The time course of the current rise follows an approximately logarithmic course for the first few hours.

There is a secondary mode of contamination. It is possible that the surface layers of the chip are contaminated quickly, but the effects are not seen in the circuitry until much later. Because ions diffuse so slowly in the dielectric material of the chip, it may take some time before the ions in the surface contamination layer diffuse into the circuitry of the device. This was tested by immersing a chip for 20 minutes in an aqueous 0.1 M sodium phosphate solution. The chip was then removed from the solution, washed and dried. A getter electrode was set to 32 volts and the current monitored over time. The chip was not exposed to any solution after the initial 20 minute exposure. The results are shown in FIG. 47. The getter current continues to rise for several hours after the initial exposure to ions indicating a concomitant lowering in the threshold voltage of the gate. In other words, sodium ions are diffusing away from the gate region. The time course of the current rise follows an approximately logarithmic course for the first few hours. This is consistent with a self-screening diffusion process. Long term contamination is a problematic issue. Even though chips may seem fine after an initial exposure to salt solutions, they may fail later due to incipient surface contamination problems. Using a "getter" structure in accordance with the present invention effectively decreases such contamination.

I claim:

1. A method for detecting binding of a target molecule to a capture molecule on a microarray device, comprising the steps of:
    (a) receiving the microarray device with a surface including:
        a plurality of independently addressable electrodes;
    (b) covering the surface with a porous reaction layer;
    (c) attaching using in situ synthesis electrochemical techniques, a plurality of capture molecules to the porous reaction layer at sites over the plurality of independently addressable electrodes;
    (d) contacting the microarray device with a plurality of target molecules which include:
        an oxidation/reduction enzymatic moiety attached to one or more molecules selected from the group consisting of antibody, anti-idiotype antibody, antigen, biotin, avidin and streptavidin; and
        a substrate molecule in solution proximate to the oxidation/reduction enzymatic moiety, where the substrate molecule creates a local voltage signal when catalyzed by the oxidation/reduction enzymatic moiety through local generation of electrochemical reagents;
    (e) applying an amperometric potential to one or more selected electrodes from the plurality of independently addressable electrodes;

(f) measuring a current while applying the amperometric potential of step (e) on the plurality of independently addressable electrodes;

(g) waiting a period of time for the current to level off;

(h) comparing the current measured in step (f) after the period of time specified in step (g) at the plurality of independently addressable electrodes to determine sites having one or more of the plurality of target molecules bound to one or more of the plurality of capture molecules and sites not having one or more of the plurality of target molecules bound to any of the plurality of capture molecules;

(i) determining a current difference at the sites having one or more of the plurality of target molecules bound to one or more of the plurality of capture molecules compared with the sites not having one or more of the plurality of target molecules bound to any of the plurality of capture molecules; and (j) using the current difference measured in step (i) to determine binding of one or more of the plurality of target molecules to one or more of the plurality of capture molecules.

2. The method of claim 1, wherein the oxidation/reduction enzymatic moiety is selected from the group consisting of laccase, horseradish peroxidase, ß-galactosidase, glucose oxidase, alkaline phosphatase, dehydrogenases, and combinations thereof.

3. The method of claim 1, wherein the target molecules are selected from the group consisting of DNA, RNA, single-stranded DNA, ribosomal RNA, mitochondrial DNA, cellular receptors, glycosylated membrane-bound proteins, non-glycosylated membrane-bound proteins), polypeptides, glycosylated polypeptides, antibodies, cellular antigenic determinants, organic molecules, metal ions, salt anions and cations, and combinations thereof.

4. The method of claim 1, wherein the oxidation/reduction enzymatic moiety comprises a first antibody attached to an end of the target molecules, an antigen attached to the first antibody, a second antibody attached to the antigen, a streptavidin-biotin complex or an avidin-biotin complex attached to the second antibody, and an oxidation/reduction enzyme attached to the steptavidin-biotin complex or the avidin-biotin complex.

5. The method of claim 1, where the porous reaction layer has a thickness of between:
 a lower limit of approximately 0.1 microns; and
 an upper limit of approximately 10 microns.

6. The method of claim 1, where the period of time is 2 minutes.

7. A method of detecting binding of a target molecule to a capture molecule, comprising:
 (a) receiving a Complimentary Metal Oxide Semiconductor (CMOS) microarray including:
  parallel addressing for applying a potential at a plurality of addressable electrodes;
  a porous reaction layer attached to the CMOS microarray between 0.1 microns and 10 microns in thickness; and
  a plurality of oligonucleotide capture molecules attached to the porous reaction layer at sites over the plurality of addressable electrodes, where the plurality of oligonucleotide capture molecules has a first sequence;
 (b) exposing the plurality of oligonucleotide capture molecules to target molecules including:
  an oxidation/reduction enzymatic moiety that is attached to a streptavidin moiety; and
  a biotinylated oligonucleotide substrate molecule in solution proximate to the oxidation/reduction enzymatic moiety, where the biotinylated oligonucleotide substrate molecule has a second sequence, where the second sequence is complementary to the first sequence;
 (c) applying an amperometric potential to one or more selected electrodes from the plurality of addressable electrodes;
 (d) measuring a current while applying the amperometric potential of step (c) on the plurality of addressable electrodes;
 (e) waiting a period of time for the current to level off;
 (f) comparing the current measured in step (d) after the period of time specified in step (e) at the plurality of addressable electrodes to determine sites having the target molecules bound to one or more of the plurality of oligonucleotide capture molecules and sites not having target molecules bound to the plurality of oligonucleotide capture molecules;
 (g) measuring a current difference at the sites having the target molecules bound to the plurality of oligonucleotide capture molecules compared with the sites not having target molecules bound to the plurality of oligonucleotide capture molecules; and
 (h) using the current difference measured in step (g) to determine binding of a target molecule to an oligonucleotide capture molecule.

8. The method of claim 7, where the oxidation/reduction enzymatic moiety is one or more enzymes selected from the group consisting of laccase, horseradish peroxidase, ß-galactosidase, glucose oxidase, alkaline phosphatase and dehydrogenases.

9. The method of claim 7, where the period of time is 2 minutes.

10. A method for detecting a voltage signal difference between sites having a target molecule and sites not having the target molecule, comprising:
 (a) receiving a Complimentary Metal Oxide Semiconductor (CMOS) microarray including:
  parallel addressing for applying a potential at a plurality of addressable electrodes;
  a porous reaction layer attached to the CMOS microarray; and
  a plurality of oligonucleotide capture molecules attached to the porous reaction layer at sites over the plurality of addressable electrodes, where the plurality of oligonucleotide capture molecules has a first sequence;
 (b) exposing the plurality of oligonucleotide capture molecules to one or more target molecules, where the one or more target molecules include:
  an oxidation/reduction enzymatic moiety that is attached to a streptavidin moiety; and
  a biotinylated oligonucleotide substrate molecule in solution proximate to the oxidation/reduction enzymatic moiety, where the biotinylated oligonucleotide substrate molecule has a second sequence, where the second sequence is complementary to the first sequence;
 (c) adding a substrate for the oxidation/reduction enzymatic moiety, where the substrate and the oxidation/reduction enzymatic moiety create a local voltage to one or more selected electrodes from the plurality of addressable electrodes;

(d) measuring a current while applying the amperometric potential of step (c) on the plurality of addressable electrodes;
(e) waiting a period of time for the current to level off;
(f) comparing the current measured in step (d) after the period of time specified in step (e) at the plurality of addressable electrodes to determine sites having the one or more target molecules bound to one or more of the plurality of oligonucleotide capture molecules and sites not having one or more target molecules bound to the plurality of oligonucleotide capture molecules;
(g) measuring a current difference at the sites having the one or more target molecules bound to the plurality of oligonucleotide capture molecules compared with the sites not having the one or more target molecules bound to the plurality of oligonucleotide capture molecules; and
(h) using the current difference measured in step (g) to determine binding of a target molecule to an oligonucleotide capture molecule.

11. The method of claim 10, where the oxidation/reduction enzymatic moiety is one or more enzymes selected from the group consisting of laccase, horseradish peroxidase, ß-galactosidase, glucose oxidase, alkaline phosphatase and dehydrogenases.

12. The method of claim 10, where the one or more target molecules are one or more species selected from the group consisting of DNA, RNA, single-stranded DNA, ribosomal RNA, mitochondrial DNA, cellular receptors, glycosylated membrane-bound proteins, non-glycosylated membrane-bound proteins), polypeptides, glycosylated polypeptides, antibodies, cellular antigenic determinants, organic molecules, metal ions, salt anions and cations.

13. The method of claim 10, where the porous reaction layer has a thickness of between:
a lower limit of approximately 0.1 microns; and
an upper limit of approximately 10 microns.

14. The method of claim 10, where the period of time is 2 minutes.

* * * * *